US006498233B1

(12) United States Patent
Wels et al.

(10) Patent No.: US 6,498,233 B1
(45) Date of Patent: Dec. 24, 2002

(54) NUCLEIC ACID TRANSFER SYSTEM

(75) Inventors: Winfried Wels, Glimpenheimer Strasse 55, D-79312 Emmendingen (DE); Jesus Fominaya, Madrid (ES)

(73) Assignee: Winfried Wels, Rodgau (DE)

( * ) Notice: Subject to any disclaimer, the term of this patent is extended or adjusted under 35 U.S.C. 154(b) by 0 days.

(21) Appl. No.: 08/840,713

(22) Filed: Apr. 25, 1997

Related U.S. Application Data

(63) Continuation-in-part of application No. PCT/EP95/04270, filed on Oct. 31, 1995.

(30) Foreign Application Priority Data

Nov. 1, 1994 (GB) .......................................... 94810627

(51) Int. Cl.⁷ ............................................. C07K 19/00
(52) U.S. Cl. ..................................................... 530/350
(58) Field of Search ......................... 530/350; 536/23.1

(56) References Cited

U.S. PATENT DOCUMENTS 5,668,255 A * 9/1997 Murphy ...................... 530/350

FOREIGN PATENT DOCUMENTS

| DE | 43 39 922 | | 10/1994 |
| WO | WO 94/04696 | * | 3/1994 |
| WO | WO 95/28494 | * | 10/1995 |

OTHER PUBLICATIONS

Michael and Curiel, *Gene Therapy* vol. 1, No. 4, (Jul.) 1994, pp. 223–232, "Strategies to achieve targeted gene delivery via the receptor–mediated endocytosis pathway".

* cited by examiner

*Primary Examiner*—Terry McKelvey
(74) *Attorney, Agent, or Firm*—Arent Fox Kintner Plotkin & Kahn PLLC

(57) ABSTRACT

The invention pertains to a nucleic acid transfer system including a translocation domain of toxins, especially of diphtheria toxin suitable for targeting a nucleic acid, e.g. a gene, to a specific cell, and obtaining expression of said nucleic acid. The nucleic acid transfer system of the invention comprises a multidomain protein component and a nucleic acid component. Furthermore, the present invention relates to the multidomain protein, a nucleic acid encoding said protein, suitable amplification and expression systems for said nucleic acid, and processes for the preparation and uses of the above subject matters.

3 Claims, No Drawings

NUCLEIC ACID TRANSFER SYSTEM

CROSS REFERENCE TO RELATED APPLICATION

This application is a continuation-in-part of International Application PCT/EP95/04270, filed Oct. 31, 1995, and designating the U.S.

The invention pertains to a nucleic acid transfer system suitable for targeting a nucleic acid, e.g. a gene, to a specific cell, and obtaining expression of said nucleic acid. The nucleic acid transfer system of the invention comprises a multidomain protein component and a nucleic acid component. Furthermore, the present invention relates to the multidomain protein, a nucleic acid encoding said protein, suitable amplification and expression systems for said nucleic acid, and processes for the preparation and uses of the above subject matters.

Gene transfer to eukaryotic cells may be accomplished using viral vectors, such as recombinant adenoviruses, or non-viral gene transfer vectors. Owing to several disadvantages, e.g. constraints in the size of the DNA to be delivered, incapability of transducing terminally differentiated cells, potential safety hazards and insufficient targetability, such viral DNA transfer systems seem to be of limited use in gene therapy strategies. As an alternative to viral systems, ligand-mediated approaches via molecular conjugate vectors have been developed. Such molecular conjugate vectors comprise the DNA molecule to be transferred and a target cell-specific ligand which is chemically coupled to a polycation, particularly a polyamine (for review, see e.g. Michael & Curiel, Gene Therapy 1: 223, 1994). The polycation binds to the DNA through electrostatic forces, thus acting to tie up the ligand with the gene to be delivered. For example, human transferrin or chicken conalbumin were covalently linked to poly-L-lysine or protamine through a disulfide linkage. Complexes of protein-polycation—conjugate and a bacterial plasmid containing a luciferase encoding gene were supplied to eukaryotic cells, resulting in expression of the luciferase gene (Wagner et al., Proc. Natl. Acad. Sci. USA 87: 3410, 1990). To achieve higher levels of gene expression, adenovirus particles were chemically coupled to the complex (see e.g. Curiel et al., Proc. Natl. Acad. Sci. USA 88: 8850, 1991; Christiano et al., Proc. Natl. Acad. Sci. USA 90: 11548, 1993). However, molecular conjugate vectors also have limitations, including large size, inhomogeneity, lack of specificity pertaining to the binding of the DNA component, and non-specific binding due to electrostatic interactions between the polycation and the cell membrane, which may at least partially neutralize the targetability imposed by the ligand.

Thus there is still a need for a simple, efficient nucleic acid transfer system which allows e.g. the target cell-specific introduction of nucleic acids to be expressed, but lacks the disadvantages of the prior art concepts.

It is the object of the present invention to provide such a system. The nucleic acid transfer system according to the invention is characterized by the following two components:
1) a multi-domain protein comprising several functional domains including a nucleic acid binding domain
2) an effector nucleic acid, particularly a DNA, comprising the nucleic acid, e.g. the gene, to be delivered to and expressed in a selected target cell, and a cognate structure recognizable by the nucleic acid binding domain of the protein.

The multi-domain protein component combines in a single molecule a target cell recognition function, also referred to as ligand domain, an endosome escape function and a nucleic acid binding function, particularly a DNA binding function. Such a protein does not occur in nature. The nucleic acid binding function serves to mediate the specific, high affinity and non-covalent interaction of the protein component with the effector nucleic acid component. Unlike the above described molecular conjugate vector of the prior art, the protein/nucleic acid complex of the present invention is formed by specific interaction of the nucleic acid binding domain with its cognate structure on the effector nucleic acid. Advantageously, the binding affinity of the proteinaceous nucleic acid binding domain for its cognate structure on the effector nucleic acid surpasses the affinity of the proteinaceous target cell recognition function for its cognate molecular structure on the target cell. Within the nucleic acid transfer system of the present invention the effector nucleic acid component may be e.g. a complete or partial plasmid carrying the nucleic acid to be expressed in the target cell. The nucleic acid delivery system of the invention is designed such that the rate of nucleic acid transfer is optimized.

Advantageously, the present system makes use of physiological target-cell inherent mechanisms of macromolecular transport involving endosomes, particularly receptor-mediated endocytosis. The protein/nucleic acid complex according to the invention is targetable in that it may be efficiently internalized only by a predetermined cell-type or cell population carrying a molecular structure, e.g. a receptor, which specifically interacts with the target cell recognition function of said complex. After entering the cell, the protein/nucleic acid complex of the invention becomes localized in endosomes from where it is released into the cytoplasm. Owing to the selective internalization of the protein/nucleic acid complex, expression of the particular nucleic acid(s) to be delivered by the complex of the invention occurs in a way that distinguishes (transfected) target cells from (non-transfected) non-target cells, e.g expression is essentially confined to the predetermined target cell. The nucleic acid to be transported to and expressed in the target cell may be therapeutically active or encode a therapeutically active product, e.g. tumor cells may be transfected to introduce a gene coding for a therapeutically active protein.

More specifically, the present invention provides a two-component system for the target cell-specific delivery and uptake of a non-covalently linked protein/nucleic acid complex leading to the expression in said target cells of one or more nucleic acids comprised by the transferred effector nucleic acid. Preferentially, such system of the invention essentially consists of a protein/nucleic acid complex containing two components:
  a polypeptide chain containing several different functional, domains of eukaryotic, prokaryotic or synthetic origin, and
  an effector nucleic acid.

Advantageously, the protein/nucleic acid complex is sufficiently stable in physiological fluids to enable its application in vivo. The complex of the invention is a molecular complex, whose stochiometry is essentially determined by the number of cognate structures of the protein nucleic acid binding domain on the effector nucleic acid. For example, the cognate structure of the yeast GAL4 binding domain is thought to bind a protein dimer. Accordingly, the ratio of multidomain protein to effector nucleic acid in the complex of the invention is 2:1 by using one nucleic acid binding domain. However, it is preferred to use nucleic acids which contain multiple sequences (preferably 2–8 which recognize the nucleic acid binding domain).

Successful transfer and expression of the desired nucleic acid depends on the specific interaction of the protein/nucleic acid complex with the target cell and on the efficient transfer of the nucleic acid of interest across systemic or subcellular barriers. To examine whether the complex of the invention is transported into or within the target cell, the complex may be suitably labeled and its accumulation on and in cells determined, e.g. by fluorescence imaging. For example, the complex may be fluoresence-labeled and its cellular localization be visualized, e.g. by video-enhanced microscopy and quantitative confocal laser scanning. Other assays suitable for determining the functionality of the nucleic acid transfer system of the invention, such as an assay for the expression of a delivered reporter gene, are described in the Examples. Further assays are known in the art and evident to the skilled person.

The nucleic acid delivery system of the invention provides for e.g. for efficient gene transfer in that it enables e.g. transit of said gene through the eukaryotic cell plasma membrane, transport to the nucleus, nuclear entry and functional maintenance within the nucleus. Persistence of gene expression can be achieved either by stable chromosomal integration of heterologous DNA or by maintenance of an extrachromosomal replicon. Preferably, the system of the invention lacks sequences which raise safety issues, e.g. complete viral genomes capable of autonomous replication or containing viral oncogenes. A system of the present invention may be designed such as to provide a safe, non-toxic and efficient in vivo nucleic acid transfer system.

In a further aspect, the present invention relates to the above captioned multidomain protein which is capable of specifically binding to an effector nucleic acid as defined according to the invention by its nucleic acid binding domain and mediating the introduction of said effector nucleic acid into a target cell.

The multidomain protein of the invention which may comprise one or more polypeptide chains is produced using chemical and/or recombinant methods known in the art. Preferably, said protein is a recombinant single chain protein.

The functional domains characterizing the protein of the invention are:

(1) a target cell-specific binding or ligand domain recognizing a cellular surface structure, e.g. an antigenic structure, a receptor protein or other surface protein, which mediates internalization of a bound ligand.

(2) a translocation domain facilitating the escape of the effector nucleic acid from endocytic vesicles after internalization of said complex into target cells, e.g. via receptor mediated endocytosis, (3) a nucleic acid binding domain recognizing and binding with high affinity to a defined structure of the effector nucleic acid component, e.g. to a specific DNA sequence on a suitable eukaryotic expression plasmid or a suitable linear DNA fragment, and, optionally, (4) an endoplasmic reticulum retention signal affecting the intracellular routing of the internalized protein/nucleic acid complex, and (5) a nuclear localisation signal.

There is particularly preferred a multidomain protein comprising, as functional domains, a target cell-specific binding domain, a translocation domain and a nucleic acid binding domain, characterized in that the translocation domain is derivable from diphtheria toxin and does not include that part of said toxin molecule which confers to the cytotoxic effect of the molecule; or a multidomain protein comprising, as functional domains, a target cell-specific binding domain, a translocation domain and a nucleic acid binding domain, characterized in that the translocation domain is derivable from bacterial toxins and the target cell-specific binding domain which recognizes a cell surface receptor selected from the group of the EGF receptor-related family of growth factor receptors; or a multidomain protein comprising, as functional domains, a target cell-specific binding domain, a translocation domain and a nucleic acid binding domain, characterized in that the translocation domain is derivable from a bacterial toxin and the target cell-specific binding domain recognizes a cell surface receptor on the effector cells of the immune system.

Within the multidomain protein of the invention the above captioned independent components function in a concerted manner to achieve targeted, highly efficient internalization of a nucleic acid of interest provided by an effector nucleic acid, e.g. by an eukaryotic expression plasmid, to a selected cell or cell population, thereby contributing to the successful expression of said nucleic acid of interest. The arrangement of the component domains is chosen in accordance with the functionality of the individual domains. In an embodiment of the invention using a translocation domain derivable from a toxin, e.g., P. aeruginsosa exotoxin A or diphtheria toxin, the arrangement of domains in N- to C-terminal order may be as follows: ligand binding domain—translocation domain—nucleic acid binding domain—(optionally) endoplasmic reticulum retention signal.

The protein of the invention may comprise one or more functional domains serving the same function. For example, to facilitate binding of the effector nucleic acid, the protein may comprise one or more nucleic acid binding domains recognizing the same or different cognate structures on the effector nucleic acid. The protein may comprise one or more ligand domains having the same or different specificities. As evident form the Examples, one copy of each functional domain is sufficient for a multidomain protein of the invention to perform its above captioned function.

In addition to these functional domains the protein component may comprise one or more, particularly one, two, three or four further amino acid sequences. For example, such inserts, preferably consisting of genetically encoded amino acids, may advantageously be incorporated into the multidomain protein of the invention to serve as a linker or spacer between the above identified functional domains. Thus the insert connects the C-terminal amino acid of one functional domain with the N-terminal amino acid of another functional domain. A suitable insert may not impair the favorable properties of the multidomain protein as such. For example, a linker may be a peptide consisting of about 1 to about 20 amino acids. Exemplary inserts include peptides having the amino acid sequences GluLysLeuGluSerSerAspTyrLysAspGluLeu (SEQ ID NO:40), HisHis, HisHisHisHis (SEQ ID NO:41), SerSerAspTyrLysAspGluLeu (SEQ ID NO:42), and other sequences evident from the Examples. Additional amino acids may also be incorporated at the N-terminus of the multidomain protein. Exemplary amino acid sequences include the FLAG epitope and are identified for SEQ ID NOs. 1, 3 and 5 in the Examples.

The target cell-specific binding domain is chosen so as to achieve targetability and cellular internalization of the protein/nucleic acid complex of the invention. It enables the specific interaction of the protein/nucleic acid complex of the invention with a selected structure on the target cell which structure mediates cellular internalization by, for example, the process of endocytosis. Preferably, said domain attaches to the target cells in a fashion compatible with a ligand receptor union, thereby mediating entry of the protein/nucleic acid complex into the cell. In the protein/ nucleic acid complex of the invention said ligand domain maintains the ability of the "parent protein" it is derivable from to bind to the cognate structure, e.g. the receptor, in such a way that endocytosis of said complex is accomplished. Preferred is a target cell-specific binding domain, recognition and binding of which by its appropriate cell surface receptor allows cellular internalization of the protein/nucleic acid complex via receptor-mediated endocytosis.

A precondition for a proteinaceous molecule to be suitable as a binding domain in the multidomain protein of the invention is that it binds to a surface-structure on specific target cells, which surface structure is capable of mediating internalization of its ligand into the target cell via an endocytotic pathway and that these properties are not substantially impaired for the multidomain protein of the invention.

A target cell-specific binding domain recognizing a cell surface structure, such as a receptor protein or a surface antigen on the target cell, is e.g. derivable from a ligand of a cell specific receptor, such as a Fc receptor, transferrin receptor, EGF receptor, asialoglycoprotein receptor, cytokine receptor, such as a lymphokine receptor, a T cell specific receptor, e.g. CD 45, CD4 or CD8, the CD 3 receptor complex, TNF receptor, CD 25, erbB-2, an adhesion molecule, such as NCAM or ICAM, and mucine. Suitable ligands include antibodies specific for said receptor or antigen. Further molecules suitable as ligand domain in the multidomain protein of the invention include factors and growth factors, e.g tumor necrosis factor, e.g. TNF-a, human growth factor, epidermal growth factor (EGF), platelet-derived growth factor PDGF), transforming growth factor (TGF), such as TGFa or TGFb, nerve growth factor, insulin-like growth factor, a peptide hormone, e.g. glucagon, growth hormone, prolactin, or thyroid hormone, a cytokine, such as interleukin, e.g. IL-2 or IL-4, interferon, e.g. IFN-g, or fragments or mutants of such proteins with the provision that such fragments and mutants fulfill the above requirements for a ligand domain. For example, suitable antibody fragments include Fab fragments, Fv constructs, e.g. single chain Fv contructs (scFv) or an Fv construct involving a disulfide bridge, and the heavy chain variable domain. The ligand domain may be of natural or synthetic origin and will vary with the particular type of target cell.

Especially preferred, as target cell-specific binding domains, are domains which recognize (bind to) a cell surface receptor selected from the groups of the EGF-receptor related family of growth factor receptors. Such cell surface receptors are, e.g., TGFα receptor, EGF receptor, erbB2, erbB3 or erbB4 (Pelles, E., and Yarden, Y., Bioassays 15 (1993) 815–824). Preferred as binding domains in the transfer system are growth factors like herregulin, EGF, betacellulin, TFG-α, amphiregulin or heparin binding EGF as well as antibodies against erbB2, erbB3, erbB4 or EGF receptor.

Further preferred are cell surface structures of effector cells of the immune. system, especially of T cells. Such structures are, e.g., IL-2 receptor, CD4 or CD8.

Whether in the multidomain protein of the invention the ligand domain is capable of recognizing and binding its cognate structure may be determined according to methods known in the art. For example, a competition assay may be employed to determine whether entry of the protein/DNA complex of the invention is specifically mediated by the target cell-specific binding domain. For example, if excess of the free ligand serving as ligand domain, or of the free protein the target cell-specific binding domain is derivable from, competes with binding, endocytosis and nuclear localization of the suitably labeled complex, binding and entry of the complex into the cell is specifically mediated by said target cognate moiety of the complex.

A preferred ligand domain is e.g. a single chain antigen binding domain of an antibody, e.g. a domain derivable from the heavy chain of an antibody, and particularly a single chain recombinant antibody (scFv). Preferentially, the antigen binding domain is a single-chain recombinant antibody comprising the light chain variable domain ($V_L$) bridged to the heavy chain variable domain ($Y_H$) via a flexible linker (spacer), preferably a peptide. Advantageously, the peptide consists of about 10 to about 30 amino acids, particularly naturally occurring amino acids, e.g. about 15 naturally occurring amino acids. Preferred is a peptide consisting of amino acids selected from L-glycine and L-serine, in particular the 15 amino acid peptide consisting of three repetitive units of Gly-Gly-Gly-Gly-Ser (SEQ ID NO:43). Advantageous is a single-chain antibody wherein $V_H$ is located at the N-terminus of the recombinant antibody. The antigen binding domain may be derivable from a monoclonal antibody, e.g. a monoclonal antibody directed against and specific for a suitable antigen on a tumor cell.

A suitable antigen is an antigen with enhanced or specific expression on the surface of a tumor cell as compared to a normal cell, e.g. an antigen evolving from consistent genetic alterations in tumor cells. Examples of suitable antigens include ductal-epithelial mucine, gp 36, TAG-72, growth factor receptors and glycosphingolipids and other carbohydrate antigens preferentially expressed on tumor cells. Ductal-epithelial mucine is enhancedly expressed on breast, ovarian and pancreas carcinoma cells and is recognized e.g. by monoclonal antibody SM3 (Zotter et al., Cancer Rev. 11, 55–101 (1988)). The glycoprotein gp 36 is found on the surface of human leukemia and lymphoma cells. An exemplary antibody recognizing said antigen is SN 10. TAG-72 is a pancarcinoma antigen recognized by monoclonal antibody CC49 (Longenecker, Sem. Cancer Biol. 2, 355–356). Growth factor receptors are e.g. the human epidermal growth factor (EGF) receptor (Khazaie et al., Cancer and Metastasis Rev. 12, 255–274 (1993)) and HER2, also referred to as erbB-2 or gp 185 (A. Ullrich and J. Schlessinger, Cell 61, 203–212 (1990)). The erbB-2 receptor is a transmembrane molecule which is overexpressed in a high percentage of human carcinomas (N. E. Hynes, Sem. in Cancer Biol. 4, 19–26 (1993)). Expression of erbB-2 in normal adult tissue is low. This difference in expression identifies the erbB-2 receptor as "tumor enhanced".

Preferably, the antigen binding domain is obtainable from a monoclonal antibody produced by immunization with viable human tumor cells presenting the antigen in its native form. In a preferred embodiment of the invention, the recognition part of the multidomain protein of the invention specifically binds to an antigenic determinant on the extracellular domain of a growth factor receptor, particularly HER 2. Monoclonal antibodies directed to the HER2 growth factor receptor are known and are described, for example, by S. J. McKenzie et al., Oncogene 4, 543–548 (1990), R. M. Hudziak et al., Molecular and Cellular Biology 9, 1165–1172 (1989), International Patent Application WO 89/06692 and Japanese Patent Application Kokai 02-150 293. Monoclonal antibodies raised against viable human tumor cells presenting HER2 in its native form, such as SKBR3 cells, are described, for example, in European patent application EP-A-502 812 which is enclosed herein by reference, and include antibodies FRP5, FSP16,FSP77and FWP51 (ECACC90112115, 90112116, 90112117 and 90112118).

Most preferred is the single chain antibody scFv(FRP5) as described in the Examples and SEQ ID NOs. 1 and 2.

Further preferred as a ligand domain is a cognate structure binding fragment derivable from a cytokine, particularly TGF-a or interleukin-2. Particularly preferred is a TGF-a fragment having the sequence set forth in SEQ ID No. 4, which sequence extends from the amino acid at position 13 (Val) to the amino acid at position 62 (Ala). Equally preferred is a IL-2 fragment having the sequence set forth in SEQ ID No. 6, which sequence extends from the amino acid at position 18 (Ala) to the amino acid at position 150 (Thr).

Particularly preferred are the ligand domains as employed in the Examples. The amino acid sequences of the domains designated sc(Fv)FRP5, TGF-a and IL-2 are identified for SEQ. ID. Nos. 1, 3 and 5, respectively.

Within the present invention a target cell is a cell that via a specific cell surface structure is capable of selectively binding the target cell-specific binding domain comprised in the protein/nucleic complex of the invention. The cell surface structure may be a protein, a carbohydrate, a lipid or combination thereof Advantageously, such target cell possesses a unique receptor which—by binding to the target cell-specific binding domain of the multi-domain protein of the invention—mediates the efficient internalization of substantially the protein/nucleic acid complex into the target cell.

Within the multidomain protein of the invention the translocation domain functions to enhance nucleic acid escape from the cellular vesicle system and thus to augment nucleic acid transfer by this route. This domain serves to reduce or avoid lysosomal degradation after internalization of the protein/nucleic acid complex into the target cell. WO 94/04696 describes a nucleic acid transfer system wherein, as a translocation domain and a receptor binding domain, the cognate domains of P. exotoxin A are used. However, the transfection efficiency and specificity of such transfer systems are very low. The invention, therefore, provides an improved nucleic acid transfer system exhibiting a high transfection efficiency and specificity. Suitable translocation domains are derivable from toxins, particularly bacterial toxins, such as exotoxin A, Colicin A, d-endotoxin, diphtheria toxin, Bacillus anthrox toxin, Cholera toxin, Pertussis toxin, *E. coli* toxins, Shigatoxin or a Shiga-like toxin. The translocation domain does not include that part of the parent toxin molecule which confers the cytotoxic effect of the molecule. Advantageously, the translocation domain of the recombinant protein of the invention is derivable or essentially derivable from that very part of the parent toxin which mediates internalization of the toxin into the cell, e.g. amino acids 194 or 196 to 378 or 384 of diphtheria toxin. Therefore, the part of the toxin used in the nucleic acid transfer system according to the invention does not contain a cell binding domain of a toxin.

The nucleic acid binding domain enables the specific binding of the protein component of the nucleic acid transfer system of the invention to the effector nucleic acid component of said complex. The high affinity interaction of the nucleic acid binding domain with the corresponding cognate sturctur on the effector nucleic acid links the cell recognition part to the expression effector part. The nucleic acid binding domain may be a RNA binding domain, or preferentially, a DNA binding domain, e.g. the DNA binding domain of a transcription factor, particularly a yeast or human transcription factor. Preferred is a GAL4 derivable domain, mediating the selective binding of the protein of the invention to the DNA sequence CGGAGGACAGTCCTCCG (SEQ ID NO:44). According to Cavey et al. (J. Mol. Biol. 209: 423, 1989) GAL4 amino acids 1 to 147 exhibit a 50% saturation binding to the GAL4 recognition sequence at $2\times10^{-11}$M. Most preferably, the DNA binding domain of the protein of the invention consists of GAL4 amino acids 2 to 147 and has the amino acid sequence as identified for SEQ ID NO. 1 (see Example 10). A DNA binding domain may bind to a single-stranded, or preferably, to a double-stranded DNA on the effector nucleic acid.

An endoplasmic reticulum retention signal functions to affect the intracellular routing of the internalized protein/nucleic acid complex of the invention. A suitable endoplasmic retention signal may be a mammalian endoplasmic reticulum retention signal, e.g. the signal having the amino acid sequence LysAspGluLeu (SEQ ID NO:45), i.e. the KDEL signal identified for SEQ ID NOs. 1, 3 and 5, or a functionally equivalent amino acid sequence derivable from a bacterial toxin, e.g. REDLK (SEQ ID NO:46) (single amino acid code, from ETA) or from yeast (HDEL (SEQ ID NO:47), single amino acid code).

A preferred recombinant protein of the invention comprises in e.g. as a ligand domain a single-chain antibody domain specific for the human erbB-2 receptor protein, a suitable TTF-a derivable fragment, or an IL-2 derivable fragment, a translocation domain derivable from Pseudomonas exotoxin A or diphtheria toxin, a DNA binding domain derivable from the yeast GAL4 transcription factor and a mammalian endoplasmic reticulum retention signal KDEL. Particularly preferred are the multi-domain proteins comprising the following sequences: amino acids 18 to 530 as set forth in SEQ ID No. 2, amino acids 13 to 342 as set forth in SEQ ID No. 4, or amino acids 18 to 421 in SEQ ID No. 6.

In addition to the above identified functional domains a recombinant protein of the invention may also include a signal peptide, e.g. the *E. coli* OmpA signal sequence having the amino acid sequence MetLysLysThrAlaIleAlaIleAla-ValAlaLeuAlaGlyPheAlaThrValAlaGlnAla (SEQ ID NO:48).

The present invention also relates to a nucleic acid, i.e. a RNA or, particularly, a DNA, encoding the above described multidomain protein of the invention, or a fragment of such a nucleic acid. By definition, such a DNA comprises a coding single stranded DNA, a double stranded DNA of said coding DNA and complementary DNA thereto, or this complementary (single stranded) DNA itself. Exemplary nucleic acids encoding a protein of the invention are represented in SEQ ID NOs. 1, 3 and 5. A DNA encoding the protein designated TGFa-deltaETA-deltaGAL4 is obtainable from *E. coli* XL1Blue/pWF47-TGF which has been deposited with the Deutsche Sammlung von Mikroorganismen und Zellkulturen GmbH (DSM), Mascheroder Weg 1 b, D-38124 Braunschweig, under accession number 9513 on Oct. 24, 1994.

Preferred are nucleic acids having substantially the same nucelotide sequence as the coding sequences set forth in SEQ ID Nos. 1, 3 and 5, respectively, or novel fragments thereof. As used herein, nucleotide sequences which are substantially the same share at least about 90% sequence identity.

Exemplary nucleic acids can alternatively be characterized as those nucleic acids which encode a multidomain protein of the invention and hybridize to any of the DNA sequences set forth in SEQ ID Nos. 1, 3 and 5. Preferred are such sequences which hybridize under high stringency conditions to the above mentioned DNAs.

Stringency of hybridization refers to conditions under which polynucleic acids hybrids are stable. Such conditions are evident to those of ordinary skill in the field. As known to those of skill in the art, the stability of hybrids is reflected in the melting temperature ($T_m$) of the hybrid which decreases approximately 1 to 1.5° C. with every 1% decrease in sequence homology. In general, the stability of a hybrid is a function of sodium ion concentration and temperature. Typically, the hybridization reaction is performed under conditions of higher stringency, followed by washes of varying stringency. The person skilled in the art is readily able to choose suitable hybridization conditions.

Given the guidance provided herein, the nucleic acids of the invention are obtainable according to methods well known in the art. For example, a DNA of the invention is obtainable by chemical synthesis, using polymerase chain reaction (PCR) or by screening a library expressing a protein of interest, e.g. a ligand domain or a parent protein the ligand domain is derivable from, at a detectable level. Suitable libraries are commercially available or can be prepared e.g. from cell lines, tissue samples, and the like. After screening the library, positive clones are identified by detecting a hybridization signal.

Chemical methods for synthesis of a nucleic acid of interest are known in the art and include triester, phosphite, phosphoramidite and H-phosphonate methods, PCR and other autoprimer methods as well as oligonucleotide synthesis on solid supports. These methods may be used if the entire nucleic acid sequence of the nucleic acid is known, or the sequence of the nucleic acid complementary to the coding strand is available. Alternativly, if the target amino acid sequence is known, one may infer potential nucleic acid sequences using known and preferred coding residues for each amino acid residue.

An alternative means to isolate a DNA coding for an above mentioned functional domain is to use PCR technology as described e.g. in section 14 of Sambrook et al., 1989. This method requires the use of oligonucleotide probes that will hybridize to the nucleic acid of interest.

As used herein, a probe is e.g. a single-stranded DNA or RNA that has a sequence of nucleotides that includes at least about 20 contiguous bases that are the same as (or the complement of) any 20 or more contiguous bases of the nucleic acid of interest. The nucleic acid sequences selected as probes should be of sufficient length and sufficiently unambiguous so that false positive results are minimized. The nucleotide sequences are usually based on conserved or highly homologous nucleotide sequences or regions of the protein of interest. The nucleic acids used as probes may be degenerate at one or more positions. The use of degenerate oligonucleotides may be of particular importance where a library is screened from a species in which preferential codon usage in that species is not known.

Preferred regions from which to construct probes include 5' and/or 3' coding sequences, sequences predicted to encode ligand binding sites, and the like. Preferably, nucleic acid probes, are labelled with suitable label means for ready detection upon hybridization. For example, a suitable label means is a radiolabel. The preferred method of labelling a DNA fragment is by incorporating $^{32}$P-labelled a-dATP with the Klenow fragment of DNA polymerase in a random priming reaction, as is well known in the art. Oligonucleotides are usually end-labelled with $^{32}$P-labelled g-ATP and polynucleotide kinase. However, other methods (e.g. non-radioactive) may also be used to label the fragment or oligonucleotide, including e.g. enzyme labelling and biotinylation.

A nucleic acid of the invention can be readily modified by nucleotide substitution, nucleotide deletion, nucleotide insertion or inversion of a nucleotide stretch, and any combination thereof. Such mutants can be used e.g. to produce a multifunctional mutant protein comprising one or more functional domains that have an amino acid sequence differing from the sequences as found in nature. Mutagenesis may be predetermined (site-specific) or random. A mutation which is not a silent mutation must not place sequences out of reading frames and preferably will not create complementary regions that could hybridize to produce secondary mRNA structure such as loops or hairpins.

The DNA encoding a multidomain protein of the invention may be incorporated into vectors for further manipulation. As used herein, vector (or plasmid) refers to discrete elements that are used to introduce heterologous DNA into cells for either expression or replication thereof. Selection and use of such vehicles are well within the skill of the artisan. Many vectors are available, and selection of an appropriate vector will depend on the intended use of the vector, i.e. whether it is to be used for DNA amplification or for DNA expression, the size of the DNA to be inserted into the vector, and the host cell to be transformed with the vector. Each vector contains various components depending on its function (amplification of DNA or expression of DNA) and the host cell for which it is compatible. The vector components generally include, but are not limited to, one or more of the following: an origin of replication, one or more marker genes, an enhancer element, a promoter, a transcription termination sequence and a signal sequence.

Both expression and cloning vectors generally contain nucleic acid sequence that enable the vector to replicate in one or more selected host cells. Typically in cloning vectors, this sequence is one that enables the vector to replicate independently of the host chromosomal DNA, and includes origins of replication or autonomously replicating sequences. Such sequences are well known for a variety of bacteria, yeast and viruses. The origin of replication from the plasmid pBR322 is suitable for most Gram-negative bacteria, the 2m plasmid origin is suitable for yeast, and various viral origins (e.g. SV 40, polyoma, adenovirus) are useful for cloning vectors in mammalian cells. Generally, the origin of replication component is not needed for mammalian expression vectors unless these are used in mammalian cells competent for high level DNA replication, such as COS cells.

Most expression vectors are shuttle vectors, i.e. they are capable of replication in at least one class of organisms but can be transfected into another organism for expression. For example, a vector is cloned in *E. coli* and then the same vector is transfected into yeast or mammalian cells even though it is not capable of replicating independently of the host cell chromosome. DNA may also be amplified by insertion into the host genome. However, the recovery of such DNA is more complex than that of exogenously replicated vector because it requires restriction enzyme digestion. DNA can be amplified by PCR and be directly transfected into the host cells without any replication component.

Advantageously, expression and cloning vector contain a selection gene also referred to as selectable marker. This gene encodes a protein necessary for the survival or growth of transformed host cells grown in a selective culture medium. Host cells not transformed with the vector containing the selection gene will not survive in the culture medium. Typical selection genes encode proteins that confer resistance to antibiotics and other toxins, e.g. ampicillin, neomycin, methotrexate or tetracycline, complement auxotrophic deficiencies, or supply critical nutrients not available from complex media.

As to a selective gene marker appropriate for yeast, any marker gene can be used which facilitates the selection for transformants due to the phenotypic expression of the marker gene. Suitable markers for yeast are, for example, those conferring resistance to antibiotics G418, hygromycin or bleomycin, or provide for prototrophy in an auxotrophic yeast mutant, for example the URA3, LEU2, LYS2, TRP1, or HIS3 gene.

Since the amplification of the vectors is conveniently done in *E. coli*, an *E. coli* genetic marker and an *E. coli* origin of replication are advantageously included. These can be obtained from *E. coli* plasmids, such as pBR322, Blueskript vector or a pUC plasmid, e.g. pUC18 or pUC19, which contain both *E. coli* replication origin and *E. coli* genetic marker conferring resistance to antibiotics, such as ampicillin.

Suitable selectable markers for mammalian cells are those that enable the identification of cells competent to take up the nucleic acid encoding a protein of the invention, such as dihydrofolate reductase (DHFR, methotrexate resistance), thymidine kinase, or genes confering resistance to G418 or hygromycin. The mammalian cell transformants are placed under selection pressure which only those transformants are uniquely adapted to survive which have taken up and are expressing the marker. In the case of the DHFR marker, selection pressure can be imposed by culturing the transformants under conditions in which the methotrexate concentration of selection agent in the medium is successively increased, thereby leading to amplification (at its chromosomal integration site) of both the selection gene and the linked DNA that encodes the multidomain protein of the invention. In that case amplification is the process by which genes in greater demand for the production of a protein critical for growth are reiterated in tandem within the chromosomes of successive generations of recombinant cells. Increased quantities of the protein of the invention are usually synthesized from thus amplified DNA.

Expression and cloning vectors usually contain a promoter that is recognized by the host organism and is operably linked to the nucleic acid of the invention. Such promoter may be inducible or constitutive. The promoters are operably linked to DNA encoding the protein of the invention by removing the promoter from the source DNA by restriction enzyme digestion and inserting the isolated promoter sequence into the vector.

Promoters suitable for use with prokaryotic hosts include, for example, the b-lactamase and lactose promoter systems, alkaline phosphatase, a tryptophan (trp) promoter system and hybrid promoters such as the tac promoter. Their nucleotide sequences have been published, thereby enabling the skilled worker operably to ligate them to DNA encoding a protein of the invention, using linkers or adaptors to supply any required restriction sites. Promoters for use in bacterial systems will also generally contain a Shine-Dalgarno sequence operably linked to the DNA encoding the protein of the invention.

Suitable promoting sequences for use with yeast hosts may be regulated or constitutive and may be derivable from a highly expressed yeast gene, especially a *Saccharomyces cerevisiae* gene. Such genes are known by those skilled in the art.

DNA transcription from vectors in mammalian hosts may be controlled by promoters derived from the genomes of viruses such as polyoma virus, adenovirus, fowlpox virus, bovine papilloma virus, avian sarcoma virus, cytomegalovirus (CMV), a retrovirus and Simian Virus 40 (SV40), from heterologous mammalian promoters such as the actin promoter or a very strong promoter, e.g. a ribosomal protein promoter, provided such promoters are compatible with the host cell systems.

Transcription of a DNA encoding a multidomain protein of the invention by higher eukaryotes may be increased by inserting an enhancer sequence into the vector. Enhancers are relatively orientation and position independent. Many enhancer sequences are known from mammalian genes (e.g. elastase and globin). However, typically one will employ an enhancer from a eukaryotic cell virus. Examples include the SV40 enhancer on the late side of the replication origin (bp 100–270) and the CMV early promoter enhancer.

Expression vectors used in eukaryotic host cells—suitable envisaged host cells include yeast, fungi, insect, plant, animal, human, or nucleated cells from other multicellular organisms will also contain sequences necessary for the termination of transcription and for stabilizing the mRNA. Such sequences are commonly available from the 5' and 3' untranslated regions of eukaryotic or viral DNAs or cDNAs.

An expression vector refers to a recombinant DNA or RNA construct, such as a plasmid, a phage, recombinant virus or other vector, that upon introduction into an appropriate host cell, results in expression of the cloned DNA. Appropriate expression vectors are well known to those with ordinary skill in the art and include those that are replicable in eukaryotic and/or prokaryotic cells and those that remain episomal or those which integrate into the host cell genome.

Construction of vectors according to the invention employs conventional ligation techniques. Isolated plasmids or DNA fragments are cleaved, tailored, and religated in the form desired to generate the plasmids required. If desired, analysis to confirm correct sequences in the constructed plasmids is performed in a known fashion. Suitable methods for constructing expression vectors, preparing in vitro transcripts, introducing DNA into host cells, and performing analyses for assessing expression of the DNA of the invention and function are known to those skilled in the art. DNA presence, amplification and/or expression may be measured in a sample directly, for example, by conventional Southern blotting, Northern blotting to quantitate the transcription of mRNA, dot blotting (DNA or RNA analysis), or in situ hybridization, using an appropriately labelled probe based on a sequence provided herein.

In accordance with another embodiment of the present invention, there are provided cells containing the above-described nucleic acids (i.e., DNA or mRNA). Such host cells such as prokaryote, yeast and higher eukaryote cells may be used for replicating DNA and producing the multidomain protein of the invention. Suitable prokaryotes include eubacteria, such as Gram-negative or Gram-positive organisms, such as *E. coli*, e.g. *E. coli* K-12 strains, DH5a, HB101 and XL1 Blue or Bacilli. Further hosts suitable for multidomain protein encoding vectors include eukaryotic microbes such as filamentous fungi or yeast, e.g. *Saccharomyces cerevisiae*. Higher eukaryotic cells include insect and vertebrate cells, particularly mammalian cells. In recent years propagation of vertebrate cells in culture (tissue culture) has become a routine procedure. The host cells referred to in this disclosure comprise cells in in vitro culture as well as cells that are within a host animal.

DNA may be stably incorporated into cells or may be transiently expressed using methods known in the art. Stably transfected mammalian cells may be prepared by transfecting cells with an expression vector having a selectable marker gene, and growing the transfected cells under conditions selective for cells expressing the marker gene. To prepare transient transfectants, mammalian cells are transfected with a reporter gene to monitor transfection efficiency.

To produce such stably or transiently transfected cells, the cells should be transfected with an amount of protein-encoding nucleic acid sufficient to form the multidomain protein of the invention.

Host cells are transfected or transformed with the above-captioned expression or cloning vectors of this invention and cultured in conventional nutrient media modified as appropriate for inducing promoters, selecting transformants, or amplifying the genes encoding the desired sequences. Heterologous DNA may be introduced into host cells by any method known in the art, such as transfection with a vector encoding a heterologous DNA by the calcium phosphate coprecipitation technique or by electroporation. Numerous methods of transfection are known to the skilled worker in the field. Successful transfection is generally recognized when any indication of the operation of this vector occurs in the host cell. Transformation is achieved using standard techniques appropriate to the particular host cells used.

Incorporation of cloned DNA into a suitable expression vector, transfection of eukaryotic cells with a plasmid vector or a combination of plasmid vectors, each encoding one or more distinct genes or with linear DNA, and selection of transfected cells are well known in the art (see, e.g. Sambrook et al. (1989) Molecular Cloning: A Laboratory Manual, Second Edition, Cold Spring Harbor Laboratory Press).

Transfected or transformed cells are cultured using media and culturing methods known in the art, preferably under conditions, whereby multidomain protein encoded by the DNA is expressed. The composition of suitable media is known to those in the art, so that they can be readily prepared. Suitable culturing media are also commercially available.

Within the present invention an effector nucleic acid comprises a desired nucleic acid, which may be e.g. a therapeutically active nucleic acid or a reporter gene, and a specific nucleic acid sequence (also referred to as nucleic acid recognition sequence or cognate structure) recognizable by the nucleic acid binding domain of the multi-domain fusion protein, and, if needed, suitable regulatory elements for the expression of the desired nucleic acid. If required, an effector nucleic acid suitable as a component in the complex of the invention is capable of directing the expression of the desired nucleic acid to be delivered to the target cell. A therapeutically active nucleic acid desired to be delivered to the target cell by the transfer system of the invention may be therapeutically active itself, e.g. by selectively affecting a predetermined process within the target cell, e.g. inhibit sythesis of a particular protein, or it may code for a therapeutically active gene product to be expressed in the target cell. For example, such a gene product may be a new or modified gene, e.g. a tumor suppressor gene or an antibody gene for intracellular immunization, a nucleic acid coding for a prodrug activating enzyme, e.g. herpex simplex thymidine kinase, a nucleic acid coding for animmunmodulator or a foreign antigen, which is suitable for "alienating" the target cell.

The cognate structure may be an RNA or, preferably, a DNA. The effector nucleic acid may comprise one or more, preferably 2 to 8, nucleic acid recognition sequences. If two or more such sequences are present on an effector nucleic acid, advantageously these are arranged in a way to avoid sterically hindrance of the binding of the multidomain protein of the invention. Prefered is an effector nucleic acid comprising one or more copies, particularly two copies, of the above identified GAL4 recognition sequence. Said sequence binds protein dimers.

Typically, the nucleic acid desired to be expressed in the target cell is a gene, generally in the form of DNA, which encodes a desired protein, e.g. a therapeutically active protein. The gene comprises a structural gene encoding the protein, e.g. an immunmodulatory protein, in a form suitable for processing and secretion as a soluble or cell surface protein by the target cell. For example, the gene encodes appropriate signal sequences which direct processing and secretion of the protein or polypeptide. The signal sequence may be the natural sequence of the protein or an exogennous sequence. The structural gene is linked to appropriate genetic regulatory elements required for expression of the gene-encoded protein or polypeptide by the target cell. These include a promoter and optionally an enhancer element operable in the target cell. The gene can be contained in an expression vector, such as a plasmid or a transposable genetic element, also with the genetic regulatory elements necessary for expression of the gene and secretion of the gene-encoded product. For example, a component of the nucleic acid delivery system of the invention may be a eukaryotic expression plasmid, e.g. a plasmid comprising DNA coding for chloramphenicol acetyltransferase (CAT) driven by an SV40 promoter, e.g. plasmid pSV2 CAT. The effector nucleic acid may also be a linear DNA fragment.

The effector nucleic acid may comprise bacterial elements suitable for the selection and cloning of the vector.

Suitable eukaryotic expression plasmids or linear DNA fragments carry a promoter structure, the nucleic acid to be introduced and expressed in the target cell, eukaryotic splice and polyadenylation signals, and a specific DNA sequence recognized by the DNA binding domain of the multi-domain fusion protein.

Exemplary genes to be expressed in the target cell also include reporter or marker genes, such as genes encoding luciferase or beta-galactosidase.

If required, the effector nucleic acid may comprise a eukaryotic splice signal or a polyadenylation signal.

The preparation of an effector nucleic acid according to the invention involves methods well known in the art, e.g. those referred to in more detail above.

The type and nature of the nucleic acid to be introduced into the target cell is determined by the effect envisaged to be achieved said target cell, e.g. in case of use in gene therapy by the gene or gene section to be expressed to replace a defective gene, or by the target sequence of a gene the expression of which is to be inhibited. The nucleic acid to be delivered into the cell may be a DNA or a RNA, with no restrictions to the sequence of said nucleic acid.

If the system of the invention is applied to tumor cells to be employed as tumor vaccines, the DNA to be introduced into the cell preferably codes for an immunomodulating protein, e.g. a cytokine or a cell surface antigen suitable for activating a immune response. Combinations of DNAs coding for cytokines, e.g. IL-2 and IFN-g, B7.1, B7.2, MHC1 or MHC2 are considered particularly useful.

If desired, two or more different nucleic acids may be introduced into the cell, e.g. a plasmid comprising cDNAs coding for different proteins, under control of suitable regulatory sequences, or two different plasmids comprising different cDNAs.

The present invention provides means for directing or enhancing the expression of desired proteins (or RNA) in target cells, transgenic animals or insects. The multidomain protein or the protein/nucleic acid complex of the invention is used to introduce nucleic acid into eukaryotic cells, particularly higher eukaryotic cells. Preferred is the use for transfection of mammalian, particularly human cells, e.g. tumor cells, myoblasts, fibroblasts, hepatocytes, endothelial cells or respiratory tract cells. The nucleic acid transfer system of the present invention is useful for the selective DNA transfer into target cells for in vitro applications such as determine the immune response to a particular antigen, and ex vivo or in vivo gene therapy protocols for the therapeutical or prophylactical treatment of mammals in need thereof, particularly humans. Such mammals include those suffering e.g. from inherited or acquired diseases, such as genetic defects, e.g. cystic fibrosis (cystic fibrosis transmembrane conductance gene), hypercholestemia (low density lipoprotein (LDL) receptor gene, b-thalassemia, cancerous, autoimmune or infectious diseases. Ex vivo or in vivo application of the protein/nucleic acid complex of the present invention may result in prevention, stabilization or reversion of diseases such as HIV, melanoma, diabetes, Alzheimer disease or heart diseases. According to the invention treatment of cancer may be accomplished by blockade of oncogene expression with antisense constructs, by the introduction and expression of tumor suppressor genes, prodrug activating enzymes or toxic effectors, by administration of tumor vaccines or intracellular immunization. If appropriate, the nucleic acid transfer system of the present invention is applied in combination wit a polycation, such as polylysine, polyarginine or polyornithine, a heterologous polycation comprising two or more different, positively charged amino acid, non-peptidic synthetic polycations, e.g. polyethyleneimine, a protamine, or a histone. Advantageously, the polycation is added after the formation of the protein/nucleic acid complex of the invention, but before the application thereof.

The nucleic acid transfer system of the invention may also be used for immune regulation in organisms, particularly vaccination, or for the production of antibodies for experimental, diagnostic or therapeutic use. For the purpose of vaccination the effector nucleic acid component of the complex of the invention comprises an expressible gene encoding a desired immunogenic protein or peptide, which preferably has a costimulatory effect. The gene is incorporated into the target cell, expressed and following secretion of the gene product as a soluble protein or a cell surface protein an immune response against the immunogenic protein or peptide, such as all or part of the hepatitis B or C antigen, is elicited in the host organism. If the protein against which the immune response is desired is non- or poorly immnunogenic, the protein may be coupled to a carrier protein providing for sufficient immunogenicity. This is accomplished by recombinant means by preparing a chimeric DNA construct encoding a fusion protein comprising the protein of the invention and the carrier.

In accordance with the above description, the invention provides a method for stimulating antigen-specific T cells and/or B cells, whereby T cell receptors of said T cells specifically recognize an immunogenic protein or peptide and/or B cells produce antibodies specifically recognizing an immunogenic protein or peptide. Said method comprises administering to the host organism a protein/nucleic acid complex comprising a) a multidomain protein comprising a target cell-specific binding domain, a translocation domain and a nucleic acid binding domain, wherein the translocation domain is derivable from a bacterial toxin and wherein said translocation domain does not include the cytotoxic part of said bacterial toxin, and b) an effector nucleic acid, wherein said effector nucleic acid encodes the immunogenic protein or peptide.

The introduction of genes into target cells with the aim of accomplishing in vivo synthesis of therapeutically effective gene products, e.g. in case of a genetic deficiency to make up for the deficient gene, may also be accomplished using the nucleic acid transfer system of the invention. Apart from "conventional" gene therapy concepts which aim at achieving long-term success of treatment following a one time treatment the present invention provides means for the single or multiple administration of a therapeutically efficient nucleic acid like a pharmaceutical ("gene pharmaceutical"). The nucleic acid transfer system of the present invention may also be useful for transient gene therapy (TGT), preferably for transfer of a recombinant antigen receptor into lymphocytes (especially CTLs). If desired, a constant expression level of transferred genes may be maintained by repeated application of the protein/DNA complex of the invention.

The invention also provides a pharmaceutical composition comprising as effective component a protein/nucleic acid complex of the invention and a pharmaceutically acceptable carrier. Said complex comprises a therapeutically effective nucleic acid, advantageously as a component of a gene construct. In a preferred embodiment the pharmaceutical composition is provided as a lyophilisate or frozen in a suitable buffer. A pharmaceutically acceptable carrier is any carrier in which the protein/nucleic acid complex can be solubilized such that it can be used according to the invention. A pharmaceutical composition of the invention may additionally comprise an above identified polycation.

Furthermore, the invention provides a transfection kit comprising a carrier, container or vial comprising the protein/nucleic acid complex of the invention and further materials needed for the transfection of higher eukaryotic cells according to the invention. In said kit, the two components of the complex may be stored together or separately, depending on the intended use and the stability of the complex. If stored separately, the two components of the protein/nucleic acid complex of the invention may be mixed immediately before the complex is used.

In vivo therapeutic administration may be via a systemic route, transdermal application, e.g. as an aerosol formulation, and intravenous injection being preferred. Target organs for such applications include liver, spleen, lung, bone marrow and tumors.

Administration for therapeutic purposes may also occur ex vivo involving removal of suitable cells from the patient or another subject, culturing and treatment of the cells with the protein/nucleic acid complex of the invention under conditions allowing internalization of said complex, and subsequent (re-) administration of the treated cells to the patient. Cells suitable for such ex vivo treatment include bone marrow cells, hepatocytes or myeloblasts. Ex vivo treatment is also possible for cancer vaccines. A therapeutic treatment involving cancer vaccines comprises transfection of tumor cells isolated from a patient with a nucleic acid coding for a cytokine and subsequent readministration of the transfected cells producing the cytokine.

In another aspect, the invention relates to a method for the delivery of a nucleic acid into a target cell, particularly a higher eukaryotic cell, said method comprising exposing the cells to the protein/nucleic acid delivery system of the invention in such a way that the complex is internalized and liberated from the endosomes.

The invention particularly relates to the specific embodiments as described in the Examples which serve to illustrate the present invention but should not be construed as a limitation thereof Abbreviations: Pseudomonas aeruginosa exotoxin A=ETA; GAL4=Galactose gene cluster gene 4; DTT=dithiothreitol; aa=amino acids.

EXAMPLE 1

Cloning of the *Pseudomonas aeruginosa* Exotoxin A Gene Fragment Encoding Amino Acids 252 to 366

1.1 Derivation of DNA Fragments and Purification

Plasmid pWW20 (Wels et al., Cancer Res. 52: 6310, 1992) carries a truncated ETA gene encoding amino acids 252 to 613 of exotoxin A from *Pseudomonas aeruginosa* PAK (Gray et al., Proc. Natl. Acad. Sci. USA 81: 2645, 1984; Lory et al., J. Bacteriol. 170: 714, 1989). This gene contains domains II and III, the translocation and ADP-ribosylation domains, respectively, of the wild-type toxin. pWW20 (1 mg) is digested with XbaI and XbbI. DNA fragments are separated on a 1.0% (w/v) agarose gel (ultra pure agarose, BRL) and the expected 769 bp XbaI/XhoI DNA fragment encoding ETA amino acids 252 to 506 is eluted using the QIAquick gel extraction kit (QIAGEN) according to procedures provided by the manufacturer. The eluted fragment is subsequently digested with MaeII, DNA fragments are separated on a 1.5% (w/v) agarose gel and the expected 349 bp XbaI/MaeII DNA fragment encoding ETA amino acids 252 to 366 (designated DETA) is eluted as described above.

1.2 Oligonucleotides

A double stranded DNA adaptor with MaeII and EcoRI compatible ends is constructed by annealing 0.5 nmol of the oligonucleotide having the sequence set forth in SEQ ID NO. 7) with 0.5 nmol of the oligonucleotide having the sequence set forth in SEQ ID NO. 8 by incubation at 65° C. for 3 min and cooling to room temperature. The sequence of the partially double stranded MaeII/EcoRI adaptor oligonucleotide is

```
            10         20         30         40
5'- CGAGAAGCTT GAGAGCTCTG ACTACAAAGA CGAACTTTAAG..... -3'

3'- ..TCTTCGAA CTCTCGAGAC TGATGTTTCT GCTTGAAATT CTTAA -5.
```

Bp 1 to 2 represent the MaeII compatible overhanging end, bp 5 to 10 a HindIII restriction site, bp 13 to 18 a SacI restriction site, and bp 42 to 45 the EcoRl compatible overhanging end.

1.3 Ligation

Plasmid pWW191 is a pUC19 derived plasmid wherein the original HindIII restriction site of the multiple cloning site of pUC19 is destroyed and converted into a XbaI restriction site. pWW191 (50 ng) is digested with XbaI and EcoRI and 30 ng of purified DETA fragment (see Example 1.1), and 20 pmol MaeII/EcoRI oligonucleotide adaptor are ligated using 0.5 U T4 DNA ligase (New England Biolabs) in 50 mM Tris-HCl, pH 7.8, 10 mM magnesium chloride, 10 mM DTT, and 0.8 mM ATP overnight at 16° C. One half of ligation mixture is used to transform *E.coli* XL1 Blue (Stratagene) to obtain ampicillin resistant colonies. These are screened for the desired ligation product using a NaOH based plasmid "miniprep" method (Maniatis et al., Molecular Cloning: A Laboratory Manual/Second Edition, Cold Spring Harbor Laboratory, 1989). The obtained plasmid is designated pWW25. The partial DNA sequence of pWW25 encoding modified exotoxin A from *P. aeruginosa* is shown in SEQ ID NO. 9. Said DNA sequence has the following features:

| | |
|---|---|
| from 1 to 4 bp | synthetic spacer |
| from 5 to 349 bp | encoding aa 252 to 366 of *P. aeruginosa* exotoxin A (DETA) |
| from 349 to 393 bp | synthetic MaeII/EcoRI adaptor |
| from 386 to 388 bp | ochre stop codon |
| from 389 to 394 bp | non-coding synthetic spacer. |

EXAMPLE 2

Cloning of the Yeast Transcription Factor GAL4 Gene Fragment Encoding Amino Acids 2 to 147

Plasmid p02G2A (Yang et al., EMBO J. 10: 2291, 1991) which contains a GAL4 gene fragment encoding amino acids 1 to 147 of GAL4 (Laughon and Gesteland, Mol. Cell. Biol. 4: 260, 1984) is used as a template in a polymerase chain reaction to amplify a GAL4 DNA fragment encoding amino acids 2 to 147 (designated DGAL4).

2.1 Polymerase Chain Reaction 12 ng of p02G2A (Yang et al., EMBO J. 10: 2291, 1991) is used for DNA amplification in a 50 ml reaction containing 50 pmol each of the two oligonucleotides complementary to regions in the yeast GAL4 gene 5'-CAGATGAAGCTTCTGTCTTC-3' (SEQ ID NO. 10) and 5'-GAATGAGCTCGATACAGTCAACTG-3' (SEQ ID NO. 11), 4 ml 2.5 mM dNTP (N=G, A, T, C) mixture, 5 ml 10× Taq DNA polymerase buffer (Boehringer Mannheim) and 2.5 U of Taq DNA polymerase (Boehringer Mannheim). Taq DNA polymerase is added after initial denaturation at 94° C. for 2 min. For 30 cycles annealing is performed for 1 min at 55° C., primer extension for 1 min at 72° C., denaturation for 1 min at 94° C. Finally, amplification is completed by a 3 min primer extension step at 72° C.

2.2 Derivation of the GAL4 DNA Fragment and Purification

Amplification products are separated on a 1.2% (w/v) agarose gel (ultra pure agarose, BRL), DNA of the expected size is eluted, and subsequently digested with HindIII and SacI. The expected 441 bp DGAL4 DNA fragment encoding amino acids 2 to 147 of GAL4 is separated on a 1.2% agarose gel and purified by elution from the gel as described above.

2.3 Ligation pWW25 (50 ng) digested with HindIII and SacI, and 30 ng of purified amplification product are ligated using 0.5 U T4 DNA ligase (New England Biolabs) in 50 mM Tris-HCl, pH 7.8, 10 mM magnesium chloride, 10 mM DTT, and 0.8 mM ATP overnight at 16° C. One half of ligation mixture is used to transform *E.coli* XL1 Blue (Stratagene) to obtain ampicillin resistant colonies. These are screened for the desired ligation product using a NaOH based plasmid "miniprep" method (Maniatis et al., Molecular Cloning: A Laboratory Manual/Second Edition, Cold Spring Harbor Laboratory, 1989). The obtained plasmid is designated pWW35. The partial DNA sequence of pWW35 encoding partial GAL4 from yeast is shown in SEQ ID NO: 12. The features of said sequence are as follows.

| | |
|---|---|
| from 1 to 438 bp | encoding amino acids 2 to 147 of yeast GAL4 |
| from 439 to 443 bp | synthetic spacer. |

EXAMPLE 3
Isolation of RNA from the Hybridoma Cell Line FRP5

3.1 Growth of FRP5 Cells

FRP5 hybridoma cells ($1\times10^8$; deposited under the Budapest Treaty on Nov. 21, 1990 at the European Collection of Animal Cell Cultures (ECACC) in Porton Down, Salibury, UK, under accession number 90112115) are grown in suspension culture at 37° C. in DMEM (Seromed) further containing 10% FCS (Amimed), 1 mM sodium pyruvate (Seromed), 2 mM glutamine (Seromed), 50 mM 2-mercaptoethanol and 100 mg/ml of gentamycin (Seromed) in a humidified atmosphere of air and 7.5% $CO_2$ in 175 cm tissue culture flasks (Falcon 3028). The cells are harvested by centrifugation, washed once in PBS, flash frozen in liquid nitrogen and kept frozen as a pellet at –80° C. in a clean, sterile plastic capped tube.

3.2 Extraction of Total Cellular RNA from FRP5 Cells

Total RNA is extracted using the acid guanidinium thiocyanate-phenol-chloroform method described by Chomczynski & Sacchi (Anal. Biochem. 162: 156, 1987). Cell pellets of FRP5 cells ($1\times10^8$) are thawed directly in the tube in the presence of 10 ml of denaturing solution (4 M guanidinium thiocyanate (Fluka), 25 mM sodium citrate, pH 7.0, 0.5% N-lauroylsarcosine (Sigma), 0.1M 2-mercaptoethanol). The solution is homogenized at room temperature. Sequentially, 1 ml of 2 M sodium acetate, pH 4, 10 ml of phenol (water saturated) and 2 ml of chloroform-isoamyl alcohol mixture (49:1) are added to the homogenate. The final suspension is shaken vigorously for 10 sec and cooled on ice for 15 min. The samples are centrifuged at 10,000×g for 20 min at 4° C. After centrifugation, RNA which is present in the aqueous phase is mixed with 10 ml of isopropanol and placed at –20° C. for 1 h. The RNA precipitate is collected by centrifugation, the pellet dissolved in 3 ml water and the RNA reprecipitated by addition of 1 volume of isopropanol at –20° C. After centrinugation and washing the pellet in ethanol, the final pellet of RNA is dissolved in water. The method yields approximately 300 mg of total cellular RNA. The final purified material is stored frozen at –20° C.

3.3 Isolation of Poly(A) Containing RNA

Poly(A) containing RNA is selected from total RNA by chromatography on oligo(dT)-cellulose (Boehringer Mannheim) as described originally by Edmonds et al. (Proc. Natl. Acad. Sci. USA 68: 1336, 1971) and modified by Maniatis et al. (Molecular Cloning: A Laboratory Manual, Cold Spring Harbor Laboratory, 1982, p. 197). The poly(A)-containing RNA is prepared as described in the published procedure with the exception that the RNA is eluted from the oligo(dT)-cellulose with water rather than SDS-containing buffer. The poly(A)-containing RNA is precipitated with ethanol and collected by centrifugation. The yield of poly (A)-containing RNA is approximately 30 mg from 300 mg of total cellular RNA. The final purified material is stored frozen at –20° C.

EXAMPLE 4
Cloning of Functional Heavy and Light Chain Rearrangements from the FRP5 Hybridoma Cell Line Poly(A)-containing RNA isolated from FRP5 hybridoma cells as described in Example 3.3 provides the source for cDNA synthesis and subsequent amplification of V-region minigenes. Amplification products of the expected size are purified from agarose gels and cloned into appropriate vectors. Functional rearrangements are identified by sequencing.

4.1 Oligonucleotides

Oligonucleotide MCK2 is designed to be complementary to a region in the murine immunoglobulin k (kappa) constant minigene and has the nucleotide sequence set forth in SEQ ID NO. 13. Oligonucleotide MCHC2 is designed to be complementary to a region in the murine immunoglobulin g1 constant minigene and and has the nucleotide sequence set forth in SEQ ID NO. 14. The oligonucleotides VH1FOR, VH1BACK, and VK1BACK are designed by Orlandi et al. (Proc. Natl. Acad. Sci. USA 86: 3833, 1989) to match consensus sequences.

```
VH1FOR:  5' - TGAGGAGACGGTGACCGTGGTCCCTTGGCCCCAG - 3'         (SEQ ID NO:56)

VH1BACK: 5' - AGGT (C/G) (C/A) A (G/A) CTGCAG (G/C) AGTC (T/A) GG - 3'    (SEQ ID NO:57)

VK1BACK: 5' - GACATTCAGCTGACCCAGTCTCCA - 3'                    (SEQ ID NO:58)
```

4.2 cDNA Synthesis 55 ng of poly(A)-containing RNA is dissolved in a buffer containing 50 mM Tris-HCl, pH 8.3, 3 mM magnesium chloride, 10 mM DTT, 75 mM KCl, 400 mM dNTPs (N=G, A, T and C), 100 mg BSA (molecular biology grade, Boehringer Mannheim), 100 U RNAse inhibitor (Boehringer Mannheim), 25 pmol MCK2 and 25 pmol MCHC2. The RNA is denatured at 70° C. for 5 min and then chilled on ice for 2 min. After addition of 200 U of MMLV reverse transcriptase (Gibco, BRL) cDNA synthesis is achieved by incubation for 1 h at 37° C.

4.3 Polymerase Chain Reaction

One tenth of the cDNA reaction is used for DNA amplification in buffer containing 10 mM Tris-HCl, pH 8.3, 1.5 mM $MgCl_2$, 50 mM KCl, 10 mM b-mercaptoethanol, 200 mM dNTPs (N=G, A, T and C), 0.05% Tween-20% (Merck), 0.05% NP-40% (Merck), 10% DMSO (Merck), 25 pmol oligonucleotide 1 (see below), 25 pmol oligonucleotide 2 (see below) and 2.5 U Amplitaq% DNA polymerase (Perkin Elmer Cetus). Taq polymerase is added after initial denaturation at 93° C. for 1 min and subsequent annealing at 37° C. In the first 4 cycles primer extension is performed at 71° C. for 0.2 min, denaturation at 93° C. for 0.01 min and annealing at 37° C. for 0.2 min. For the last 25 cycles the annealing temperature is raised to 62° C. Finally, amplification is completed by a 3 min primer extension step at 71° C.

| PCR Product | oligonucleotid 1 | oligonucleotide 2 |
|---|---|---|
| H | VH1FOR | VH1BACK |
| LC | MCK2 | VK1BACK |

4.4 Modification and Purification

Amplified material is extracted with $CHCl_3$ and precipitated with ethanol in the presence of 200 mM LiCl. To facilitate cloning, blunt ends are created by a 3 min treatment with 1 U T4 DNA polymerase (Boehringer Mannheim) in 66 mM Tris-acetate, pH 7.9, 132 mM potassium acetate, 20 mM magnesium acetate, 1 mM DTT, 200 mg/ml BSA (molecular biology grade, Boehringer Mannheim), and 400 mM dNTPs (N=G, A, T and C). The polymerase is inactivated by heating for 15 min at 65° C. before phosphorylation of the DNA with 10 U T4 polynucleotide kinase (Pharmacia) at 37° C. for 1 h. For this purpose the buffer is adjusted to 50 mM EDTA and 1 mM ATP. The modified amplification products are separated on a 1.2% (w/v) agarose gel (ultra pure DNA grade agarose, Biorad) and DNA of the expected size is eluted by means of DEAE NA 45 membranes (Schleicher & Schuell).

4.5 Ligation

Bluescript% KS+ (70 ng) linearized with XbaI, treated with Klenow DNA polymerase (Boehringer Mannheim) to give blunt ends and dephosphorylated with calf intestinal phosphatase, and 30 ng of purified amplification product are ligated using 0.5 U T4 DNA ligase (New England Biolabs) in 50 mM Tris-HCl, pH 7.8, 10 mM magnesium chloride, 10 mM DTT, and 0.8 mM ATP overnight at 16° C. One half of the ligation mixture is used to transform E. coli K803 to obtain ampicillin resistant colonies. These are screened for the desired ligation products using a NaOH based plasmid "miniprep" method (Maniatis et al., Molecular Cloning: A Laboratory Manual, Cold Spring Harbor Laboratory, 1982). The following plasmids are obtained:

| PCR Product | Plasmid clones |
|---|---|
| H | pMZ16/1 |
| LC | pMZ18/1 |

4.6 Sequencing

Sequencing is done using Sequenase% kits (United States Biochemicals) with T3 and T7 oligonucleotide primers according to procedures provided by the manufacturer. Plasmid pMZ18/1 contains a functional FRP5 kappa light chain variable domain insert. Plasmid pMZ16/1 contains a functional FRP5 heavy chain variable domain insert. Plasmids pMZ16/1 and pMZ18/1 are used as a source for further subcloning steps.

EXAMPLE 5

Construction of the MAb FRP5 Single-chain Fv Gene 5.1 Construction and Sequence of a Cloning Linker for the Heavy and Light Chain Variable Domain cDNAs Using oligonucleotides, a linker sequence which allows the cloning of PCR amplified mouse heavy chain variable domain cDNA as a PstI/BstEII fragment and of PCR amplified mouse kappa light chain variable domain cDNA as a PvuII/BglII fragment is constructed as described by Wels et al., Biotechnology 10: 1128, 1992. This creates an open reading frame in which heavy and light chain variable domains are connected by a sequence coding for the 15 amino acid stretch Gly-Gly-Gly-Gly-Ser-Gly-Gly-Gly-Gly-Ser-Gly-Gly-Gly-Gly-Ser (SEQ ID NO:49). This amino acid linker has been shown to allow correct folding of an antigen binding domain present in heavy and light chain variable domains in a single-chain Fv (Huston et al., Proc. Natl. Acad. Sci. USA 85: 5879, 1988).

For the construction of the cloning linker the 6 complementary oligonucleotides 1A (SEQ ID NO. 15), 1B (SEQ ID NO. 16), 2A (SEQ ID NO. 17), 2B (SEQ ID NO. 18), 3A (SEQ ID NO. 19), 3B (SEQ ID NO. 20) are used.

40 pM of oligonucleotides 1B, 2A, 2B, 3A are phosphorylated at the 5' end using T4 polynucleotide kinase (Boehringer Mannheim) in four separate reactions in a total volume of 20 ml following the method described by Maniatis et al., supra. Oligonucleotides 1A and 3B are not phosphorylated in order to avoid self ligation of the linker in the final ligation reaction. After the kinase reaction, the enzyme is inactivated by incubation at 70° C. for 30min. In three separate reactions, each containing 40 pM of two oligonucleotides in a total volume of 40 ml, non-phosphorylated 1A and phosphorylated 1B, phosphorylated 2A and phosphorylated 2B, and phosphorylated 3A and non-phosphorylated 3B are mixed. Hybridization of the oligonucleotides in the three reactions is carried out by heating to 95° C. for 5 min, incubation at 65° C. for 5 min and slowly cooling to room temperature. 10 ml from each of the three reactions are mixed, 4 ml of 10×ligation buffer (Boehringer) and 4 units of T4 DNA ligase (Boehringer) are added and the total volume is adjusted to 40 ml with sterile water. The annealed pairs of oligonucleotides are ligated into one linker sequence for 16 h at 14° C. The reaction mixture is extracted with an equal volume of phenol/chloroform (1:1) followed by re-extraction of the aqueous phase with an equal volume of chloroform/isoamyl alcohol (24:1). The aqueous phase is collected, 0.1 volumes of 3 M sodium acetate pH 4.8 and 2 volumes of ethanol are added, and the DNA is precipitated at −70° C. for 4 h and collected by centrifugation. The resulting linker sequence has a SphI and a XbaI adaptor end. It is ligated to SphI and XbaI digested pUC19 in a reaction containing 100 ng of ligated linker and 200 ng of SphI/XbaI digested pUC19. After transformation into E. coli XL1 Blue% (Stratagene), plasmid DNA from 4independent colonies is isolated by the alkaline lysis mini-preparations method (Maniatis et al., Molecular Cloning: A Laboratory Manual, Cold Spring Harbor Laboratory, 1982). The DNA sequence of the linker cloned in pUC19 is determined by sequencing double stranded DNA in both directions with Sequenase II (United States Biochemicals) and pUC universal and reverse primers (Boehringer) following the manufacturer's protocol. Three out of the four recombinant pUC19 isolates sequenced contain the correct linker sequence. One of them is designated pWW19 and used in the further experiments. The partial DNA sequence of pWW19 which is set forth in SEQ ID NO. 21 has the following features:

| | |
|---|---|
| from 30 to 35 bp | PstI site |
| from 38 to 44 bp | BstEII site for subcloning of heavy chain variable domain |
| from 54 to 98 bp | coding sequence of (GlyGlyGlyGlySer)₃ linker |
| from 105 to 110 bp | PvuII site |
| from 112 to 117 bp | BglII site |
| from 120 to 125 bp | BclI site for subcloning of light chain variable domain |

5.2 Preparation of a Plasmid for the Subcloning of Variable Domains

The Fv cloning linker sequence is derived as a 144 bp HindIII/SacI fragment from pWW19 and inserted into HindIII/SacI digested Bluescript% KS+ (ex PvuII) (Stratagene) which contains no PvuII restriction sites. The resulting plasmid, pWW15, allows cloning of heavy and light chain variable domains as PstI/BstEII and PvuII/BglII fragments, respectively.

5.2.1 Subcloning of the FRP5 Heavy Chain Variable Domain

Plasmid pMZ16/1 is digested with PstI and BstEII and the 338 bp heavy chain variable domain fragment of FRP5 is isolated. It is cloned into PstI/BstEII digested pWW19 yielding the plasmid pWW31.

5.2.2 Mutation of the FRP5 Light Chain Variable Domain and Assembly of the Fv Fusion Gene To facilitate subcloning of the FRP5 light chain variable domain into the Fv cloning linker, a PvuII restriction site and a BglII restriction site are introduced at the 5' and 3' ends, respectively, of the coding region. The FRP5 light chain variable domain coding region is isolated as a SacI/BamHI fragment from pMZ18/1. SacI and BamHI are restriction sites of the Bluescript% polylinker present in pMZ18/1. The fragment contains the complete light chain variable domain fragment of 392 bp amplified by PCR using the oligonucleotide MCK2 (see above). This fragment is mutated and amplified by PCR using the oligonucleotides $V_L 5'$: 5 -GACATTCAGCTGACCCAG-3' (SEQ ID NO. 22) and $V_L 3'$:
5'-GCCCGTTAGATCTCCAATTTTGTCCCCGAG-3' (SEQ ID NO. 23)

for the introduction of a PvuII restriction site at the 5' end ($V_L 5'$) and a BglII restriction site at the 3' end ($V_L 3'$) of the kappa light chain variable domain DNA. 20 ng of the FRP5 variable light chain SacI/BamHI fragment are used as a template in a 100 ml reaction following the PCR conditions described in Example 4.3. The amplified and mutated fragment is isolated after PvuI/BglII digestion as a 309 bp fragment from a 1.5% agarose gel and cloned into PvuII/BglII digested pWW15 generating plasmid pWW41. The FRP5 kappa light chain variable domain is isolated as a BstEII/XbaI fragment from pWW41 and inserted into BstEII/XbaI digested pWW31. Thus the FRP5 heavy chain variable domain in pWW31 and the FRP5 kappa light chain variable domain are fused to one open reading frame. Double stranded DNA of three independent clones is sequenced with Sequenase II% kit (United Biochemicals) in both orientations using pUC universal and reverse primers (Boehringer) following the manufacturer's protocol. One of the plasmids carrying the FRP5 heavy chain variable domain fused to the mutated FRP5 light chain variable domain is selected and designated pWW52.

5.3 Mutation of the Single-chain Fv(FRP5) Gene

To allow gene fusion with the single-chain Fv(FRFP5) encoding gene from pWW52 a stop codon at sequence the 3' end position in pWW52 is deleted as follows: plasmid DNA of pWW52 is digested with BstEII and BglII and the linker sequence and FRP5 light chain variable domain encoding fragment is isolated. In another digestion, pWW52 is cleaved with BstEII and BclI. Thus, the large fragment containing vector sequences and the FRP5 heavy chain variable domain encoding sequence is isolated. The BstEII/BglII $V_L$ fragment is now inserted into BstEII/BclI cleaved pWW52 containing $V_H$. In the resulting plasinid, pWW53, the BglII/BclI junction is determined by sequencing double stranded DNA as described above (SEQ ID NO. 24).

EXAMPLE 6

Construction of Plasmid pWW152-5

6.1 Oligonucleotides

A double stranded DNA adaptor with HindIII and PstI compatible ends is constructed by annealing 0.5 nmol of the oligonucleotide having the sequence set forth in SEQ ID NO. 25 with 0.5 nmol of the oligonucleotide having the sequence set forth in SEQ ID NO. 26 by incubation at 65° C. for 3 min and cooling to room temperature. The structure of the oligonucleotide adaptor is:

5'-.AGCTTCAGGTACAACTGCA.-3'
3'-. . . AGTCCATGTTG . . . - 5'.

6.2 Derivation of pWW15 Vector Fragment and Purification

Plasmid pWW 15 (1 mg; see Example 5.2) is digested with HindIII and PstI. DNA fragments are separated on a 1.0% (w/v) agarose gel (ultra pure agarose, BRL) and the expected 3.1 kb HindIII/PstI vector fragment is eluted.

6.3 Ligation of pWW15 HindIII/PstI Fragment and Oligonucleotide Adaptor pWW15 (50 ng) HindIII/PstI fragment and 50 pmol oligonucleotide adaptor are ligated using 0.5 U T4 DNA ligase (New England Biolabs) in 50 mM Tris-HCl, pH 7.8, 10 mM magnesium chloride, 10 mM DTT, and 0.8 mM ATP overnight at 16° C. One half of ligation mixture is used to transform E. coli XL1 Blue (Stratagene) to obtain ampicillin resistant colonies. These are screened for the desired ligation product using a NaOH based plasmid "miniprep" method. The obtained plasmid is designated pWW152.

6.4 Derivation of DNA Fragments and Purification

Plasmid pWW152 (1 mg) is digested with PstI and XbaI. DNA fragments are separated on a 1.0% (w/v) agarose gel (ultr pure agarose, BRL) and the expected 3.1 kb PstI/XbaI vector fragment is eluted. Plasmid pWW53 (1 mg) is digested with PstI and XbaI. DNA fragments are separated and the PstI/XbaI DNA fragment encoding scFv(FRP5) is eluted as described above.

6.5 Ligation of pWW152 Vector Fragment and the scFv (FRP5) Gene Fragment

Plasmid pWW 152 (50 ng) digested with PStI and XbaI, and 30 ng of purified PstI/XbaI scFv(FRP5) fragment are ligated using 0.5 U T4 DNA ligase (New England Biolabs) in 50 mM Tris-HCl, pH 7.8, 10 mM magnesium chloride, 10 mM DTT, and 0.8 mM ATP overnight at 16° C. One half of the ligation mixture is used to transform E. coli XL1 Blue (Stratagene) to obtain ampicillin resistant colonies. These are screened for the desired ligation product using a NaOH based plasmid "miniprep" method. The obtained plasmid is designated pWW 152-5. The DNA sequence of the scFv (FRP5) gene between the HindIII and XbaI restriction site is identical to the sequence of plasmid pWF46-5 (see Example 8.) from nucleotide position bp 109 to bp 845 shown in SEQ ID NO: 1.

EXAMPLE 7

Construction of the Single-chain Fv (FRP5)-DETA-DGAL4 Fusion Gene

7.1 Derivation of DNA Fragments and Purification pWW35 (1 mg) is digested with XbaI and EcoRI. DNA fragments are separated on a 1.0% (w/v) agarose gel (ultra pure agarose, BRL) and the expected 821 bp XbaI/EcoRI DNA fragment carrying the DETA-DGAL4 fusion gene and adjacent synthetic sequences is eluted. Plasmid pWW152-5 (1 mg) carrying the gene encoding the erbB-2 specific single-chain Fv (scFv) molecule scFv(FRP5) is digested with HindIII and XbaI. DNA fragments are separated and the expected 735 bp HindIII/XbaI DNA fragment carrying the scFv gene is eluted as described above.

7.2 Ligation pFLAG-1 (50 ng) (IBI Biochemicals) digested with HindIII and EcoRI, and 30 ng of purified HindIII/XbaI scFv (FRP5) fragment, and 30 ng of purified XbaI/EcoRI DETA-D GAL4 fragment are ligated using 0.5 U T4 DNA ligase (New England Biolabs) in 50 mM Tris-HCl, pH 7.8, 10 mM magnesium chloride, 10 mM DTT, and 0.8 mM ATP overnight at 16° C. One half of ligation mixture is used to transform E.coli XL1 Blue (Stratagene) to obtain ampicillin resistant colonies. These are screened for the desired ligation product using a NaOH based plasmid "miniprep" method. The obtained plasmid is designated pWF45-5.

EXAMPLE 8

Construction of an Expression Plasmid Carrying the scFv (FRP5 DETA-DGAL4 Fusion Gene 8.1 Derivation of DNA Fragments and Purification pWF45-5 (1 mg) is digested with HindIII and SalI. DNA fragments are separated on a 1.0% (w/v) agarose gel (ultra pure agarose, BRL) and the expected 907 bp HindIII/SalI DNA fragment carrying the scFv(FRP5)-DETA$_{252-308}$ (coding for ETA amino acids 252 to 308) fusion gene is eluted. pWF45-5 (1 mg) is digested with SalI and XbaI. DNA fragments are separated and the expected 655 bp SalI/XbaI DNA fragment encoding DETA$_{309-366}$-DGAL4 is eluted as described above.

8.2 Ligation

Plasmid pFLAG-1 is digested with HindIII and XbaI and a double-stranded DNA linker encoding 6 His residues at its 5' end and the original HindIII-, EcoRI- and Xba-restriction sites of pFLAG-1 at its 3' end are inserted 3' of the FLAG epitope. The resulting plasmid pSW50 (50 ng) digested with HindIII and XbaI, and 30 ng of purified HindIII/SalI scFv (FRP5)-DETA$_{252-308}$ fragment, and 30 ng of purified Sal/XbaI DETA$_{309-366}$-DGAL4 fragment are ligated using 0.5 U T4 DNA ligase (New England Biolabs) in 50 mM Tris-HCl, pH 7.8, 10 mM magnesium chloride, 10 mM DTT, and 0.8 mM ATP overnight at 16° C. One half of ligation mixture is used to transform E.coli XL1 Blue (Stratagene) to obtain ampicillin resistant colonies. These are screened for the desired ligation product using a NaOH based plasmid "miniprep" method (Maniatis et al., supra). The obtained plasmid is designated pWF46-5. The partial DNA sequence of pWF46-5 is shown in SEQ ID NO. 1. Said sequence has the following features:

| | |
|---|---|
| from 1 to 63 bp | encoding the E. coli ompA signal peptide |
| from 64 to 87 bp | encoding the synthetic FLAG epitope |
| from 88 to 114 bp | synthetic spacer sequence |
| from 115 to 834 bp | encoding scFv(FRP5) |
| from 835 to 843 bp | synthetic spacer sequence |
| from 844 to 1188 bp | encoding amino acids 252 to 366 of ETA |
| from 1189 to 1191 bp | synthetic spacer sequence |
| from 1192 to 1629 bp | encoding amino acids 2 to 147 of yeast GAL4 |
| from 1630 to 1653 bp | synthetic spacer including sequence coding for KDEL retention signal |
| from 1654 to 1656 bp | ochre stop codon |
| from 1657 to 1692 bp | non-coding synthetic spacer |

The deduced armino acid sequence of the pWF46-5 encoded scFv(FRP5)-DETA-DGAL4 protein including a peptide spacer a the N-terminus (aa 1 to 17) is shown in SEQ ID NO. 2.

EXAMPLE 9

Bacterial Expression and Purification of scFv(FRP5)-DETA-D GAL4

Plasmid pWF46-5 is transformed into E.coli K12. A recombinant single colony is grown overnight in 50 ml LB medium containing 100 μg/ml ampicillin and 0.6% glucose. The overnight culture is diluted 1:30 in 1 l fresh LB medium containing 100 μg/ml ampicillin and 0.6% glucose and grown at 37° C. to an OD$_{550}$ of 0.5. Isopropyl-beta-D-thiogalactopyranoside (IPTG) is added to a final concentration of 0.5 mM and expression is induced for 1.5 h at room temperature. The cells are harvested at 4° C. by centrifugation at 17,000 g for 10 min in a J2-HS centrifuge (Beckman) using a JA10 rotor (Beckman).

9.1 Isolation of scFv(FRP5)ΔETA-ΔGAL4 from the Bacterial Cell Pellet

The bacterial cell pellet is resuspended in 30 ml of lysis buffer containing 50 mM Tris-HCl, pH 8.0, 150 mM NaCl, 10 μM ZnCl$_2$, 0.3 mM PMSF, 8 M urea. The bacterial cells are lysed by sonication for 3 min on ice. The lysate is gently shaken for 1.5 h at room temperature and then centrifuged at 4° C. in a TL100 ultracentrifuge (Beckman) for 25 min at 100,000 g. The supernatant is collected, 10 mM imidazole final concentration is added and stored at 4° C.

9.2 Purification of scFv(FRP5)ΔETA-ΔGAL4 by Affinity Chromatography

A nickel-NTA affinity column (QIAGEN) is equilibrated in 50 mM Tris-HCl, pH 8.0, 150 mM NaCl, 10 μM ZnCl$_2$, 0.3 mM PMSF, 8 M urea, 10 mM imidazole. Cleared supernatant from step 9. 1 containing the scFv(FRP5)-ΔETA-ΔGAL4 protein is passed through the column. The column is washed with equilibration buffer. Bound protein is eluted with 250 mM imidazole in equilibration buffer. The eluate is first dialysed for 16 h at 4° C. against 60 volumes of 50 mM Tris-HCl, pH 8.0, 50 mM KCl, 5 mM MgCl$_2$, 10 μM ZnCl$_2$, 20% glycerol, 400 mM L-arginine. L-arginine is removed by a second dialysis for 16 h. at 4° C. against 60 volumes of the same dialysis buffer lacking the L-arginine. The dialysed protein solution is clarified at 4° C. by centrifugation at 23,000 g for 30 min in a J2-HS centrifuge (Beckman) using a JA20 rotor (Beckman). The supernatant is collected and stored at 4° C. Protein purity is detrmined by SDS-polyacrylamide gel electrophoresis in a 12.5% polyacrylamide gel. Typical protein purity after purification is greater than 90%.

EXAMPLE 10

Construction of Eukaryotic Expression Plasmids Containing GAL4 Recognition Sequences A family of plasmids each containing two GAL4 recognition sequences are constructed. The plasmids consist of a bacterial origin of replication, a bacterial selectable marker gene, and a eukaryotic expression unit with the following general structure:

eukaryotic promoter—gene of interest—intron—dimeric GAL4 recognition sequence—polyadenylation site 10.1 Oligonucleotides A double stranded DNA adaptor with HindIII and BamHI compatible ends is constructed by annealing 0.5 nmol of the oligonucleotide set forth in SEQ ID NO. 27 with 0.5 nmol of the oligonucleotide set forth in SEQ ID NO. 28 by incubation at 65° C. for 3 min and cooling to room temperature. The partially double stranded DNA oligonucleotide containing two GAL4 binding motifs is designated G4. The structure of the oligonucleotide adaptor is shown below:

```
         10        20        30        40        50
AGCTTGGATC CGGAGGACAG TCCTCCGGAG ACCGGAGGAC AGTCCTCC.. ..
....ACCTAG GCCTCCTGTC AGGAGGCCTC TGGCCTCCTG TCAGGAGGCT AG.
```

The features are as follows:

bp 1 to 4 HindIII compatible overhanging end; bp 6 to 11 BamH1 restriction site; bp 11 to 27 GAL4 binding motifI; bp 28 to 32 spacer sequence; bp 33 to 49 GAL4 binding motif II; bp 48 to 52 BamHI compatible overhanging end. Ligation of the BamHI compatible end to the BamHI site of a restriction fragment results in the destruction of that BamH1 restriction site.

10.2 Derivation of pSV2CAT DNA Fragments and Purification

Plasimid pSV2CAT (1 mg) (Gorman et al., Mol. Cell. Biol. 2: 1044, 1982) is digested with HindIII and BamHI. DNA fragments are separated on a 1.0% (w/v) agarose gel (ultra pure agarose, BRL) and the expected 3.4 kb HindIII/BamHI pSV2D vector fragment and the 1.6 kb HindIII/BamHI insert fragment carrying the chloramphenicol acetyl transferase (CAT) gene and adjacent vector sequences are eluted.

10.3 Ligation of pSV2D Fragment and Oligonucleotide Adaptor pSV2D (50 ng) HindIII/BamHI fragment and 50 pmol oligonucleotide adaptor are ligated using 0.5 U T4 DNA ligase (New England Biolabs) in 50 mM Tris-HCl, pH 7.8, 10 mM magnesium chloride, 10 mM DTT, and 0.8 mM ATP overnight at 16° C. One half of ligation mixture is used to transform E.coli XL1 Blue (Stratagene) to obtain ampicillin resistant colonies. These are screened for the desired ligation product using a NaOH based plasmid "miniprep" method (Maniatis et al., supra). The following plasmid is obtained: pSV2D-G4.

10.4 Ligation of pSV2D-G4 and CAT DNA Fragment pSV2D-G4 (50 ng) digested with HindIII and BamHI and 30 ng of the 1.6 kb HindIII/BamHI insert fragment from pSV2CAT carrying the chloramphenicol acetyl transferase (CAT) gene and adjacent vector sequences are ligated, the ligation mixture is transformed into E.coli and ligation products are screened as described in 10.3. The following plasmid is obtained: pSV2CAT-G4.

10.5 Derivation of the pSV2NEO DNA Fragment and Purification pSV2NEO (1 mg) (Southern & Berg, J. Mol. Appl. Genet. 1: 327, 1982) is digested with HindIII and BamHI. DNA fragments are separated on a 1.0% (w/v) agarose gel (ultra pure agarose, BRL) and the expected 2.3 kb HindIII/BamHI insert fragment carrying the neomycin phosphoribosyl transferase (NEO) gene and adjacent vector sequences is eluted.

10.6 Ligation of pSV2D-G4 and NEO DNA Fragment

Plasmid pSV2D-G4 (50 ng) digested with HindIII and BamHI and 30 ng of the 2.3 kb HindIII/BamHI insert fragment carrying the neomycin phosphoribosyl transferase (NEO) gene and adjacent vector sequences are ligated, the ligation mixture is transformed into E.coli, and ligation products are screened as described in 10.3. The following plasmid is obtained: pSV2NEO-G4.

10.7 Derivation of the pCH110 b-galactosidase DNA Fragment and Purification

Plasmid pCH110 (1 mg) (Pharmacia) is digested with HindIII and BamHI. DNA fragments are separated on a 1.0% (w/v) agarose gel (ultra pure agarose, BRL) and the expected 3.7 kb. HindII/BamHI insert fragment carrying the b-galactosidase gene and adjacent vector sequences is eluted.

10.8. Ligation of pSV2D-G4 and b-galactosidase DNA Fragment pSV2D-G4 (50 ng) digested with HindIII and BamHI and 30 ng of the 3.7 kb HindIII/BamHI insert fragment carrying the b-galactosidase gene and adjacent vector sequences are ligated, the ligation mixture is transformed into E.coli, and ligation products are screened as described in 6.3. The following plasmid is obtained: pSV2bGal-G4.

10.9 Ligation of pSV2D Fragment and b-galactosidase DNA Fragment pSV2D (50 ng) HindIII/BamHI fragment and 30 ng of the 3.7 kb HindIII/BamHI insert fragment carrying the b-galactosidase gene and adjacent vector sequences are ligated, the ligation mixture is transformed into E.coli, and ligation products are screened as described in 10.3. The following plasmid-is obtained: pSV2bGal.

10.10 Derivation of the pSVD5LUC Luciferase DNA Fragment and Purification pSVD5LUC (1 mg) (Gouilleux et al., Nuc. Acid Res. 19: 1563, 1991) is digested with HindIII and Bam-HI. DNA fragments are separated on a 1.0% (w/v) agarose gel (ultra pure agarose, BRL) and the expected 2.7 kb HindIII/BamHI insert fragment carrying the luciferase gene and adjacent vector sequences is eluted.

10.11 Ligation of pSV2D-G4 and Luciferase DNA Fragment pSV2D-G4 (50 ng) digested with HindIII and BamHI and 30 ng of the 2.7 kb HindII/BamHI insert fragment carrying the luciferase gene and adjacent vector sequences are ligated, the ligation mixture is transformed into E.coli, and ligation products are screened as described in 10.3. The following plasmid is obtained: pSV2LUC-G4.

10.12 Ligation of pSV2D Fragment and Luciferase DNA Fragment pSV2D (50 ng) HindIII/BamHI fragment and 30 ng of the 2.7 kb HindIII/BamHI insert fragment carrying the luciferase gene and adjacent vector sequences are ligated, the ligation mixture is transformed into E.coli, and ligation products are screened as described in 6.3. The following plasmid is obtained: pSV2LUC.

EXAMPLE 11

Determination of DNA Binding Activity of scFv(FRP5)-DETA-DGAL4 Protein

The DNA binding activity and specifity of the scFv (FRP5)-ETA-DGAL4 protein described in Example 9 is analyzed in gel retardation assays.

11.1 5'-DNA Labeling Reaction 5 pmol of G4 partially double stranded DNA oligonucleotide described in Example 6.1 containing 2 GAL4 binding motifs is incubated for 45 min at 37° C. with 50 mCi $(g-^{32}P)$ dATP (10 mCi/mi) (Amersham) and 10 U T4 polynucleotide kinase (Boehringer Mannheim) in a buffer containing 50 mM Tris-HCl, pH 7.6, 10 mM magnesium chloride, 5 mM DTT, and 0.1 mM EDTA. $^{32}$P-labeled G4 oligonucleotide is purified by extraction with 1 volume of a 1:1 mixture of Tris-HCl, pH 8.0 saturated phenol and chloroform/isoamyl alcohol (24:1) followed by extraction of the aqueous phase with 1 volume of chloroform/isoamyl alcohol (24:1) and precipitation of G4 oligonucleotide from the aqueous phase by the addition of 1 volume of 4 M ammonium acetate, 0.2 volumes of 1 M magnesium chloride and 2 volumes of ethanol at −20° C. overnight. The oligonucleotide pellet is dried under vacuum and the dry pellet is dissolved in water to a final concentration of 100 nM (1124 cpm/fmol).

11.2 Gel Retardation Assay 1 pmol scFv(FRP5)-DETA-DGAL4 protein and 50 fmol $^{32}$P-labeled G4 oligonucleotide are mixed in a 20 ml reaction in a buffer containing 50 mM Hepes, pH 7.5, 50 mM potassium chloride, 5 mM magnesium chloride, 10 mM zinc chloride, 6% glycerol, 200 mg/ml bovine serum albumin and 50 mg/ml poly-(dI-dC) (Boehringer Mannheim) and incubated for 30 min at room temperature. The samples are separated on a non-denaturating poly-acrylamide gel as described by Carey et al. (J. Mol. Biol. 209: 423, 1989). A 18×20 cm 4.5% acrylamide gel is prepared in a buffer at pH 8.4 containing 45 mM Tris-base, 45 mM boric acid, 1% glycerol. Samples are separated by electrophoresis for 2 to 3 h at 200 V with a running buffer at pH 8.4 containing 45 mM Tris-base, 45 mM boric acid, 1% glycerol. Bands are visualized by overnight exposure of the gel at −80° C. with X-OMAT DS film (Kodak). The intensity of bands is quantified using a FUJIX BAS1000 phosphorimager (Fuji). As a result of the gel retardation assay two bands with decreased mobility compared to the free probe are visible, the more intense higher molecular weight complex representing two scFv(FRP5)-DETA-DGAL4 dimers bound to the tandem GAL4 binding sites on the radioactive probe, the lower molecular weight complex representing one scFv(FRP5)-DETA-DGAL4 dimer bound to one of the tandem GAL4 binding sites on the radioactive probe. The unbound free probe is visible at the bottom of the gel.

11.3 Competition Assay

A gel retardation assay is performed exactly as described in Example 10.2 by incubating 1 pmol scFv(FRP5)-DETA-DGAL4 protein and 50 fmol $^{32}$P-labeled G4 oligonucleotide in the presence of increasing amounts from 50 fmol to 12.8 pmol of non-radioactive G4 oligonucleotide as a competitor resulting in G4/$^{32}$P-G4 ratios of 1, 4, 16, 64, 256. The results of the competition assay show that the binding of scFv (FRP5)-DETA-DGAL4 to the 32P-labeled G4 oligonucleotide is specific since increasing concentrations of the non-radioactive competitor reduce the amount of complex consisting of scFv(FRP5)-DETA-DGAL4 and 32P-labeled G4 oligonucleotide exponentially.

EXAMPLE 12

Determination of p185 erbB-2 Binding Specificity of scFv (FRP5)-DETA-DGAL4 Protein The p185 erbB-2 binding activity and specifity of the scFv(FRP5)-DETA-DGAL4 protein described in Example 9. is analyzed in an enzyme-linked immunosorbent assay (ELISA).

12.1 Preparation of ELISA Plates

SK-BR-3 human breast carcinoma cells (ATCC HTB30) are seeded in 96-well tissue culture plates at a density of 1×10$^5$ cells per well and grown for 24 h at 37° C. The cells are washed twice with PBS, fixed with 3.7% formaldehyde in PBS for 20 min at room temperature and blocked with a buffer containing 10 mM Tris-HCl, pH 7.5, 150 mM sodium chloride (TBS) and 3% bovine serum albumin.

12.2 Binding Assay 100 ml of scFv(FRP5)-DETA-DGAL4 protein in TBS containing 3% bovine serum albumin at concentrations ranging from 60 pM to 1 mM are added to the cells in triplicates and incubated for 1 h at 37° C. in a humified atmosphere. The cells are washed twice with TBS and 100 ml of a 1:2000 dilution of a polyclonal rabbit antiserum raised against purified Pseudomonas exotoxin A (Wels et al., Cancer Res. 52: 6310, 1992) in TBS containing 3% bovine serum albumin are added to each well for 30 min at 37° C. in a humified atmosphere. The cells are washed twice with TBS and 100 ml of a 1:4000 dilution of alkaline phosphatase-coupled goat anti-rabbit serum (Sigma) in TBS containing 3% bovine serum albumin are added to each well for 30 min at 37° C. in a humified atmosphere. The cells are washed twice with TBS and the activity of bound alkaline phosphatase is detected by incubation of the cells with 100 ml/well of 1 mg/ml p-nitrophenyl-phosphate in 1 M Tris-HCl, pH 8.0. Alkaline phosphatase activity in each well is quantitated by measuring the specific absorption at 405 nm versus non-specifc absorption at 490 nm in a microplate reader (Dynatech). scFv(FRP5)-DETA-DGAL4 is binding to SK-BR-3 cells with a half maximal saturation value of 2×10$^{-8}$ M.

EXAMPLE 13

DNA-transfer Experiments 13.1 Calcium-phosphate Transfection

Calcium phosphate transfections of COS-1 and SK-BR-3 cells are carried out with the pSV2LUC-G4 reporter plasmid described in Example 10. To DNA solutions in water 2.5 M calcium chloride is added to a final concentration of 166 mM calcium chloride. 1 volume of 2×HBS buffer, pH 7.12, containing 50 mM HEPES, 15 mM Na$_2$HPO$_4$, and 280 mM sodium chloride, is added dropwise with constant flow of air bubbles through the mixture. The final DNA concentration in the mixture is 10 nM in the experiment with COS-1 cells and 1.9 nM in the experiment with SK-BR-3 cells. Crystals are allowed to form in the solution for 30 min at room temperature. 100 ml of the solution is added to one well of tissue culture cells in 12 well tissue culture plates as described in 13.2, cells are harvested and luciferase units are determined as described in 13.3.

13.2 Cell Culture and DNA Transfer

SK-BR-3 human breast carcinoma cells (ATCC HTB30) and COS-1 SV40 transformed African Green monkey kidney cells (ATCC CRL1650) are seeded in 12 well tissue culture plates at a density of 3.6×10$^4$ cells/well and grown overnight at 37° C. The tissue cuture medium is exchanged with 1 ml/well fresh medium and the cells are grown for another 5 h. 100 ml of the respective sample containing the DNA-transfer mixture described in 13.4, 13.5, 13.6 or 13.7 is added to each well and the cells are incubated at 37° C. overnight. The tissue culture medium is replaced with 2 ml/well of fresh medium and the cells are incubated for another 24 h before they are harvested for analysis as described in 13.3.

13.3 Luciferase Assay

The medium is removed from the cells and cells are washed twice with PBS. 100 ml of lysis buffer, pH 7.8, containing 25 mM Gly-Gly dipeptide (Sigma), 1 mM DTT, 15% glycerol, 8 mM magnesium sulphate, 1 mM EDTA, 1% Triton X100, is added to each well and the cells are incubated for 15 min at room temperature. The lysate is collected and centrifuged for 5 sec in an Eppendorf centrifuge to remove particulate matter. 50 ml of the supernatant is mixed with 50 ml of dilution buffer, pH 7.8, containing 25 mM Gly-Gly dipeptide, 10 mM magnesium sulphate, 5 mM ATP. 300 ml of luciferin solution, pH 7.8, containing 25 mM Gly-Gly dipeptide, 0.5 mM coenzyme A (Boehringer Mannheim), 250 mM luciferin (Sigma), is added to the sample and luciferase activity is determined with a luminometer.

13.4 scFv(FRP5)-DE-TA-DGAL4-mediated DNA Transfer in COS-1 Cells

DNA of pSV2LUC-G4 reporter plasmid described in Example 10 is mixed with scFv(FRP5)-DETA-DGAL4 protein at a final concentration of 10 nM (DNA) and 40 nM (protein) in a buffer containing 50 mM HEPES, pH 7.5, 50 mM potassium chloride, 5 mM magnesium chloride and 100 mM zinc chloride. The mixture is incubated for 10 min at room temperature to allow the formation of protein/DNA complexes. Poly-L-lysine (Sigma) is added to the mixture to final concentrations of 100 or 500 nM, respectively, and the mixture is incubated for further 30 min at room temperature. 100 ml of the solution is added to one well of COS-1 cells in 12 well tissue culture plates as described in 13.2 cells are harvested and luciferase units are determined as described in 13.3. Expression of luciferase is detected in cells transfected with the calcium-phosphate transfection method described in 13.1 and cells treated with scFv(FRP5)-DETA-DGAL4/pSV2LUC-G4 complex containing poly-L-lysine, but not in cells treated with pSV2LUC-G4 and poly-L-lysine alone.

13.5 scFv(FRP5)-DETA-DGAL4-mediated DNA Transfer in SK-BR-3 Cells

A mixture containing DNA of pSV2LUC-G4 reporter plasmid and scFv(FRP5)-DETA-DGAL4 protein is prepared as described in 13.4. The mixture is incubated for 10 min at room temperature to allow the formation of protein/DNA complexes. Poly-L-lysine (Sigma) is added to the mixture to a final concentration of 100 nM and the mixture is incubated for further 30 min at room temperature. 100 ml of the solution is added to one well of SK-BR-3 cells in 12 well tissue culture plates as described in 13.2, cells are harvested and luciferase units are determined as described in 13.3. Expression of luciferase is detected in cells transfected with the calcium-phosphate transfection method described in 13.1 and cells treated with scFv(FRP5)-DETA-DGAL4/pSV2LUC-G4 complex containing poly-L-lysine, but not in cells treated with pSV2LUC-G4 alone or scFv(FRP5)-DETA-DGAL4/pSV2LUC-G4 complex without the addition of poly-L-lysine.

13.6 Competition Assay

A mixture containing DNA of pSV2LUC-G4 reporter plasmid and scFv(FRP5)-DETA-DGAL4 protein is prepared as described in 13.4. The mixture is incubated for 10 min at room temperature to allow the formation of protein/DNA complexes. Poly-L-lysine (Sigma) is added to the mixture to a final concentration of 500 nM and the mixture is incubated for further 30 min at room temperature. One sample is prepared containing in addition to pSV2LUC-G4 reporter plasmid, scFv(FRP5)-DETA-DGAL4 and poly-L-lysine the monoclonal antibody FRP5 which has the same binding specificity as scFv(FRP5)-DETA-DGAL4 as a competitor for binding to p185$^{erbB-2}$ at a final concentration of 1.2 mM. 100 ml of the solution is added to one well of COS-1 cells in 12 well tissue culture plates as described in 13.2, cells are harvested and luciferase units are determined as described in 13.3. Expression of luciferase is detected in cells treated with scFv(FRP5)-DETA-DGAL4/pSV2LUC-G4 complex containing poly-L-lysine, but not in cells treated only with pSV2LUC-G4 and poly-L-lysine or scFv(FRP5)-DETA-DGAL4/pSV2LUC-G4 complex containing poly-L-lysine in the presence of an excess of monoclonal antibody FRP5 as competitor.

EXAMPLE 14
Isolation of RNA from the Breast Carcinoma Cell Line MDA-MB-468

14.1 Growth of MDA-MB-468 Cells

MDA-MB-468 breast carcinoma cells (ATCC HTB132) are grown as monolayers on tissue culture plates at 37° C. in DMEM (Seromed) further containing 8% FCS (Amined) and 100 mg/ml of gentamycin (Seromed) in a humidified atmosphere of air and 7.5% $CO_2$. The cells are washed twice with PBS on ice, PBS is removed and the plates are kept on ice.

14.2 Extraction of Total Cellular RNA from MDA-MB-468 Cells

Total RNA is extracted using the acid guanidinium thiocyanate-phenol-chloroform method described by Choczynski & Dacchi (Anal. Biochem. 162: 156, 1987). The cells from 2 semi-confluent tissue culture plates are lysed on ice in the presence of 2 ml denaturing solution (see Example 3.2). The lysate is homogenized at room temperature. Sequentially, 0.2 ml of 2 M sodium acetate, pH 4, 2 ml of phenol (water saturated) and 0.4 ml of chloroform-isoamyl alcohol mixture (49:1) are added to the lysate. The final suspension is shaken vigorously for 10 sec and cooled on ice for 15 min. The samples are centrifuged at 10,000×g for 20 min at 4° C. After centrifugation, RNA which is present in the aqueous phase is mixed with 2 ml of isopropanol and placed at −20° C. for 1 h. The RNA precipitate is collected by centrifugation, the pellet dissolved in 0.5 ml water and the RNA precipitated by addition of 1 volume of isopropanol at −20° C. After centrifugation and washing the pellet in ethanol, the final pellet of RNA is dissolved in water. The method yields approximately 100 mg of total cellular RNA. The final purified material is stored frozen at −20° C.

EXAMPLE 15
Cloning of a Human Transforming Growth Factor-a cDNA Fragment

Total cellular RNA isolated from MDA-M-468 cells as described in Example 14 provides the source for cDNA synthesis and subsequent amplification of a human transforming growth factor (TGF)-a encoding cDNA fragment. Amplification products of the expected size are purified from agarose gels and cloned into appropriate vectors. Intact cDNA clones are identified by sequencing.

15.1 cDNA Synthesis 5 mg of total RNA isolated from MDA-MB468 cells is used in a 33 ml first strand cDNA synthesis reaction with 11 ml Bulk First-Strand Reaction Mix (Pharmacia), 200 ng NotI-d(T)$_{18}$ primer (Pharmacia), and 1 ml 200 mM DTT solution according to procedures provided by the manufacturer.

15.2 Polymerase Chain Reaction 2 ml of the cDNA reaction is used for DNA amplification in a 50 ml reaction containing 25 pmol each of the two oligonucleotides complementary to regions in the human TGF-a gene 5'-GACCCGAAGCTTGGTACCGGTGTGGTGTCC CATTTTAATG -3' (SEQ D NO. 29) and 5'-TTCTGGGAGCTCTCTAGAGAGGCCAGGAGGT CCGC-3' (SEQ ID NO. 30), 4 ml 2.5 mM dNTP (N=G, A, T, C) mixture, and 5 ml 10× Vent DNA polymerase buffer (New England Biolabs) and 2.5 U of Vent DNA polymerase (New England Biolabs). Vent DNA polymerase is added after initial denaturation at 94° C. for 4 min. For 30 cycles annealing is performed for 1 min at 52° C., primer extension for 45 sec at 72° C., denaturation for 1 min at 94° C. Finally, amplification is completed by a 2 min primer extension step at 72° C.

15.3 Modification and Purification

Amplification products are separated on a 1.5% (w/v) agarose gel (ultra pure agarose, BRL), DNA of the expected size is eluted, and subsequently digested with HindIII and XbaI. The expected 171 bp DNA fragment encoding amino acids 1 to 50 of human TGF-a is separated on a 1.5% agarose gel and purified by elution from the gel as described above.

15.4 Ligation

Plasmid pFLAG-1 is digested with SalI, and treated with the Klenow enzyme to create blunt ends; the linearized fragment is digested with XbaI. A truncated Pseudomonas ETA gene lacking the cell-binding domain Ia is isolated from pWW20 (see Example 1.1) by EcoRI cleavage, Klenow fill-in and Subsequent XbaI digestion. This blunt-ended XbaI fragment is inserted into the blunt-ended XbaI pFLAG-1 vector. The resulting plasmid, pSG100, is digested with HindIII and XbaI and a double stranded DNA linker encoding 6 histidine residues is inserted in frame 5' of the ETA sequences yielding pSW200. A DNA fragment containing the ompA signal peptide, the FLAG epitope and the N-terminal histidine-encoding sequences is isolated by NdeI and XbaI digestion of pSW50 (see Example 8.2) and inserted into NdeI/XbaI digested pSW200. The resulting plasmid is designated pSW202. pSW202 (50 ng) digested with HindIII and XbaI, and 30 ng of purified amplification product are ligated using 0.5 U T4 DNA ligase (New England Biolabs) in 50 mM Tris-HCl, pH 7.8, 10 mM magnesium chloride, 10 mM DTT, and 0.8 mM ATP overnight at 16° C. One half of ligation mixture is used to transform *E.coli* XL1 Blue (Stratagene) to obtain ampicillin resistant colonies. These are screened for the desired ligation product using a NaOH based plasmid "miniprep" method (Maniatis et al., supra). The following plasmid is obtained: pSW202-TGF. The partial DNA sequence of pSW202-TGF is shown in SEQ ID NO. 31. Said sequence has the following features:

| | |
|---|---|
| from 1 to 15 bp | synthetic spacer |
| from 16 to 165 bp | encoding amino acids 1 to 50 of human TGF-a |
| from 166 to 173 bp | synthetic spacer |

EXAMPLE 16

Construction of the TGF-a-DETA-DGAL4 Fusion Gene 16.1 Derivation of DNA Fragments and Purification pSW202-TGF (1 mg) is digested with HindIII and SalI. DNA fragments are separated on a 1.0% (w/v) agarose gel (ultra pure agarose, BRL) and the expected bp HindIII/SalI DNA fragment carrying the TGF-a-DETA$_{252-308}$ fusion gene is eluted. Plasmid pWF45-5 (1 mg) is digested with SalI and XbaI. DNA fragments are separated and the expected 655bp SalI/XbaI DNA fragment encoding DETA$_{309-366}$-DGAL4 is eluted as described above. pWF45-5 (1 mg) is digested with HindIII and XbaI. DNA fragments are separated and the expected HindIII/XbaI vector fragment is eluted as described above.

16.2 Ligation 50 ng of purified HindIII/XbaI pWF45-5 vector fragment, and 30 ng of purified HindIII/SalI TGF-a-DETA fragment, and 30 ng of purified Sal/XbaI DETA-DGAL4 fragment are ligated using 0.5 U T4 DNA ligase (New England Biolabs) in 50 mM Tris-HCl, pH 7.8, 10 mM magnesium chloride, 10 mM DTT, and 0.8 mM ATP overnight at 16° C. One half of ligation mixture is used to transform *E.coli* XL1 Blue (Stratagene) to obtain ampicillin resistant colonies. These are screened for the desired ligation product using a NaOH based plasmid "miniprep" method. The following plasmid is obtained: pWF47-TGF. The partial DNA sequence of pWF47-TGF encodes TGF-a-DETA-DGAL4 fusion protein is shown in SEQ ID NO. 3. Said sequence has the following features:

| | |
|---|---|
| 1 to 63 bp | encoding the *E. coli* ompA signal peptide |
| 64 to 87 bp | encoding the synthetic FLAG epitode |
| 88 to 99 bp | spacer sequence |
| 100 to 249 bp | encoding amino acids 1 to 50 of human TGF-a |
| 259 to 276 bp | encoding 6 His residues |
| 277 to 279 bp | synthetic spacer sequence |
| 280 to 624 bp | encoding amino acid 252 to 366 of ETA |
| 625 to 627 bp | spacer |
| 628 to 1065 bp | encoding aa 2 to 147 of yeast GAL4 |
| 1066 to 1089 bp | spacer including sequence coding for KDEL retention signal |

The partial deduced amino acid sequence of the pWF47-TGF encoded TGF-a-DETA-D GAL4 protein including a peptide spacer at the N-terminus (aa 1 to 12) is shown in SEQ ID NO.4.

EXAMPLE 17

Bacterial Expression and Purification of TGF-a-DETA-D GAL4

A translocation domain derivable from *P. aeruginosa* exotoxin A (ETA), particularly a domain consisting essentially of domain II of ETA (amino acids 253 to 364 of ETA as set forth in Gray et al., Proc. Natl. Acad. Sci. USA 81: 2645, 1984), e.g. a translocation domain consisting of amino acids 252 to 366 of ETA is described in Examples 17 and 18 in conjunction with SEQ ID NOs. 1, 3 and 5.

Plasmid pWF47-TGF is transformed into *E.coli* K12 (Manoil & Beckwith, Proc. Natl. Acad. Sci. USA 82: 8129, 1985). Expression and purification of TGF-a-DETA-D GAL4 is carried out as described in Example 9. for the expression and purification of scFv(FRP5)-DETA-D GAL4.

EXAMPLE 18

Construction of an Interleukin-2-DETA-DGAL4 Fusion Gene 18.1 Polymerase Chain Reaction 20 ng of a pBR322 derivative carrying a human interleukin (IL)-2 cDNA insert (Taniguchi et al., Nature 302: 305, 1983) is used for DNA amplification in a 50 ml reaction containing 25 pmol each of the two oligonucleotides complementary to regions in the human IL-2 gene. 5'-TATAATAAGCTTGCACCTACTTCAAG-3' (SEQ ID NO. 32) and 5'-TTGAATGCTAGCGTTAGTGTTGAGATG-3' (SEQ ID NO. 33), 4 ml 2.5 mM dNTP (N=G, A, T, C) mixture, and 5 ml 10× Vent DNA polymerase buffer (New England Biolabs) and 2.5 U of Vent DNA polymerase (New England Biolabs). Vent DNA polymerase is added after initial denaturation at 94° C. for 4 min. For 30 cycles annealing is performed for 1 min at 50° C., primer extension for 45 sec at 72° C., denaturation for 1 min at 94° C. Finally, amplification is completed by a 2 min primer extension step at 72° C.

18.2 Modification and Purification

Amplification products are separated on a 1.5% (w/v) agarose gel (ultra pure agarose, BRL), DNA of the expected size is eluted, and subsequently digested with HindIII and NheI. The expected 408 bp DNA fragment encoding amino acids 1 to 113 of human IL-2 is separated on a 1.5% agarose gel and purified by elution from the gel as described above.

18.3 Derivation of DNA Fragments and Purification pWF46-5 (1 mg) (see Example 8.) is digested with XbaI and EcoRI. DNA fragments are separated on a 1.0% (w/v) agarose gel (ultra pure agarose, BRL) and the expected 821 bp XbaI/EcoRI DNA fragment carrying the DETA-DGAL4 coding region is eluted. In a separate digestion pWF46-5 (1 mg) is digested with HindIII and EcoRI. DNA fragments are separated and the expected 5.4 kb HindIII/EcoRI vector fragment is eluted as described above.
18.4 Ligation pWF46-5 HindIII/EcoRI vector fragment (50 ng), 30 ng of purified HindIII/NheI IL-2 cDNA fragment, and 30 ng of purified XbaI/EcoRI DETA-DGAL4 fragment are ligated using 0.5 U T4 DNA ligase (New England Biolabs) in 50 mM Tris-HCl, pH 7.8, 10 mM magnesium chloride, 10 mM DTT, and 0.8 mM ATP overnight at 16° C. One half of ligation mixture is used to transform E.coli XL1 Blue (Stratagene) to obtain ampicillin resistant colonies. These are screened for the desired ligation product using a NaOH based plasmid "miniprep" method.

The following plasmid is obtained: pWF46-EL-2. The partial DNA sequence of pWF46-IL-2 is shown in SEQ ID NO. 5.

Said sequence has the following features:

| | |
|---|---|
| 1 to 63 bp | encoding the E. coli ompA signal peptide |
| 64 to 87 bp | encoding the synthetic FLAG epitope |
| 88 to 114 bp | spacer sequence |
| 109 to 114 bp | spacer sequence |
| 115 to 513 bp | encoding human IL-2 amino acids 1 to 113 |
| 514 to 516 bp | space sequence |
| 517 to 861 bp | encoding amino acid 252 to 366 of ETA |
| 862 to 865 bp | spacer |
| 866 to 1302 bp | encoding aa 2 to 147 of yeast GAL4 |
| 1303 to 1326 bp | spacer including sequence coding for KDEL retention signal |
| 1327 to 1329 bp | ochre stop codon |

The partial deduced amino acid sequence of the pWF46-IL-2 encoded IL-2-DETA-D GAL4 protein including an N-terminal peptide spacer (aa is shown in SEQ ID NO. 6.
18.5 Bacterial Expression and Purification of IL-2-DETA-D GAL4

Plasmid pWF46-IL-2 is transformed into E.coli CC118 (Manoil & Beckwith, Proc. Natl. Acad. Sci. USA 82: 8129, 1985). Expression and purification of IL-2-DETA-D GAL4 is carried out as described in Example 8. for the expression and purification of scFv(FRP5)DETA-D GAL4.
Deposition Data E. coli XL 1 Blue/pWF47-TGF was deposited with the Deutsche Sammlung von Mikroorganismen und Zellkulturen GmbH (DSM), Mascheroder Weg lb, D-38124 Braunschweig on Oct. 24, 1994 under the accession number DSM 9513.

EXAMPLE 19
Construction of Plasmid pSW50-GD5

A plasmid for the bacterial expression of a fusion protein consisting of the ompA signal peptide, AGAL4, a fragment spanning amino acids Val196 to Gly384 of the diphtheria toxin (DT) B fragment (translocation-domain), the scFv (FRP5) single chain antibody domain and adjacent linker sequences is constructed.
19.1 Deletion of scFv(FRP5) and ΔETA Domains from Plasmid pWF46-5 pWF46-5 (1 μg) is digested with HindIII. DNA fragments are separated on a 1.0% (w/v) agarose gel (ultra pure agarose, BRL) and the DNA fragment consisting of the pSW50 vector and the ΔGAL4 fragment is eluted as described above. The eluted fragment is subsequently ligated using 0.5 U T4 DNA ligase (New England Biolabs) in 50 mM Tris-HCl, pH 7.8, 10 mM magnesium chloride, 10 mM DTT, and 0.8 mM ATP overnight at 16° C. One half of ligation mixture is used to transform E.coli XL1 Blue (Stratagene) to obtain ampicillin resistant colonies. These are screened for the desired ligation product using a NaOH based plasmid "miniprep" method (Maniatis et al., Molecular Cloning: A Laboratory Manual/Second Edition, Cold Spring Harbor Laboratory, 1989). The following plasmid is obtained: pSW50-G.
19.2 Insertion of a Linker Sequence A double stranded DNA adaptor with SacI and SalI compatible ends and containing an internal NheI restriction site is constructed by annealing 0.5 nmol of the oligonucleotide 5'-CGCTAGCTGGTGGTG-3' (SEQ ID NO:50) with 0.5 nmol of the oligonucleotide 5'-TCGACACCACCAGCTAGCGAGCT-3' (SEQ ID NO:51) by incubation at 65° C. for 3 min and cooling to room temperature. pSW50-G (1 μg) is digested with SacI and SalI. DNA fragments are separated on a 1.0% (w/v) agarose gel (ultra pure agarose, BRL) and the DNA fragment consisting of the pSW50 vector and the ΔGAL4 fragment is eluted as described above. The eluted fragment (50 ng) and 20 pmol SacI/SalI oligonucleotide adaptor are subsequently ligated using 0.5 U T4 DNA ligase (New England Biolabs) in 50 mM Tris-HCl, pH 7.8, 10 mM magnesium chloride, 10 mM DTT, and 0.8 mM ATP overnight at 16° C. One half of ligation mixture is used to transform E.coli XL1 Blue (Stratagene) to obtain ampicillin resistant colonies. These are screened for the desired ligation product using a NaOH based plasmid "miniprep" method (Maniatis et al., Molecular Cloning: A Laboratory Manual/Second Edition, Cold Spring Harbor Laboratory, 1989). The following plasmid is obtained: pSW50-G/NheI.
19.3 Isolation of the Diphtheria Toxin Gene Fragment Encoding the Translocation Domain (ΔDT)

A plasmid (pJV127) which contains the diphtheria toxin—interleukin-2 fusion gene fragment encoding DAB389-IL-2 (Williams et al., J. Biol. Chem. 265: 11885–11889, 1990) is used as a template in a polymerase chain reaction to amplify a DNA fragment comprising amino acids Val196 to Gly384 of the diphtheria toxin (DT) B fragment (translocation domain), designated ΔDT.

50 ng of pJV127 is used for DNA amplification in a 50 μl reaction containing 50 pmol each of the two oligonucleotides complementary to regions in the diphtheria toxin gene 5'-CGTGTCAGGCTAGCAGTAGGTAGC-3' (SEQ ID NO:52) and 5'-CATGCGTGTCGACACCCGGAGAGTAAGC-3' (SEQ ID NO:53), 4 μl 2.5 mM dNTP (N=G, A, T, C) mixture, 5 μl 10x Taq DNA polymerase buffer (Boehringer Mannheim) and 2.5 U of Taq DNA polymerase (Boehringer Mannheim). Taq DNA polymerase is added after initial denaturation at 94° C. for 2 min. For 30 cycles annealing is performed for 1 min at 55° C., primer extension for 1 min at 72° C., denaturation for 1 min at 94° C. Finally, amplification is completed by a 3 min primer extension step at 72° C.

Amplification products are separated on a 1.2% (w/v) agarose gel (ultra pure agarose, BRL), DNA of the expected size is eluted as described above, and subsequently digested with NheI and SalI. The expected 575 bp diphtheria toxin DNA fragment encoding the translocation domain and adjacent synthetic linker sequences is separated on a 1.2% agarose gel and purified by elution from the gel as described above.
19.4 Ligation pSW50-G/NheI (50 ng) digested with NheI and SalI, and 30 ng of purified amplification product are ligated using 0.5 U T4 DNA ligase (New England Biolabs) in 50 mM Tris-HCl, pH 7.8, 10 mM magnesium chloride, 10 mM DTT, and 0.8 mM ATP overnight at 16° C. One half of ligation mixture is used to transform E.coli XL1 Blue (Stratagene) to obtain ampicillin resistant colonies. These are screened for the desired ligation product using a NaOH based plasmid "miniprep" method (Maniatis et al., Molecular Cloning: A Laboratory Manual/Second Edition, Cold Spring Harbor Laboratory, 1989). The following plasmid is obtained: pSW50-GD.

19.5 Derivation of scFv(FRP5) DNA Fragment and Ligation of pSW50-GD5:

pWW152-5 (1 μg) carrying the gene encoding the ErbB-2 specific single chain Fv (scFv) molecule scFv(FRP5) described by Wels et al., Int. J. Cancer 60: 137–144, 1995, is digested with SalI and BamHI. DNA fragments are separated on a 1.0% (w/v) agarose gel (ultra pure agarose, BRL) and the expected 756 bp SalI/BamHI DNA fragment carrying the scFv(FRP5) domain and adjacent synthetic sequences is eluted as described above. pSW50-GD (50 ng) digested with SalI and BglII and scFv(FRP5) SalI/BamHI (50 ng) DNA fragments are ligated using 0.5 U T4 DNA ligase (New England Biolabs) in 50 mM Tris-HCl, pH 7.8, 10 mM magnesium chloride, 10 mM DTT, and 0.8 mM ATP overnight at 16° C. One half of ligation mixture is used to transform *E.coli* XL1 Blue (Stratagene) to obtain ampicillin resistant colonies. These are screened for the desired ligation product using a NaOH based plasmid "miniprep" method (Maniatis et al., Molecular Cloning: A Laboratory Manual/ Second Edition, Cold Spring Harbor Laboratory, 1989). The following plasmid is obtained: pSW50-GD5. The partial DNA sequence of pSW50-GD5 is shown in SEQ ID NO. 34. Said sequence has the following features:

| from 1 to 63 bp | encoding the *E. coli* ompA signal peptide |
| from 64 to 87 bp | encoding the synthetic FLAG epitope |
| from 88 to 108 bp | synthetic spacer sequence |
| from 109 to 546 bp | encoding amino acids 2 to 147 of yeast GAL4 |
| from 547 to 558 bp | synthetic spacer sequence |
| from 559 to 1125 bp | encoding amino acids Val196 to Gly384 of diphtheria toxin |
| from 1126 to 1146 bp | synthetic spacer sequence |
| from 1147 to 1866 bp | encoding scFv(FRP5) |
| from 1867 to 1908 bp | synthetic spacer sequence |
| from 1909 to 1911 bp | stop codon |
| from 1912 to 1919 bp | non-coding synthetic spacer |

The deduced amino acid sequence of the pSW50-GD5 encoded ΔGAL4-ΔDT-scFv(FRP5) (=GD5) protein including a peptide spacer at the N-terminus (aa 1 to 15) is shown in SEQ ID NO. 35.

EXAMPLE 20

Construction of Plasmid pSW55-GD5

A plasmid for the bacterial expression of a fusion protein consisting of ΔGAL4, a fragment spanning amino acids Val196 to Gly384 of the diphtheria toxin (DT) B fragment (translocation domain), the scFv(FRP5) single chain antibody domain and adjacent linker sequences is constructed.

20.1 Insertion of a Linker Sequence

A double stranded DNA adaptor with NdeI and HindIII compatible ends is constructed by annealing 0.5 nmol of the oligonucleotide 5'-TATGGACTACAAGGACGACGATGACAAGAA GCTGCACCATCATCACCATCACA-3' (SEQ ID NO:54) with 0.5 nmol of the oligonucleotide 5'-AGCTTGTGATGGTGATGATGGTGCAGCTTCT TGTCATCGTCGTCCTTGTAGTCCA-3' (SEQ D NO:55) by incubation at 65° C. for 3 min and cooling to room temperature.

pSW50 (1 μg) is digested with NdeI and HindIII. DNA fragments are separated on a 1.0% (w/v) agarose gel (ultra pure agarose, BRL) and the pSW50 vector DNA fragment is eluted as described above. The eluted fragment (50 ng) and 20 pmol NdeI/HindIII oligonucleotide adaptor are subsequently ligated using 0.5 U T4 DNA liquse (New England Biolabs) in 50 mM Tris-HCl, pH 7.8, 10 mM magnesium chloride, 10 mM DTT, and 0.8 mM ATP overight at 16° C. One half of ligation mixture is used to transform *E.coli* XL1 Blue (Stratagene) to obtain ampicillin resistant colonies. These are screened for the desired ligation product using a NaOH based plasmid "miniprep" method (Maniatis et al., Molecular Cloning: A Laboratory Manual/Second Edition, Cold Spring Harbor Laboratory, 1989). The following plasmid is obtained: pSW55.

20.2 Derivation of DNA Fragments and Ligation pSW50-GD5 (1 μg) is digested with HindIII and KpnI and in a separate reaction with KpnI and XhoI. DNA fragments are separated on a 1.0% (wv) agarose gel (ultra pure agarose, BRL) and the expected 673 bp HindIII/KpnI DNA fragment the ΔGAL4 domain, the 5' part of the ΔDT domain and adjacent synthetic sequences, and the 1106 bp KpnI/XhoI fragment carrying the 3' part of the ΔDT domain, the scFv(FRP5) domain and adjacent synthetic sequences are eluted as described above. pSW55 (50 ng) digested with HindIII and XhoI, and the HindIII/KpnI and KpnI/XhoI (50 ng each) DNA fragments are ligated using 0.5 U T4 DNA ligase (New England Biolabs) in 50 mM Tris-HCl, pH 7.8, 10 mM magnesium chloride, 10 mM DTT, and 0.8 mM ATP overnight at 16° C. One half of ligation mixture is used to transform *E.coli* XL1 Blue (Stratagene) to obtain ampicillin resistant colonies. These are screened for the desired ligation product using a NaOH based plasmid "miniprep" method (Maniatis et al., Molecular Cloning: A Laboratory Manual/ Second Edition, Cold Spring Harbor Laboratory, 1989). The following plasmid is obtained: pSW55-GD5. The partial DNA sequence of pSW55-GD5 is shown in SEQ ID NO. 36. Said sequence has the following features:

| | |
|---|---|
| from 1 to 3 bp | synthetic spacer sequence |
| from 4 to 27 bp | encoding the synthetic FLAG epitope |
| from 28 to 51 bp | synthetic spacer sequence |
| from 52 to 489 bp | encoding amino acids 2 to 147 of yeast GAL4 |
| from 490 to 501 bp | synthetic spacer sequence |
| from 502 to 1068 bp | encoding amino acids Val196 to Gly384 of diphtheria toxin |
| from 1069 to 1089 bp | synthetic spacer sequence |
| from 1090 to 1809 bp | encoding scFv(FRP5) |
| from 1810 to 1851 bp | synthetic spacer sequence |
| from 1852 to 1854 bp | stop codon |
| from 1855 to 1862 bp | non-coding synthetic spacer |

The deduced amino acid sequence of the pSW55-GD5 encoded ΔGAL4-ΔDT-scFv(FRP5) (=GD5) protein including a peptide spacer at the N-terminus (aa 1 to 17) is shown in SEQ ID NO. 37.

EXAMPLE 21

Construction of Plasmid pSW50-GDI

A plasmid for the bacterial expression of a fusion protein consisting of the ompA signal peptide, ΔGAL4, a fragment spanning amino acids Val196 to Gly384 of the diphtheria toxin (DT) B fragment (translocation domain), the human interleukin-2 (IL-2) domain and adjacent linker sequences is constructed.

21.1 Construction of Plasmid pWW152-IL-2

Plasmid pSW50-IL-2 (1 μg) is digested with EcoRI. The linearized DNA is treated with DNA polymerase I (Klenow fragment) (Boehringer Mannheim) to create blunt ends (Maniatis et al., Molecular Cloning: A Laboratory Manual/

Second Edition, Cold Spring Harbor Laboratory, 1989) and subsequently digested with HindIII. DNA fragments are separated on a 1.0% (w/v) agarose gel (ultra pure agarose, BRL) and the expected 418 bp HindIII/blunt ended DNA fragment carrying the IL-2 domain and adjacent synthetic sequences is eluted as described above. Plasmid pWW152 digested with HindIII and PvuII (50 ng) and the HindIII/ blunt ended IL-2 DNA fragment are ligated using 0.5 U T4 DNA ligase (New England Biolabs) in 50 mM Tris-HCl, pH 7.8, 10 mM magnesium chloride, 10 mM DTT, and 0.8 mM ATP overnight at 16° C. One half of ligation mixture is used to transform, E.coli XL1 Blue (Stratagene) to obtain ampicillin resistant colonies. These are screened for the desired ligation product using a NaOH based plasmid "miniprep" method (Maniatis et al., Molecular Cloning: A Laboratory Manual/Second Edition, Cold Spring Harbor Laboratory, 1989). The following plasmid is obtained: pWW152-IL-2.

21.2 Derivation of DNA Fragments and Ligation pWW152-IL-2 (1 μg) is digested with SalI and BglII. DNA fragments are separated on a 1.0% (w/v) agarose gel (ultra pure agarose, BRL) and the SalI/BglII DNA fragment carrying the IL-2 domain and adjacent synthetic sequences is eluted as described above. pSW50-GD (50 ng) digested with SalI and BglII and IL-2 SalI/BglII (50 ng) DNA fragments are ligated using 0.5 U T4 DNA ligase (New England Biolabs) in 50 mM Tris-HCl, pH 7.8, 10 mM magnesium chloride, 10 mM DTT, and 0.8 mM ATP overnight at 16° C. One half of ligation mixture is used to transform E.coli XL1 Blue (Stratagene) to obtain ampicillin resistant colonies. These are screened for the desired ligation product using a NaOH based plasmid "miniprep" method (Maniatis et al., Molecular Cloning: A Laboratory Manual/ Second Edition, Cold Spring Harbor Laboratory, 1989). The following plasmid is obtained: pSW50-GDI. The partial DNA sequence of pSW50-GDI is shown in SEQ ID NO. 38. Said sequence has the following features:

| from 1 to 63 bp | encoding the E. coli ompA signal peptide |
|---|---|

-continued

| from 64 to 87 bp | encoding the synthetic FLAG epitope |
|---|---|
| from 88 to 108 bp | synthetic spacer sequence |
| from 109 to 546 bp | encoding amino acids 2 to 147 of yeast GAL4 |
| from 547 to 558 bp | synthetic spacer sequence |
| from 559 to 1125 bp | encoding amino acids Val196 to Gly384 of diphtheria toxin |
| from 1126 to 1152 bp | synthetic spacer sequence |
| from 1153 to 1551 bp | encoding human IL-2 amino acids 1 to 113 |
| from 1552 to 1554 bp | stop codon |
| from 1555 to 1605 bp | non-coding synthetic spacer |

The deduced amino acid sequence of the pSW50-GDI encoded ΔGAL4-ΔDT-IL-2 (=GDI) protein including a peptide spacer at the N-terminus (aa 1 to 15) is shown in SEQ ID NO. 39.

EXAMPLE 22

Bacterial Expression and Purification of GD5

Plasmids pSW50-GD5 or pSW55-GD5 are transformed into E.coli K12. Expression and purification of ΔGAL4-ΔDT-scFv(FRP5) protein GD5is carried out-as described in Example 9. for the expression and purification of scFv (FRP5)-ΔETA-Δ GAL4.

EXAMPLE 23

GD5-mediated DNA Transfer in COS-1 Cells

COS-1 cells are seeded in12 well tissue culture plates as described in Example 13.2. DNA of pSV2LUC-G4 reporter plasmid described in Example 10 is mixed with the GD5 protein at a final concentration of 10 nM (DNA) and 40 nM (protein) using the buffer and incubation conditions described in 13.4. Poly-L-lysine (Sigma) is added to the mixture as described in 13.4 and the complex is added to COS-1 cells as described in 13.2. The cells are harvested and luciferase units are determined as described in 13.3. Expression of luciferase is detected in cells treated with GD5/ pSV2LUC-G4 complex containing poly-L-lysine, but not in cells treated with pSV2LUC-G4 and poly-L-lysine alone.

What is claimed is:

1. A multidomain protein comprising, a target cell-specific binding domain, a translocation domain and a nucleic acid binding domain, wherein the translocation domain is derived from a diphtheria toxin but does not include the cytotoxic part of said diphtheria toxin, wherein the translocation domain is derived from amino acids 194–378 or 196–384 of said diphtheria toxin.

2. The multidomain protein according to claim 1, wherein said translocation domain is amino acids 194–378 or 196–384 of said diphtheria toxin.

3. The multidomain protein according to claim 1, further comprising an endoplasmic reticulum retention signal and a nuclear localization signal, wherein said protein has an amino acid sequence selected from the group consisting of SEQ ID NO: 2, SEQ ID NO:4, SEQ ID NO:6, SEQ ID NO:35, SEQ ID NO:37, and SEQ ID NO:39.

* * * * *

SEQUENCE LISTING (1) GENERAL INFORMATION:

(iii) NUMBER OF SEQUENCES: 58

(2) INFORMATION FOR SEQ ID NO: 1:

(i) SEQUENCE CHARACTERISTICS:
      (A) LENGTH: 1692 base pairs
      (B) TYPE: nucleic acid
      (C) STRANDEDNESS: single
      (D) TOPOLOGY: linear (ii) MOLECULE TYPE: DNA (vii) IMMEDIATE SOURCE:
      (B) CLONE: pWF46-5

(ix) FEATURE:
      (A) NAME/KEY: sig_peptide
      (B) LOCATION: 1..63
      (D) OTHER INFORMATION: /product= "E. coli OmpA signal
          peptide"

(ix) FEATURE:
    (A) NAME/KEY: CDS
    (B) LOCATION: 64..1656
    (D) OTHER INFORMATION: /product= "scFv(FRP5)-delta
        ETA-delta GAL4"

(xi) SEQUENCE DESCRIPTION: SEQ ID NO: 1:

```
ATGAAAAAGA CAGCTATCGC GATTGCAGTG GCACTGGCTG GTTTCGCTAC CGTTGCGCAA        60

GCT GAC TAC AAG GAC GAC GAT GAC AAG CTG CAC CAT CAT CAC CAT CAC         108
Asp Tyr Lys Asp Asp Asp Asp Lys Leu His His His His His His
 1               5                  10                  15

AAG CTT CAG GTA CAA CTG CAG CAG TCT GGA CCT GAA CTG AAG AAG CCT         156
Lys Leu Gln Val Gln Leu Gln Gln Ser Gly Pro Glu Leu Lys Lys Pro
             20                  25                  30

GGA GAG ACA GTC AAG ATC TCC TGC AAG GCC TCT GGG TAT CCT TTC ACA         204
Gly Glu Thr Val Lys Ile Ser Cys Lys Ala Ser Gly Tyr Pro Phe Thr
         35                  40                  45

AAC TAT GGA ATG AAC TGG GTG AAG CAG GCT CCA GGA CAG GGT TTA AAG         252
Asn Tyr Gly Met Asn Trp Val Lys Gln Ala Pro Gly Gln Gly Leu Lys
     50                  55                  60

TGG ATG GGC TGG ATT AAC ACC TCC ACT GGA GAG TCA ACA TTT GCT GAT         300
Trp Met Gly Trp Ile Asn Thr Ser Thr Gly Glu Ser Thr Phe Ala Asp
 65                  70                  75

GAC TTC AAG GGA CGG TTT GAC TTC TCT TTG GAA ACC TCT GCC AAC ACT         348
Asp Phe Lys Gly Arg Phe Asp Phe Ser Leu Glu Thr Ser Ala Asn Thr
 80                  85                  90                  95

GCC TAT TTG CAG ATC AAC AAC CTC AAA AGT GAA GAC ATG GCT ACA TAT         396
Ala Tyr Leu Gln Ile Asn Asn Leu Lys Ser Glu Asp Met Ala Thr Tyr
             100                 105                 110

TTC TGT GCA AGA TGG GAG GTT TAC CAC GGC TAC GTT CCT TAC TGG GGC         444
Phe Cys Ala Arg Trp Glu Val Tyr His Gly Tyr Val Pro Tyr Trp Gly
         115                 120                 125

CAA GGG ACC ACG GTC ACC GTT TCC TCT GGC GGT GGC GGT TCT GGT GGC         492
Gln Gly Thr Thr Val Thr Val Ser Ser Gly Gly Gly Gly Ser Gly Gly
     130                 135                 140

GGT GGC TCC GGC GGT GGC GGT TCT GAC ATC CAG CTG ACC CAG TCT CAC         540
Gly Gly Ser Gly Gly Gly Gly Ser Asp Ile Gln Leu Thr Gln Ser His
 145                 150                 155

AAA TTC CTG TCC ACT TCA GTA GGA GAC AGG GTC AGC ATC ACC TGC AAG         588
Lys Phe Leu Ser Thr Ser Val Gly Asp Arg Val Ser Ile Thr Cys Lys
160                 165                 170                 175

GCC AGT CAG GAT GTG TAT AAT GCT GTT GCC TGG TAT CAA CAG AAA CCA         636
Ala Ser Gln Asp Val Tyr Asn Ala Val Ala Trp Tyr Gln Gln Lys Pro
             180                 185                 190

GGA CAA TCT CCT AAA CTT CTG ATT TAC TCG GCA TCC TCC CGG TAC ACT         684
Gly Gln Ser Pro Lys Leu Leu Ile Tyr Ser Ala Ser Ser Arg Tyr Thr
         195                 200                 205

GGA GTC CCT TCT CGC TTC ACT GGC AGT GGC TCT GGG CCG GAT TTC ACT         732
Gly Val Pro Ser Arg Phe Thr Gly Ser Gly Ser Gly Pro Asp Phe Thr
     210                 215                 220

TTC ACC ATC AGC AGT GTG CAG GCT GAA GAC CTG GCA GTT TAT TTC TGT         780
Phe Thr Ile Ser Ser Val Gln Ala Glu Asp Leu Ala Val Tyr Phe Cys
 225                 230                 235

CAG CAA CAT TTT CGT ACT CCA TTC ACG TTC GGC TCG GGG ACA AAA TTG         828
Gln Gln His Phe Arg Thr Pro Phe Thr Phe Gly Ser Gly Thr Lys Leu
240                 245                 250                 255

GAG ATC AAA GCT CTA GAG GGC GGC AGC CTG GCC GCG CTG ACC GCG CAC         876
Glu Ile Lys Ala Leu Glu Gly Gly Ser Leu Ala Ala Leu Thr Ala His
             260                 265                 270
```

| | | |
|---|---|---|
| CAG GCC TGC CAC CTG CCG CTG GAG ACT TTC ACC CGT CAT CGC CAG CCG<br>Gln Ala Cys His Leu Pro Leu Glu Thr Phe Thr Arg His Arg Gln Pro<br>                  275                              280                        285 | 924 |
| CGC GGC TGG GAA CAA CTG GAG CAG TGC GGC TAT CCG GTG CAG CGG CTG<br>Arg Gly Trp Glu Gln Leu Glu Gln Cys Gly Tyr Pro Val Gln Arg Leu<br>                  290                              295                        300 | 972 |
| GTC GCC CTC TAC CTG GCG GCG CGA CTG TCA TGG AAC CAG GTC GAC CAG<br>Val Ala Leu Tyr Leu Ala Ala Arg Leu Ser Trp Asn Gln Val Asp Gln<br>        305                              310                              315 | 1020 |
| GTG ATC CGC AAC GCC CTG GCC AGC CCC GGC AGC GGC GGC GAC CTG GGC<br>Val Ile Arg Asn Ala Leu Ala Ser Pro Gly Ser Gly Gly Asp Leu Gly<br>320                              325                              330                        335 | 1068 |
| GAA GCG ATC CGC GAG CAG CCG GAG CAG GCC CGT CTG GCC CTG ACC CTG<br>Glu Ala Ile Arg Glu Gln Pro Glu Gln Ala Arg Leu Ala Leu Thr Leu<br>                  340                              345                        350 | 1116 |
| GCC GCC GCC GAG AGC GAG CGC TTC GTC CGG CAG GGC ACC GGC AAC GAC<br>Ala Ala Ala Glu Ser Glu Arg Phe Val Arg Gln Gly Thr Gly Asn Asp<br>                        355                              360                        365 | 1164 |
| GAG GCC GGC GCG GCC AAC GCC GAC GAG AAG CTT CTG TCT TCT ATC GAA<br>Glu Ala Gly Ala Ala Asn Ala Asp Glu Lys Leu Leu Ser Ser Ile Glu<br>370                              375                              380 | 1212 |
| CAA GCA TGC GAT ATT TGC CGA CTT AAA AAG CTC AAG TGC TCC AAA GAA<br>Gln Ala Cys Asp Ile Cys Arg Leu Lys Lys Leu Lys Cys Ser Lys Glu<br>        385                              390                              395 | 1260 |
| AAA CCG AAG TGC GCC AAG TGT CTG AAG AAC AAC TGG GAG TGT CGC TAC<br>Lys Pro Lys Cys Ala Lys Cys Leu Lys Asn Asn Trp Glu Cys Arg Tyr<br>400                              405                              410                        415 | 1308 |
| TCT CCC AAA ACC AAA AGG TCT CCG CTG ACT AGG GCA CAT CTG ACA GAA<br>Ser Pro Lys Thr Lys Arg Ser Pro Leu Thr Arg Ala His Leu Thr Glu<br>                  420                              425                        430 | 1356 |
| GTG GAA TCA AGG CTA GAA AGA CTG GAA CAG CTA TTT CTA CTG ATT TTT<br>Val Glu Ser Arg Leu Glu Arg Leu Glu Gln Leu Phe Leu Leu Ile Phe<br>                        435                              440                        445 | 1404 |
| CCT CGA GAA GAC CTT GAC ATG ATT TTG AAA ATG GAT TCT TTA CAG GAT<br>Pro Arg Glu Asp Leu Asp Met Ile Leu Lys Met Asp Ser Leu Gln Asp<br>450                              455                              460 | 1452 |
| ATA AAA GCA TTG TTA ACA GGA TTA TTT GTA CAA GAT AAT GTG AAT AAA<br>Ile Lys Ala Leu Leu Thr Gly Leu Phe Val Gln Asp Asn Val Asn Lys<br>        465                              470                            475 | 1500 |
| GAT GCC GTC ACA GAT AGA TTG GCT TCA GTG GAG ACT GAT ATG CCT CTA<br>Asp Ala Val Thr Asp Arg Leu Ala Ser Val Glu Thr Asp Met Pro Leu<br>480                              485                              490                        495 | 1548 |
| ACA TTG AGA CAG CAT AGA ATA AGT GCG ACA TCA TCA TCG GAA GAG AGT<br>Thr Leu Arg Gln His Arg Ile Ser Ala Thr Ser Ser Ser Glu Glu Ser<br>                  500                              505                        510 | 1596 |
| AGT AAC AAA GGT CAA AGA CAG TTG ACT GTA TCG AGC TCT GAC TAC AAA<br>Ser Asn Lys Gly Gln Arg Gln Leu Thr Val Ser Ser Ser Asp Tyr Lys<br>        515                              520                            525 | 1644 |
| GAC GAA CTT TAAGAATTCT CTAGAGATAT CGTCGACAGA TCTCTCGAG<br>Asp Glu Leu<br>        530 | 1692 |

(2) INFORMATION FOR SEQ ID NO: 2:

(i) SEQUENCE CHARACTERISTICS:
        (A) LENGTH: 530 amino acids
        (B) TYPE: amino acid
        (D) TOPOLOGY: linear (ii) MOLECULE TYPE: protein (xi) SEQUENCE DESCRIPTION: SEQ ID NO: 2:

-continued

```
Asp Tyr Lys Asp Asp Asp Lys Leu His His His His His Lys
 1               5                      10                     15

Leu Gln Val Gln Leu Gln Gln Ser Gly Pro Glu Leu Lys Lys Pro Gly
             20                      25                      30

Glu Thr Val Lys Ile Ser Cys Lys Ala Ser Gly Tyr Pro Phe Thr Asn
             35                      40                      45

Tyr Gly Met Asn Trp Val Lys Gln Ala Pro Gly Gln Gly Leu Lys Trp
         50                      55                      60

Met Gly Trp Ile Asn Thr Ser Thr Gly Glu Ser Thr Phe Ala Asp Asp
 65                      70                      75                      80

Phe Lys Gly Arg Phe Asp Phe Ser Leu Glu Thr Ser Ala Asn Thr Ala
                     85                      90                      95

Tyr Leu Gln Ile Asn Asn Leu Lys Ser Glu Asp Met Ala Thr Tyr Phe
                 100                     105                     110

Cys Ala Arg Trp Glu Val Tyr His Gly Tyr Val Pro Tyr Trp Gly Gln
             115                     120                     125

Gly Thr Thr Val Thr Val Ser Ser Gly Gly Gly Ser Gly Gly Gly
         130                     135                     140

Gly Ser Gly Gly Gly Ser Asp Ile Gln Leu Thr Gln Ser His Lys
145                     150                     155                     160

Phe Leu Ser Thr Ser Val Gly Asp Arg Val Ser Ile Thr Cys Lys Ala
                 165                     170                     175

Ser Gln Asp Val Tyr Asn Ala Val Ala Trp Tyr Gln Lys Pro Gly
             180                     185                     190

Gln Ser Pro Lys Leu Leu Ile Tyr Ser Ala Ser Ser Arg Tyr Thr Gly
         195                     200                     205

Val Pro Ser Arg Phe Thr Gly Ser Gly Ser Gly Pro Asp Phe Thr Phe
     210                     215                     220

Thr Ile Ser Ser Val Gln Ala Glu Asp Leu Ala Val Tyr Phe Cys Gln
225                     230                     235                     240

Gln His Phe Arg Thr Pro Phe Thr Phe Gly Ser Gly Thr Lys Leu Glu
                 245                     250                     255

Ile Lys Ala Leu Glu Gly Gly Ser Leu Ala Ala Leu Thr Ala His Gln
             260                     265                     270

Ala Cys His Leu Pro Leu Glu Thr Phe Thr Arg His Arg Gln Pro Arg
         275                     280                     285

Gly Trp Glu Gln Leu Glu Gln Cys Gly Tyr Pro Val Gln Arg Leu Val
     290                     295                     300

Ala Leu Tyr Leu Ala Ala Arg Leu Ser Trp Asn Gln Val Asp Gln Val
305                     310                     315                     320

Ile Arg Asn Ala Leu Ala Ser Pro Gly Ser Gly Gly Asp Leu Gly Glu
                 325                     330                     335

Ala Ile Arg Glu Gln Pro Glu Gln Ala Arg Leu Ala Leu Thr Leu Ala
             340                     345                     350

Ala Ala Glu Ser Glu Arg Phe Val Arg Gln Gly Thr Gly Asn Asp Glu
         355                     360                     365

Ala Gly Ala Ala Asn Ala Asp Glu Lys Leu Leu Ser Ser Ile Glu Gln
     370                     375                     380

Ala Cys Asp Ile Cys Arg Leu Lys Lys Leu Lys Cys Ser Lys Glu Lys
385                     390                     395                     400

Pro Lys Cys Ala Lys Cys Leu Lys Asn Asn Trp Glu Cys Arg Tyr Ser
                 405                     410                     415
```

-continued

```
Pro Lys Thr Lys Arg Ser Pro Leu Thr Arg Ala His Leu Thr Glu Val
        420                 425                 430

Glu Ser Arg Leu Glu Arg Leu Glu Gln Leu Phe Leu Leu Ile Phe Pro
        435                 440                 445

Arg Glu Asp Leu Asp Met Ile Leu Lys Met Asp Ser Leu Gln Asp Ile
        450                 455                 460

Lys Ala Leu Leu Thr Gly Leu Phe Val Gln Asp Asn Val Asn Lys Asp
465                 470                 475                 480

Ala Val Thr Asp Arg Leu Ala Ser Val Glu Thr Asp Met Pro Leu Thr
                485                 490                 495

Leu Arg Gln His Arg Ile Ser Ala Thr Ser Ser Ser Glu Glu Ser Ser
                500                 505                 510

Asn Lys Gly Gln Arg Gln Leu Thr Val Ser Ser Ser Asp Tyr Lys Asp
                515                 520                 525

Glu Leu
    530
```

(2) INFORMATION FOR SEQ ID NO: 3:

(i) SEQUENCE CHARACTERISTICS:
        (A) LENGTH: 1128 base pairs
        (B) TYPE: nucleic acid
        (C) STRANDEDNESS: single
        (D) TOPOLOGY: linear (ii) MOLECULE TYPE: DNA (vii) IMMEDIATE SOURCE:
        (B) CLONE: pWF47-TGF (ix) FEATURE:
        (A) NAME/KEY: CDS
        (B) LOCATION: 64..1092
        (D) OTHER INFORMATION: /partial
            /product= "TGF-alpha-delta ETA-delta GAL4 fusion
            protein"

(ix) FEATURE:
        (A) NAME/KEY: sig_peptide
        (B) LOCATION: 1..63
        (D) OTHER INFORMATION: /product= "E. coli OmpA signal
            peptide"

(xi) SEQUENCE DESCRIPTION: SEQ ID NO: 3:

```
ATGAAAAAGA CAGCTATCGC GATTGCAGTG GCACTGGCTG GTTTCGCTAC CGTTGCGCAA      60

GCT GAC TAC AAG GAC GAC GAT GAC AAG CTT GGT ACC GGT GTG GTG TCC      108
    Asp Tyr Lys Asp Asp Asp Asp Lys Leu Gly Thr Gly Val Val Ser
    1               5                   10                  15

CAT TTT AAT GAC TGC CCA GAT TCC CAC ACT CAG TTC TGC TTT CAT GGA      156
His Phe Asn Asp Cys Pro Asp Ser His Thr Gln Phe Cys Phe His Gly
                20                  25                  30

ACC TGC AGG TTT TTG GTG CAG GAG GAC AAG CCA GCA TGT GTC TGC CAT      204
Thr Cys Arg Phe Leu Val Gln Glu Asp Lys Pro Ala Cys Val Cys His
            35                  40                  45

TCT GGG TAC GTT GGT GCA CGC TGT GAG CAT GCG GAC CTC CTG GCC TCT      252
Ser Gly Tyr Val Gly Ala Arg Cys Glu His Ala Asp Leu Leu Ala Ser
        50                  55                  60

CTA GAG CAC CAT CAT CAC CAT CAC CTA GAG GGC GGC AGC CTG GCC GCG      300
Leu Glu His His His His His His Leu Glu Gly Gly Ser Leu Ala Ala
65                  70                  75

CTG ACC GCG CAC CAG GCC TGC CAC CTG CCG CTG GAG ACT TTC ACC CGT      348
Leu Thr Ala His Gln Ala Cys His Leu Pro Leu Glu Thr Phe Thr Arg
80                  85                  90                  95
```

```
CAT CGC CAG CCG CGC GGC TGG GAA CAA CTG GAG CAG TGC GGC TAT CCG        396
His Arg Gln Pro Arg Gly Trp Glu Gln Leu Glu Gln Cys Gly Tyr Pro
                100                 105                 110

GTG CAG CGG CTG GTC GCC CTC TAC CTG GCG GCG CGA CTG TCA TGG AAC        444
Val Gln Arg Leu Val Ala Leu Tyr Leu Ala Ala Arg Leu Ser Trp Asn
            115                 120                 125

CAG GTC GAC CAG GTG ATC CGC AAC GCC CTG GCC AGC CCC GGC AGC GGC        492
Gln Val Asp Gln Val Ile Arg Asn Ala Leu Ala Ser Pro Gly Ser Gly
        130                 135                 140

GGC GAC CTG GGC GAA GCG ATC CGC GAG CAG CCG GAG CAG GCC CGT CTG        540
Gly Asp Leu Gly Glu Ala Ile Arg Glu Gln Pro Glu Gln Ala Arg Leu
    145                 150                 155

GCC CTG ACC CTG GCC GCC GCC GAG AGC GAG CGC TTC GTC CGG CAG GGC        588
Ala Leu Thr Leu Ala Ala Ala Glu Ser Glu Arg Phe Val Arg Gln Gly
160                 165                 170                 175

ACC GGC AAC GAC GAG GCC GGC GCG GCC AAC GCC GAC GAG AAG CTT CTG        636
Thr Gly Asn Asp Glu Ala Gly Ala Ala Asn Ala Asp Glu Lys Leu Leu
                180                 185                 190

TCT TCT ATC GAA CAA GCA TGC GAT ATT TGC CGA CTT AAA AAG CTC AAG        684
Ser Ser Ile Glu Gln Ala Cys Asp Ile Cys Arg Leu Lys Lys Leu Lys
            195                 200                 205

TGC TCC AAA GAA AAA CCG AAG TGC GCC AAG TGT CTG AAG AAC AAC TGG        732
Cys Ser Lys Glu Lys Pro Lys Cys Ala Lys Cys Leu Lys Asn Asn Trp
        210                 215                 220

GAG TGT CGC TAC TCT CCC AAA ACC AAA AGG TCT CCG CTG ACT AGG GCA        780
Glu Cys Arg Tyr Ser Pro Lys Thr Lys Arg Ser Pro Leu Thr Arg Ala
    225                 230                 235

CAT CTG ACA GAA GTG GAA TCA AGG CTA GAA AGA CTG GAA CAG CTA TTT        828
His Leu Thr Glu Val Glu Ser Arg Leu Glu Arg Leu Glu Gln Leu Phe
240                 245                 250                 255

CTA CTG ATT TTT CCT CGA GAA GAC CTT GAC ATG ATT TTG AAA ATG GAT        876
Leu Leu Ile Phe Pro Arg Glu Asp Leu Asp Met Ile Leu Lys Met Asp
                260                 265                 270

TCT TTA CAG GAT ATA AAA GCA TTG TTA ACA GGA TTA TTT GTA CAA GAT        924
Ser Leu Gln Asp Ile Lys Ala Leu Leu Thr Gly Leu Phe Val Gln Asp
            275                 280                 285

AAT GTG AAT AAA GAT GCC GTC ACA GAT AGA TTG GCT TCA GTG GAG ACT        972
Asn Val Asn Lys Asp Ala Val Thr Asp Arg Leu Ala Ser Val Glu Thr
        290                 295                 300

GAT ATG CCT CTA ACA TTG AGA CAG CAT AGA ATA AGT GCG ACA TCA TCA       1020
Asp Met Pro Leu Thr Leu Arg Gln His Arg Ile Ser Ala Thr Ser Ser
    305                 310                 315

TCG GAA GAG AGT AGT AAC AAA GGT CAA AGA CAG TTG ACT GTA TCG AGC       1068
Ser Glu Glu Ser Ser Asn Lys Gly Gln Arg Gln Leu Thr Val Ser Ser
320                 325                 330                 335

TCT GAC TAC AAA GAC GAA CTT TAAGAATTCT CTAGAGATAT CGTCGACAGA          1119
Ser Asp Tyr Lys Asp Glu Leu
                340

TCTCTCGAG                                                              1128
```

(2) INFORMATION FOR SEQ ID NO: 4:

(i) SEQUENCE CHARACTERISTICS:
        (A) LENGTH: 342 amino acids
        (B) TYPE: amino acid
        (D) TOPOLOGY: linear (ii) MOLECULE TYPE: protein (xi) SEQUENCE DESCRIPTION: SEQ ID NO: 4:

Asp Tyr Lys Asp Asp Asp Asp Lys Leu Gly Thr Gly Val Val Ser His

```
  1               5                  10                 15
Phe Asn Asp Cys Pro Asp Ser His Thr Gln Phe Cys Phe His Gly Thr
                20                 25                 30

Cys Arg Phe Leu Val Gln Glu Asp Lys Pro Ala Cys Val Cys His Ser
            35                 40                 45

Gly Tyr Val Gly Ala Arg Cys Glu His Ala Asp Leu Leu Ala Ser Leu
        50                 55                 60

Glu His His His His His Leu Glu Gly Gly Ser Leu Ala Ala Leu
65              70                 75                     80

Thr Ala His Gln Ala Cys His Leu Pro Leu Glu Thr Phe Thr Arg His
                85                 90                     95

Arg Gln Pro Arg Gly Trp Glu Gln Leu Glu Gln Cys Gly Tyr Pro Val
            100                105                110

Gln Arg Leu Val Ala Leu Tyr Leu Ala Ala Arg Leu Ser Trp Asn Gln
            115                120                125

Val Asp Gln Val Ile Arg Asn Ala Leu Ala Ser Pro Gly Ser Gly Gly
        130                135                140

Asp Leu Gly Glu Ala Ile Arg Glu Gln Pro Glu Gln Ala Arg Leu Ala
145             150                155                    160

Leu Thr Leu Ala Ala Ala Glu Ser Glu Arg Phe Val Arg Gln Gly Thr
                165                170                175

Gly Asn Asp Glu Ala Gly Ala Ala Asn Ala Asp Glu Lys Leu Leu Ser
            180                185                190

Ser Ile Glu Gln Ala Cys Asp Ile Cys Arg Leu Lys Lys Leu Lys Cys
            195                200                205

Ser Lys Glu Lys Pro Lys Cys Ala Lys Cys Leu Lys Asn Asn Trp Glu
    210                215                220

Cys Arg Tyr Ser Pro Lys Thr Lys Arg Ser Pro Leu Thr Arg Ala His
225             230                235                    240

Leu Thr Glu Val Glu Ser Arg Leu Glu Arg Leu Glu Gln Leu Phe Leu
                245                250                255

Leu Ile Phe Pro Arg Glu Asp Leu Asp Met Ile Leu Lys Met Asp Ser
                260                265                270

Leu Gln Asp Ile Lys Ala Leu Leu Thr Gly Leu Phe Val Gln Asp Asn
            275                280                285

Val Asn Lys Asp Ala Val Thr Asp Arg Leu Ala Ser Val Glu Thr Asp
290             295                300

Met Pro Leu Thr Leu Arg Gln His Arg Ile Ser Ala Thr Ser Ser Ser
305             310                315                    320

Glu Glu Ser Ser Asn Lys Gly Gln Arg Gln Leu Thr Val Ser Ser Ser
            325                330                335

Asp Tyr Lys Asp Glu Leu
            340
```

(2) INFORMATION FOR SEQ ID NO: 5:

(i) SEQUENCE CHARACTERISTICS:
        (A) LENGTH: 1365 base pairs
        (B) TYPE: nucleic acid
        (C) STRANDEDNESS: single
        (D) TOPOLOGY: linear (ii) MOLECULE TYPE: DNA (vii) IMMEDIATE SOURCE:
        (B) CLONE: pWF46-IL-2

-continued

```
    (ix) FEATURE:
         (A) NAME/KEY: sig_peptide
         (B) LOCATION: 1..63

(ix) FEATURE:
         (A) NAME/KEY: CDS
         (B) LOCATION: 64..1329
         (D) OTHER INFORMATION: /product= "IL-2-deltaETA-deltaGAL4"

(xi) SEQUENCE DESCRIPTION: SEQ ID NO: 5:
```

| | | | | | | |
|---|---|---|---|---|---|---|
| ATGAAAAAGA | CAGCTATCGC | GATTGCAGTG | GCACTGGCTG | GTTTCGCTAC | CGTTGCGCAA | 60 |

| GCT | TAC | AAG | GAC | GAC | GAT | GAC | AAG | CTG | CAC | CAT | CAT | CAC | CAT | CAC | 108 |
|---|---|---|---|---|---|---|---|---|---|---|---|---|---|---|---|
| Asp | Tyr | Lys | Asp | Asp | Asp | Asp | Lys | Leu | His | His | His | His | His | His | |
| 1 | | | | 5 | | | | | 10 | | | | | 15 | |

| AAG | CTT | GCA | CCT | ACT | TCA | AGT | TCT | ACA | AAG | AAA | ACA | CAG | CTA | CAA | CTG | 156 |
|---|---|---|---|---|---|---|---|---|---|---|---|---|---|---|---|---|
| Lys | Leu | Ala | Pro | Thr | Ser | Ser | Ser | Thr | Lys | Lys | Thr | Gln | Leu | Gln | Leu | |
| | | | | 20 | | | | | 25 | | | | | 30 | | |

| GAG | CAT | TTA | CTG | CTG | GAT | TTA | CAG | ATG | ATT | TTG | AAT | GGA | ATT | AAT | AAT | 204 |
|---|---|---|---|---|---|---|---|---|---|---|---|---|---|---|---|---|
| Glu | His | Leu | Leu | Leu | Asp | Leu | Gln | Met | Ile | Leu | Asn | Gly | Ile | Asn | Asn | |
| | | 35 | | | | | 40 | | | | | 45 | | | | |

| TAC | AAG | AAT | CCC | AAA | CTC | ACC | AGG | ATG | CTC | ACA | TTT | AAG | TTT | TAC | ATG | 252 |
|---|---|---|---|---|---|---|---|---|---|---|---|---|---|---|---|---|
| Tyr | Lys | Asn | Pro | Lys | Leu | Thr | Arg | Met | Leu | Thr | Phe | Lys | Phe | Tyr | Met | |
| 50 | | | | | 55 | | | | | 60 | | | | | | |

| CCC | AAG | AAG | GCC | ACA | GAA | CTG | AAA | CAT | CTT | CAG | TGT | CTA | GAA | GAA | GAA | 300 |
|---|---|---|---|---|---|---|---|---|---|---|---|---|---|---|---|---|
| Pro | Lys | Lys | Ala | Thr | Glu | Leu | Lys | His | Leu | Gln | Cys | Leu | Glu | Glu | Glu | |
| 65 | | | | | 70 | | | | | 75 | | | | | | |

| CTC | AAA | CCT | CTG | GAG | GAA | GTG | CTA | AAT | TTA | GCT | CAA | AGC | AAA | AAC | TTT | 348 |
|---|---|---|---|---|---|---|---|---|---|---|---|---|---|---|---|---|
| Leu | Lys | Pro | Leu | Glu | Glu | Val | Leu | Asn | Leu | Ala | Gln | Ser | Lys | Asn | Phe | |
| 80 | | | | | 85 | | | | | 90 | | | | | 95 | |

| CAC | TTA | AGA | CCC | AGG | GAC | TTA | ATC | AGC | AAT | ATC | AAC | GTA | ATA | GTT | CTG | 396 |
|---|---|---|---|---|---|---|---|---|---|---|---|---|---|---|---|---|
| His | Leu | Arg | Pro | Arg | Asp | Leu | Ile | Ser | Asn | Ile | Asn | Val | Ile | Val | Leu | |
| | | | | 100 | | | | | 105 | | | | | 110 | | |

| GAA | CTA | AAG | GGA | TCT | GAA | ACA | ACA | TTC | ATG | TGT | GAA | TAT | GCT | GAT | GAG | 444 |
|---|---|---|---|---|---|---|---|---|---|---|---|---|---|---|---|---|
| Glu | Leu | Lys | Gly | Ser | Glu | Thr | Thr | Phe | Met | Cys | Glu | Tyr | Ala | Asp | Glu | |
| | | | 115 | | | | | 120 | | | | | 125 | | | |

| ACA | GCA | ACC | ATT | GTA | GAA | TTT | CTG | AAC | AGA | TGG | ATT | ACC | TTT | TGT | CAA | 492 |
|---|---|---|---|---|---|---|---|---|---|---|---|---|---|---|---|---|
| Thr | Ala | Thr | Ile | Val | Glu | Phe | Leu | Asn | Arg | Trp | Ile | Thr | Phe | Cys | Gln | |
| | | 130 | | | | | 135 | | | | | 140 | | | | |

| AGC | ATC | ATC | TCA | ACA | CTA | ACG | CTA | GAG | GGC | GGC | AGC | CTG | GCC | GCG | CTG | 540 |
|---|---|---|---|---|---|---|---|---|---|---|---|---|---|---|---|---|
| Ser | Ile | Ile | Ser | Thr | Leu | Thr | Leu | Glu | Gly | Gly | Ser | Leu | Ala | Ala | Leu | |
| 145 | | | | | 150 | | | | | 155 | | | | | | |

| ACC | GCG | CAC | CAG | GCC | TGC | CAC | CTG | CCG | CTG | GAG | ACT | TTC | ACC | CGT | CAT | 588 |
|---|---|---|---|---|---|---|---|---|---|---|---|---|---|---|---|---|
| Thr | Ala | His | Gln | Ala | Cys | His | Leu | Pro | Leu | Glu | Thr | Phe | Thr | Arg | His | |
| 160 | | | | | 165 | | | | | 170 | | | | | 175 | |

| CGC | CAG | CCG | CGC | GGC | TGG | GAA | CAA | CTG | GAG | CAG | TGC | GGC | TAT | CCG | GTG | 636 |
|---|---|---|---|---|---|---|---|---|---|---|---|---|---|---|---|---|
| Arg | Gln | Pro | Arg | Gly | Trp | Glu | Gln | Leu | Glu | Gln | Cys | Gly | Tyr | Pro | Val | |
| | | | | 180 | | | | | 185 | | | | | 190 | | |

| CAG | CGG | CTG | GTC | GCC | CTC | TAC | CTG | GCG | GCG | CGA | CTG | TCA | TGG | AAC | CAG | 684 |
|---|---|---|---|---|---|---|---|---|---|---|---|---|---|---|---|---|
| Gln | Arg | Leu | Val | Ala | Leu | Tyr | Leu | Ala | Ala | Arg | Leu | Ser | Trp | Asn | Gln | |
| | | | 195 | | | | | 200 | | | | | 205 | | | |

| GTC | GAC | CAG | GTG | ATC | CGC | AAC | GCC | CTG | GCC | AGC | CCC | GGC | AGC | GGC | GGC | 732 |
|---|---|---|---|---|---|---|---|---|---|---|---|---|---|---|---|---|
| Val | Asp | Gln | Val | Ile | Arg | Asn | Ala | Leu | Ala | Ser | Pro | Gly | Ser | Gly | Gly | |
| | | 210 | | | | | 215 | | | | | 220 | | | | |

| GAC | CTG | GGC | GAA | GCG | ATC | CGC | GAG | CAG | CCG | GAG | CAG | GCC | CGT | CTG | GCC | 780 |
|---|---|---|---|---|---|---|---|---|---|---|---|---|---|---|---|---|
| Asp | Leu | Gly | Glu | Ala | Ile | Arg | Glu | Gln | Pro | Glu | Gln | Ala | Arg | Leu | Ala | |
| 225 | | | | | 230 | | | | | 235 | | | | | | |

| CTG | ACC | CTG | GCC | GCC | GCC | GAG | AGC | GAG | CGC | TTC | GTC | CGG | CAG | GGC | ACC | 828 |
|---|---|---|---|---|---|---|---|---|---|---|---|---|---|---|---|---|
| Leu | Thr | Leu | Ala | Ala | Ala | Glu | Ser | Glu | Arg | Phe | Val | Arg | Gln | Gly | Thr | |
| 240 | | | | | 245 | | | | | 250 | | | | | 255 | |

| GGC | AAC | GAC | GAG | GCC | GGC | GCG | GCC | AAC | GCC | GAC | GAG | AAG | CTT | CTG | TCT | 876 |
|---|---|---|---|---|---|---|---|---|---|---|---|---|---|---|---|---|
| Gly | Asn | Asp | Glu | Ala | Gly | Ala | Ala | Asn | Ala | Asp | Glu | Lys | Leu | Leu | Ser | |

-continued

```
                260                 265                 270
TCT ATC GAA CAA GCA TGC GAT ATT TGC CGA CTT AAA AAG CTC AAG TGC      924
Ser Ile Glu Gln Ala Cys Asp Ile Cys Arg Leu Lys Lys Leu Lys Cys
            275                 280                 285

TCC AAA GAA AAA CCG AAG TGC GCC AAG TGT CTG AAG AAC AAC TGG GAG      972
Ser Lys Glu Lys Pro Lys Cys Ala Lys Cys Leu Lys Asn Asn Trp Glu
            290                 295                 300

TGT CGC TAC TCT CCC AAA ACC AAA AGG TCT CCG CTG ACT AGG GCA CAT     1020
Cys Arg Tyr Ser Pro Lys Thr Lys Arg Ser Pro Leu Thr Arg Ala His
    305                 310                 315

CTG ACA GAA GTG GAA TCA AGG CTA GAA AGA CTG GAA CAG CTA TTT CTA     1068
Leu Thr Glu Val Glu Ser Arg Leu Glu Arg Leu Glu Gln Leu Phe Leu
320                 325                 330                 335

CTG ATT TTT CCT CGA GAA GAC CTT GAC ATG ATT TTG AAA ATG GAT TCT     1116
Leu Ile Phe Pro Arg Glu Asp Leu Asp Met Ile Leu Lys Met Asp Ser
                340                 345                 350

TTA CAG GAT ATA AAA GCA TTG TTA ACA GGA TTA TTT GTA CAA GAT AAT     1164
Leu Gln Asp Ile Lys Ala Leu Leu Thr Gly Leu Phe Val Gln Asp Asn
            355                 360                 365

GTG AAT AAA GAT GCC GTC ACA GAT AGA TTG GCT TCA GTG GAG ACT GAT     1212
Val Asn Lys Asp Ala Val Thr Asp Arg Leu Ala Ser Val Glu Thr Asp
        370                 375                 380

ATG CCT CTA ACA TTG AGA CAG CAT AGA ATA AGT GCG ACA TCA TCA TCG     1260
Met Pro Leu Thr Leu Arg Gln His Arg Ile Ser Ala Thr Ser Ser Ser
385                 390                 395

GAA GAG AGT AGT AAC AAA GGT CAA AGA CAG TTG ACT GTA TCG AGC TCT     1308
Glu Glu Ser Ser Asn Lys Gly Gln Arg Gln Leu Thr Val Ser Ser Ser
400                 405                 410                 415

GAC TAC AAA GAC GAA CTT TAAGAATTCT CTAGAGATAT CGTCGACAGA TCTCTCGAG  1365
Asp Tyr Lys Asp Glu Leu
                420
```

(2) INFORMATION FOR SEQ ID NO: 6:

(i) SEQUENCE CHARACTERISTICS:
        (A) LENGTH: 421 amino acids
        (B) TYPE: amino acid
        (D) TOPOLOGY: linear (ii) MOLECULE TYPE: protein (xi) SEQUENCE DESCRIPTION: SEQ ID NO: 6:

```
Asp Tyr Lys Asp Asp Asp Asp Lys Leu His His His His His Lys
1               5                   10                  15

Leu Ala Pro Thr Ser Ser Thr Lys Lys Thr Gln Leu Gln Leu Glu
            20                  25                  30

His Leu Leu Leu Asp Leu Gln Met Ile Leu Asn Gly Ile Asn Asn Tyr
        35                  40                  45

Lys Asn Pro Lys Leu Thr Arg Met Leu Thr Phe Lys Phe Tyr Met Pro
    50                  55                  60

Lys Lys Ala Thr Glu Leu Lys His Leu Gln Cys Leu Glu Glu Glu Leu
65                  70                  75                  80

Lys Pro Leu Glu Glu Val Leu Asn Leu Ala Gln Ser Lys Asn Phe His
            85                  90                  95

Leu Arg Pro Arg Asp Leu Ile Ser Asn Ile Asn Val Ile Val Leu Glu
        100                 105                 110

Leu Lys Gly Ser Glu Thr Thr Phe Met Cys Glu Tyr Ala Asp Glu Thr
    115                 120                 125

Ala Thr Ile Val Glu Phe Leu Asn Arg Trp Ile Thr Phe Cys Gln Ser
```

```
            130                 135                 140
Ile Ile Ser Thr Leu Thr Leu Glu Gly Gly Ser Leu Ala Ala Leu Thr
145                 150                 155                 160
Ala His Gln Ala Cys His Leu Pro Leu Glu Thr Phe Thr Arg His Arg
                165                 170                 175
Gln Pro Arg Gly Trp Glu Gln Leu Glu Gln Cys Gly Tyr Pro Val Gln
            180                 185                 190
Arg Leu Val Ala Leu Tyr Leu Ala Ala Arg Leu Ser Trp Asn Gln Val
        195                 200                 205
 Asp Gln Val Ile Arg Asn Ala Leu Ala Ser Pro Gly Ser Gly Gly Asp
    210                 215                 220
Leu Gly Glu Ala Ile Arg Glu Gln Pro Glu Gln Ala Arg Leu Ala Leu
225                 230                 235                 240
Thr Leu Ala Ala Ala Glu Ser Glu Arg Phe Val Arg Gln Gly Thr Gly
                245                 250                 255
Asn Asp Glu Ala Gly Ala Ala Asn Ala Asp Glu Lys Leu Leu Ser Ser
            260                 265                 270
Ile Glu Gln Ala Cys Asp Ile Cys Arg Leu Lys Lys Leu Lys Cys Ser
        275                 280                 285
Lys Glu Lys Pro Lys Cys Ala Lys Cys Leu Lys Asn Asn Trp Glu Cys
290                 295                 300
Arg Tyr Ser Pro Lys Thr Lys Arg Ser Pro Leu Thr Arg Ala His Leu
305                 310                 315                 320
Thr Glu Val Glu Ser Arg Leu Glu Arg Leu Glu Gln Leu Phe Leu Leu
                325                 330                 335
Ile Phe Pro Arg Glu Asp Leu Asp Met Ile Leu Lys Met Asp Ser Leu
            340                 345                 350
Gln Asp Ile Lys Ala Leu Leu Thr Gly Leu Phe Val Gln Asp Asn Val
        355                 360                 365
Asn Lys Asp Ala Val Thr Asp Arg Leu Ala Ser Val Glu Thr Asp Met
370                 375                 380
Pro Leu Thr Leu Arg Gln His Arg Ile Ser Ala Thr Ser Ser Ser Glu
385                 390                 395                 400
Glu Ser Ser Asn Lys Gly Gln Arg Gln Leu Thr Val Ser Ser Ser Asp
                405                 410                 415
Tyr Lys Asp Glu Leu
            420

(2) INFORMATION FOR SEQ ID NO: 7:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 7:

CGAGAAGCTT GAGAGCTCTG ACTACAAAGA CGAACTTTAA G                  41

(2) INFORMATION FOR SEQ ID NO: 8:

(i) SEQUENCE CHARACTERISTICS:
        (A) LENGTH: 43 base pairs
        (B) TYPE: nucleic acid
        (C) STRANDEDNESS: single
        (D) TOPOLOGY: linear
```

(ii) MOLECULE TYPE: DNA (xi) SEQUENCE DESCRIPTION: SEQ ID NO: 8:

AATTCTTAAA GTTCGTCTTT GTAGTCAGAG CTCTCAAGCT TCT                         43

(2) INFORMATION FOR SEQ ID NO: 9:

(i) SEQUENCE CHARACTERISTICS:
                (A) LENGTH: 394 base pairs
                (B) TYPE: nucleic acid
                (C) STRANDEDNESS: single
                (D) TOPOLOGY: linear (ii) MOLECULE TYPE: DNA (vii) IMMEDIATE SOURCE:
                (B) CLONE: pWW 25

(xi) SEQUENCE DESCRIPTION: SEQ ID NO: 9:

TCTAGAGGGC GGCAGCCTGG CCGCGCTGAC CGCGCACCAG GCCTGCCACC TGCCGCTGGA        60

GACTTTCACC CGTCATCGCC AGCCGCGCGG CTGGGAACAA CTGGAGCAGT GCGGCTATCC       120

GGTGCAGCGG CTGGTCGCCC TCTACCTGGC GGCGCGACTG TCATGGAACC AGGTCGACCA       180

GGTGATCCGC AACGCCCTGG CCAGCCCCGG CAGCGGCGGC GACCTGGGCG AAGCGATCCG       240

CGAGCAGCCG GAGCAGGCCC GTCTGGCCCT GACCCTGGCC GCCGCCGAGA GCGAGCGCTT       300

CGTCCGGCAG GGCACCGGCA ACGACGAGGC CGGCGCGGCC AACGCCGACG AGAAGCTTGA       360

GAGCTCTGAC TACAAAGACG AACTTTAAGA ATTC                                  394

(2) INFORMATION FOR SEQ ID NO: 10:

(i) SEQUENCE CHARACTERISTICS:
                (A) LENGTH: 20 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO: 10:

CAGATGAAGC TTCTGTCTTC                                                   20

(2) INFORMATION FOR SEQ ID NO: 11:

(i) SEQUENCE CHARACTERISTICS:
                (A) LENGTH: 24 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO: 11:

GAATGAGCTC GATACAGTCA ACTG                                              24

(2) INFORMATION FOR SEQ ID NO: 12:

(i) SEQUENCE CHARACTERISTICS:
                (A) LENGTH: 443 base pairs
                (B) TYPE: nucleic acid
                (C) STRANDEDNESS: single
                (D) TOPOLOGY: linear (ii) MOLECULE TYPE: DNA (vii) IMMEDIATE SOURCE:

(B) CLONE: pWW35

(xi) SEQUENCE DESCRIPTION: SEQ ID NO: 12:

AAGCTTCTGT CTTCTATCGA ACAAGCATGC GATATTTGCC GACTTAAAAA GCTCAAGTGC     60

TCCAAAGAAA AACCGAAGTG CGCCAAGTGT CTGAAGAACA ACTGGGAGTG TCGCTACTCT    120

CCCAAAACCA AAAGGTCTCC GCTGACTAGG GCACATCTGA CAGAAGTGGA ATCAAGGCTA    180

GAAAGACTGG AACAGCTATT TCTACTGATT TTTCCTCGAG AAGACCTTGA CATGATTTTG    240

AAAATGGATT CTTTACAGGA TATAAAAGCA TTGTTAACAG GATTATTTGT ACAAGATAAT    300

GTGAATAAAG ATGCCGTCAC AGATAGATTG GCTTCAGTGG AGACTGATAT GCCTCTAACA    360

TTGAGACAGC ATAGAATAAG TGCGACATCA TCATCGGAAG AGAGTAGTAA CAAAGGTCAA    420

AGACAGTTGA CTGTATCGAG CTC                                            443

(2) INFORMATION FOR SEQ ID NO: 13:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 13:

TCACTGGATG GTGGGAAGAT GGA                                             23

(2) INFORMATION FOR SEQ ID NO: 14:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 14:

AGATCCAGGG GCCAGTGGAT AGA                                             23

(2) INFORMATION FOR SEQ ID NO: 15:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 15:

CAAGCTTCTC AGGTACAACT GCAGGAGGTC ACCGTTTCCT CTGGCGG                   47

(2) INFORMATION FOR SEQ ID NO: 16:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 16:

GAAACGGTGA CCTCCTGCAG TTGTACCTGA GAAGCTTGCA TG                        42

(2) INFORMATION FOR SEQ ID NO: 17:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 17:

```
TGGCGGTTCT GGTGGCGGTG GCTCCGGCGG TGGCGGTTCT GAC          43
```

(2) INFORMATION FOR SEQ ID NO: 18:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 18:

```
GCCACCGCCG AGCCACCGC CACCAGAACC GCCACCGCCA GAG            43
```

(2) INFORMATION FOR SEQ ID NO: 19:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 19:

```
ATCCAGCTGG AGATCTAGCT GATCAAAGCT                         30
```

(2) INFORMATION FOR SEQ ID NO: 20:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 20:

```
CTAGAGCTTT GATCAGCTAG ATCTCCAGCT GGATGTCAGA ACC          43
```

(2) INFORMATION FOR SEQ ID NO: 21:

(i) SEQUENCE CHARACTERISTICS:
        (A) LENGTH: 175 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 21:

```
AAGCTTGCAT GCAAGCTTCT CAGGTACAAC TGCAGGAGGT CACCGTTTCC TCTGGCGGTG    60
GCGGTTCTGG TGGCGGTGGC TCCGGCGGTG GCGGTTCTGA CATCCAGCTG GAGATCTAGC   120
TGATCAAAGC TCTAGAGGAT CCCCGGGTAC CGAGCTCGAA TTCACTGGCC GTCGT        175
```

(2) INFORMATION FOR SEQ ID NO: 22:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 22:

GACATTCAGC TGACCCAG                                                18

(2) INFORMATION FOR SEQ ID NO: 23:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 23:

GCCCGTTAGA TCTCCAATTT TGTCCCCGAG                             30

(2) INFORMATION FOR SEQ ID NO: 24:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 24:

ACAAAATTGG AGATCAAAGC TCTAGA                                 26

(2) INFORMATION FOR SEQ ID NO: 25:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 25:

AGCTTCAGGT ACAACTGCA                                               19

(2) INFORMATION FOR SEQ ID NO: 26:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 26:

GTTGTACCTG A                                                             11

(2) INFORMATION FOR SEQ ID NO: 27:

(i) SEQUENCE CHARACTERISTICS:
            (A) LENGTH: 48 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 27:

AGCTTGGATC CGGAGGACAG TCCTCCGGAG ACCGGAGGAC AGTCCTCC                     48

(2) INFORMATION FOR SEQ ID NO: 28:

(i) SEQUENCE CHARACTERISTICS:
            (A) LENGTH: 48 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 28:

GATCGGAGGA CTGTCCTCCG GTCTCCGGAG GACTGTCCTC CGGATCCA                     48

(2) INFORMATION FOR SEQ ID NO: 29:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 29:

GACCCGAAGC TTGGTACCGG TGTGGTGTCC CATTTTAATG                              40

(2) INFORMATION FOR SEQ ID NO: 30:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 30:

TTCTGGGAGC TCTCTAGAGA GGCCAGGAGG TCCGC                                   35

(2) INFORMATION FOR SEQ ID NO: 31:

(i) SEQUENCE CHARACTERISTICS:
            (A) LENGTH: 173 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 31:

AAGCTTGGTA CCGGTGTGGT GTCCCATTTT AATGACTGCC CAGATTCCCA CACTCAGTTC        60

TGCTTTCATG GAACCTGCAG GTTTTTGGTG CAGGAGGACA AGCCAGCATG TGTCTGCCAT        120

TCTGGGTACG TTGGTGCACG CTGTGAGCAT GCGGACCTCC TGGCCTCTCT AGA              173

(2) INFORMATION FOR SEQ ID NO: 32:

```
    (i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 32:

TATAATAAGC TTGCACCTAC TTCAAG                                            26

(2) INFORMATION FOR SEQ ID NO: 33:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 33:

TTGAATGCTA GCGTTAGTGT TGAGATG                                           27

(2) INFORMATION FOR SEQ ID NO: 34:

(i) SEQUENCE CHARACTERISTICS:
        (A) LENGTH: 1919 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 64..1908

(xi) SEQUENCE DESCRIPTION: SEQ ID NO: 34:

ATGAAAAAGA CAGCTATCGC GATTGCAGTG GCACTGGCTG GTTTCGCTAC CGTTGCGCAA        60

GCT GAC TAC AAG GAC GAC GAT GAC AAG CTG CAC CAT CAT CAC CAT CAC        108
    Asp Tyr Lys Asp Asp Asp Asp Lys Leu His His His His His His
    1               5                  10                  15

AAG CTT CTG TCT TCT ATC GAA CAA GCA TGC GAT ATT TGC CGA CTT AAA        156
Lys Leu Leu Ser Ser Ile Glu Gln Ala Cys Asp Ile Cys Arg Leu Lys
                20                  25                  30

AAG CTC AAG TGC TCC AAA GAA AAA CCG AAG TGC GCC AAG TGT CTG AAG        204
Lys Leu Lys Cys Ser Lys Glu Lys Pro Lys Cys Ala Lys Cys Leu Lys
                35                  40                  45

AAC AAC TGG GAG TGT CGC TAC TCT CCC AAA ACC AAA AGG TCT CCG CTG        252
Asn Asn Trp Glu Cys Arg Tyr Ser Pro Lys Thr Lys Arg Ser Pro Leu
        50                  55                  60

ACT AGG GCA CAT CTG ACA GAA GTG GAA TCA AGG CTA GAA AGA CTG GAA        300
Thr Arg Ala His Leu Thr Glu Val Glu Ser Arg Leu Glu Arg Leu Glu
        65                  70                  75

CAG CTA TTT CTA CTG ATT TTT CCT CGA GAA GAC CTT GAC ATG ATT TTG        348
Gln Leu Phe Leu Leu Ile Phe Pro Arg Glu Asp Leu Asp Met Ile Leu
80                  85                  90                  95

AAA ATG GAT TCT TTA CAG GAT ATA AAA GCA TTG TTA ACA GGA TTA TTT        396
Lys Met Asp Ser Leu Gln Asp Ile Lys Ala Leu Leu Thr Gly Leu Phe
                100                 105                 110

GTA CAA GAT AAT GTG AAT AAA GAT GCC GTC ACA GAT AGA TTG GCT TCA        444
Val Gln Asp Asn Val Asn Lys Asp Ala Val Thr Asp Arg Leu Ala Ser
            115                 120                 125

GTG GAG ACT GAT ATG CCT CTA ACA TTG AGA CAG CAT AGA ATA AGT GCG        492
```

```
Val Glu Thr Asp Met Pro Leu Thr Leu Arg Gln His Arg Ile Ser Ala
    130                 135                 140

ACA TCA TCA TCG GAA GAG AGT AGT AAC AAA GGT CAA AGA CAG TTG ACT        540
Thr Ser Ser Ser Glu Glu Ser Ser Asn Lys Gly Gln Arg Gln Leu Thr
145                 150                 155

GTA TCG AGC TCG CTA GCA GTA GGT AGC TCA TTG TCA TGC ATC AAC CTC        588
Val Ser Ser Ser Leu Ala Val Gly Ser Ser Leu Ser Cys Ile Asn Leu
160                 165                 170                 175

GAT TGG GAT GTT ATC CGT GAT AAA ACT AAA ACT AAG ATC GAA TCT CTG        636
Asp Trp Asp Val Ile Arg Asp Lys Thr Lys Thr Lys Ile Glu Ser Leu
                180                 185                 190

AAA GAA CAC GGT CCG ATC AAA AAC AAA ATG AGC GAA AGC CCG AAC AAA        684
Lys Glu His Gly Pro Ile Lys Asn Lys Met Ser Glu Ser Pro Asn Lys
            195                 200                 205

ACT GTA TCT GAA GAA AAA GCT AAA CAG TAC CTG GAA GAA TTC CAC CAG        732
Thr Val Ser Glu Glu Lys Ala Lys Gln Tyr Leu Glu Glu Phe His Gln
        210                 215                 220

ACT GCA CTG GAA CAC CCG GAA CTG TCT GAA CTT AAG ACC GTT ACT GGT        780
Thr Ala Leu Glu His Pro Glu Leu Ser Glu Leu Lys Thr Val Thr Gly
    225                 230                 235

ACC AAC CCG GTA TTC GCT GGT GCT AAC TAC GCT GCT TGG GCA GTA AAC        828
Thr Asn Pro Val Phe Ala Gly Ala Asn Tyr Ala Ala Trp Ala Val Asn
240                 245                 250                 255

GTT GCT CAG GTT ATC GAT AGC GAA ACT GCT GAT AAC CTG GAA AAA ACT        876
Val Ala Gln Val Ile Asp Ser Glu Thr Ala Asp Asn Leu Glu Lys Thr
                260                 265                 270

ACC GCG GCT CTG TCT ATC CTG CCG GGT ATC GGT AGC GTA ATG GGC ATC        924
Thr Ala Ala Leu Ser Ile Leu Pro Gly Ile Gly Ser Val Met Gly Ile
            275                 280                 285

GCA GAC GGC GCC GTT CAC CAC AAC ACT GAA GAA ATC GTT GCA CAG TCT        972
Ala Asp Gly Ala Val His His Asn Thr Glu Glu Ile Val Ala Gln Ser
        290                 295                 300

ATC GCT CTG AGC TCT CTG ATG GTT GCT CAG GCC ATC CCG CTG GTA GGT       1020
Ile Ala Leu Ser Ser Leu Met Val Ala Gln Ala Ile Pro Leu Val Gly
    305                 310                 315

GAA CTG GTT GAT ATC GGT TTC GCT GCA TAC AAC TTC GTT GAA AGC ATC       1068
Glu Leu Val Asp Ile Gly Phe Ala Ala Tyr Asn Phe Val Glu Ser Ile
320                 325                 330                 335

ATC AAC CTG TTC CAG GTT GTT CAC AAC TCT TAC AAC CGC CCG GCT TAC       1116
Ile Asn Leu Phe Gln Val Val His Asn Ser Tyr Asn Arg Pro Ala Tyr
                340                 345                 350

TCT CCG GGT GTC GAC GGT ATC GAT AAG CTT CAG GTA CAA CTG CAG CAG       1164
Ser Pro Gly Val Asp Gly Ile Asp Lys Leu Gln Val Gln Leu Gln Gln
            355                 360                 365

TCT GGA CCT GAA CTG AAG AAG CCT GGA GAG ACA GTC AAG ATC TCC TGC       1212
Ser Gly Pro Glu Leu Lys Lys Pro Gly Glu Thr Val Lys Ile Ser Cys
        370                 375                 380

AAG GCC TCT GGG TAT CCT TTC ACA AAC TAT GGA ATG AAC TGG GTG AAG       1260
Lys Ala Ser Gly Tyr Pro Phe Thr Asn Tyr Gly Met Asn Trp Val Lys
    385                 390                 395

CAG GCT CCA GGA CAG GGT TTA AAG TGG ATG GGC TGG ATT AAC ACC TCC       1308
Gln Ala Pro Gly Gln Gly Leu Lys Trp Met Gly Trp Ile Asn Thr Ser
400                 405                 410                 415

ACT GGA GAG TCA ACA TTT GCT GAT GAC TTC AAG GGA CGG TTT GAC TTC       1356
Thr Gly Glu Ser Thr Phe Ala Asp Asp Phe Lys Gly Arg Phe Asp Phe
                420                 425                 430

TCT TTG GAA ACC TCT GCC AAC ACT GCC TAT TTG CAG ATC AAC AAC CTC       1404
Ser Leu Glu Thr Ser Ala Asn Thr Ala Tyr Leu Gln Ile Asn Asn Leu
            435                 440                 445
```

```
AAA AGT GAA GAC ATG GCT ACA TAT TTC TGT GCA AGA TGG GAG GTT TAC    1452
Lys Ser Glu Asp Met Ala Thr Tyr Phe Cys Ala Arg Trp Glu Val Tyr
        450                 455                 460

CAC GGC TAC GTT CCT TAC TGG GGC CAA GGG ACC ACG GTC ACC GTT TCC    1500
His Gly Tyr Val Pro Tyr Trp Gly Gln Gly Thr Thr Val Thr Val Ser
465                 470                 475

TCT GGC GGT GGC GGT TCT GGT GGC GGT GGC TCC GGC GGT GGC GGT TCT    1548
Ser Gly Gly Gly Gly Ser Gly Gly Gly Gly Ser Gly Gly Gly Gly Ser
480                 485                 490                 495

GAC ATC CAG CTG ACC CAG TCT CAC AAA TTC CTG TCC ACT TCA GTA GGA    1596
Asp Ile Gln Leu Thr Gln Ser His Lys Phe Leu Ser Thr Ser Val Gly
                500                 505                 510

GAC AGG GTC AGC ATC ACC TGC AAG GCC AGT CAG GAT GTG TAT AAT GCT    1644
Asp Arg Val Ser Ile Thr Cys Lys Ala Ser Gln Asp Val Tyr Asn Ala
            515                 520                 525

GTT GCC TGG TAT CAA CAG AAA CCA GGA CAA TCT CCT AAA CTT CTG ATT    1692
Val Ala Trp Tyr Gln Gln Lys Pro Gly Gln Ser Pro Lys Leu Leu Ile
        530                 535                 540

TAC TCG GCA TCC TCC CGG TAC ACT GGA GTC CCT TCT CGC TTC ACT GGC    1740
Tyr Ser Ala Ser Ser Arg Tyr Thr Gly Val Pro Ser Arg Phe Thr Gly
    545                 550                 555

AGT GGC TCT GGG CCG GAT TTC ACT TTC ACC ATC AGC AGT GTG CAG GCT    1788
Ser Gly Ser Gly Pro Asp Phe Thr Phe Thr Ile Ser Ser Val Gln Ala
560                 565                 570                 575

GAA GAC CTG GCA GTT TAT TTC TGT CAG CAA CAT TTT CGT ACT CCA TTC    1836
Glu Asp Leu Ala Val Tyr Phe Cys Gln Gln His Phe Arg Thr Pro Phe
                580                 585                 590

ACG TTC GGC TCG GGG ACA AAA TTG GAG ATC AAA GCT CTA GAG GAT CTC    1884
Thr Phe Gly Ser Gly Thr Lys Leu Glu Ile Lys Ala Leu Glu Asp Leu
            595                 600                 605

TCG AGT GAG AGA AGA TTT TCA GCC TGATACAGAT T                       1919
Ser Ser Glu Arg Arg Phe Ser Ala
        610                 615
```

(2) INFORMATION FOR SEQ ID NO: 35:

(i) SEQUENCE CHARACTERISTICS:
        (A) LENGTH: 615 amino acids
        (B) TYPE: amino acid
        (D) TOPOLOGY: linear (ii) MOLECULE TYPE: protein (xi) SEQUENCE DESCRIPTION: SEQ ID NO: 35:

```
Asp Tyr Lys Asp Asp Asp Lys Leu His His His His His His Lys
1               5                   10                  15

Leu Leu Ser Ser Ile Glu Gln Ala Cys Asp Ile Cys Arg Leu Lys Lys
            20                  25                  30

Leu Lys Cys Ser Lys Glu Lys Pro Lys Cys Ala Lys Cys Leu Lys Asn
        35                  40                  45

Asn Trp Glu Cys Arg Tyr Ser Pro Lys Thr Lys Arg Ser Pro Leu Thr
    50                  55                  60

Arg Ala His Leu Thr Glu Val Glu Ser Arg Leu Glu Arg Leu Glu Gln
65                  70                  75                  80

Leu Phe Leu Leu Ile Phe Pro Arg Glu Asp Leu Asp Met Ile Leu Lys
                85                  90                  95

Met Asp Ser Leu Gln Asp Ile Lys Ala Leu Leu Thr Gly Leu Phe Val
            100                 105                 110

Gln Asp Asn Val Asn Lys Asp Ala Val Thr Asp Arg Leu Ala Ser Val
        115                 120                 125
```

-continued

```
Glu Thr Asp Met Pro Leu Thr Leu Arg Gln His Arg Ile Ser Ala Thr
    130                 135                 140
Ser Ser Ser Glu Glu Ser Ser Asn Lys Gly Gln Arg Gln Leu Thr Val
145                 150                 155                 160
Ser Ser Ser Leu Ala Val Gly Ser Ser Leu Ser Cys Ile Asn Leu Asp
            165                 170                 175
Trp Asp Val Ile Arg Asp Lys Thr Lys Thr Lys Ile Glu Ser Leu Lys
                180                 185                 190
Glu His Gly Pro Ile Lys Asn Lys Met Ser Glu Ser Pro Asn Lys Thr
            195                 200                 205
Val Ser Glu Glu Lys Ala Lys Gln Tyr Leu Glu Glu Phe His Gln Thr
210                 215                 220
Ala Leu Glu His Pro Glu Leu Ser Glu Leu Lys Thr Val Thr Gly Thr
225                 230                 235                 240
Asn Pro Val Phe Ala Gly Ala Asn Tyr Ala Ala Trp Ala Val Asn Val
                245                 250                 255
Ala Gln Val Ile Asp Ser Glu Thr Ala Asp Asn Leu Glu Lys Thr Thr
                260                 265                 270
Ala Ala Leu Ser Ile Leu Pro Gly Ile Gly Ser Val Met Gly Ile Ala
            275                 280                 285
Asp Gly Ala Val His His Asn Thr Glu Glu Ile Val Ala Gln Ser Ile
290                 295                 300
Ala Leu Ser Ser Leu Met Val Ala Gln Ala Ile Pro Leu Val Gly Glu
305                 310                 315                 320
Leu Val Asp Ile Gly Phe Ala Ala Tyr Asn Phe Val Glu Ser Ile Ile
                325                 330                 335
Asn Leu Phe Gln Val Val His Asn Ser Tyr Asn Arg Pro Ala Tyr Ser
            340                 345                 350
Pro Gly Val Asp Gly Ile Asp Lys Leu Gln Val Gln Leu Gln Gln Ser
            355                 360                 365
Gly Pro Glu Leu Lys Lys Pro Gly Glu Thr Val Lys Ile Ser Cys Lys
370                 375                 380
Ala Ser Gly Tyr Pro Phe Thr Asn Tyr Gly Met Asn Trp Val Lys Gln
385                 390                 395                 400
Ala Pro Gly Gln Gly Leu Lys Trp Met Gly Trp Ile Asn Thr Ser Thr
            405                 410                 415
Gly Glu Ser Thr Phe Ala Asp Asp Phe Lys Gly Arg Phe Asp Phe Ser
            420                 425                 430
Leu Glu Thr Ser Ala Asn Thr Ala Tyr Leu Gln Ile Asn Asn Leu Lys
        435                 440                 445
Ser Glu Asp Met Ala Thr Tyr Phe Cys Ala Arg Trp Glu Val Tyr His
    450                 455                 460
Gly Tyr Val Pro Tyr Trp Gly Gln Gly Thr Thr Val Thr Val Ser Ser
465                 470                 475                 480
Gly Gly Gly Gly Ser Gly Gly Gly Ser Gly Gly Gly Gly Ser Asp
            485                 490                 495
Ile Gln Leu Thr Gln Ser His Lys Phe Leu Ser Thr Ser Val Gly Asp
            500                 505                 510
Arg Val Ser Ile Thr Cys Lys Ala Ser Gln Asp Val Tyr Asn Ala Val
        515                 520                 525
Ala Trp Tyr Gln Gln Lys Pro Gly Gln Ser Pro Lys Leu Leu Ile Tyr
530                 535                 540
```

```
-continued

Ser Ala Ser Ser Arg Tyr Thr Gly Val Pro Ser Arg Phe Thr Gly Ser
545                 550                 555                 560

Gly Ser Gly Pro Asp Phe Thr Phe Thr Ile Ser Ser Val Gln Ala Glu
            565                 570                 575

Asp Leu Ala Val Tyr Phe Cys Gln Gln His Phe Arg Thr Pro Phe Thr
        580                 585                 590

Phe Gly Ser Gly Thr Lys Leu Glu Ile Lys Ala Leu Glu Asp Leu Ser
        595                 600                 605

Ser Glu Arg Arg Phe Ser Ala
    610                 615

(2) INFORMATION FOR SEQ ID NO: 36:

(i) SEQUENCE CHARACTERISTICS:
        (A) LENGTH: 1862 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 1..1851

(xi) SEQUENCE DESCRIPTION: SEQ ID NO: 36:

ATG GAC TAC AAG GAC GAC GAT GAC AAG AAG CTG CAC CAT CAT CAC CAT      48
Met Asp Tyr Lys Asp Asp Asp Asp Lys Lys Leu His His His His His
 1               5                  10                  15

CAC AAG CTT CTG TCT TCT ATC GAA CAA GCA TGC GAT ATT TGC CGA CTT      96
His Lys Leu Leu Ser Ser Ile Glu Gln Ala Cys Asp Ile Cys Arg Leu
             20                  25                  30

AAA AAG CTC AAG TGC TCC AAA GAA AAA CCG AAG TGC GCC AAG TGT CTG     144
Lys Lys Leu Lys Cys Ser Lys Glu Lys Pro Lys Cys Ala Lys Cys Leu
         35                  40                  45

AAG AAC AAC TGG GAG TGT CGC TAC TCT CCC AAA ACC AAA AGG TCT CCG     192
Lys Asn Asn Trp Glu Cys Arg Tyr Ser Pro Lys Thr Lys Arg Ser Pro
     50                  55                  60

CTG ACT AGG GCA CAT CTG ACA GAA GTG GAA TCA AGG CTA GAA AGA CTG     240
Leu Thr Arg Ala His Leu Thr Glu Val Glu Ser Arg Leu Glu Arg Leu
 65                  70                  75                  80

GAA CAG CTA TTT CTA CTG ATT TTT CCT CGA GAA GAC CTT GAC ATG ATT     288
Glu Gln Leu Phe Leu Leu Ile Phe Pro Arg Glu Asp Leu Asp Met Ile
                 85                  90                  95

TTG AAA ATG GAT TCT TTA CAG GAT ATA AAA GCA TTG TTA ACA GGA TTA     336
Leu Lys Met Asp Ser Leu Gln Asp Ile Lys Ala Leu Leu Thr Gly Leu
            100                 105                 110

TTT GTA CAA GAT AAT GTG AAT AAA GAT GCC GTC ACA GAT AGA TTG GCT     384
Phe Val Gln Asp Asn Val Asn Lys Asp Ala Val Thr Asp Arg Leu Ala
        115                 120                 125

TCA GTG GAG ACT GAT ATG CCT CTA ACA TTG AGA CAG CAT AGA ATA AGT     432
Ser Val Glu Thr Asp Met Pro Leu Thr Leu Arg Gln His Arg Ile Ser
130                 135                 140

GCG ACA TCA TCA TCG GAA GAG AGT AGT AAC AAA GGT CAA AGA CAG TTG     480
Ala Thr Ser Ser Ser Glu Glu Ser Ser Asn Lys Gly Gln Arg Gln Leu
145                 150                 155                 160

ACT GTA TCG AGC TCG CTA GCA GTA GGT AGC TCA TTG TCA TGC ATC AAC     528
Thr Val Ser Ser Ser Leu Ala Val Gly Ser Ser Leu Ser Cys Ile Asn
                165                 170                 175

CTG GAT TGG GAT GTT ATC CGT GAT AAA ACT AAA ACT AAG ATC GAA TCT     576
Leu Asp Trp Asp Val Ile Arg Asp Lys Thr Lys Thr Lys Ile Glu Ser
            180                 185                 190
```

```
CTG AAA GAA CAC GGT CCG ATC AAA AAC AAA ATG AGC GAA AGC CCG AAC    624
Leu Lys Glu His Gly Pro Ile Lys Asn Lys Met Ser Glu Ser Pro Asn
        195                 200                 205

AAA ACT GTA TCT GAA GAA AAA GCT AAA CAG TAC CTG GAA GAA TTC CAC    672
Lys Thr Val Ser Glu Glu Lys Ala Lys Gln Tyr Leu Glu Glu Phe His
    210                 215                 220

CAG ACT GCA CTG GAA CAC CCG GAA CTG TCT GAA CTT AAG ACC GTT ACT    720
Gln Thr Ala Leu Glu His Pro Glu Leu Ser Glu Leu Lys Thr Val Thr
225                 230                 235                 240

GGT ACC AAC CCG GTA TTC GCT GGT GCT AAC TAC GCT GCT TGG GCA GTA    768
Gly Thr Asn Pro Val Phe Ala Gly Ala Asn Tyr Ala Ala Trp Ala Val
                245                 250                 255

AAC GTT GCT CAG GTT ATC GAT AGC GAA ACT GCT GAT AAC CTG GAA AAA    816
Asn Val Ala Gln Val Ile Asp Ser Glu Thr Ala Asp Asn Leu Glu Lys
            260                 265                 270

ACT ACC GCG GCT CTG TCT ATC CTG CCG GGT ATC GGT AGC GTA ATG GGC    864
Thr Thr Ala Ala Leu Ser Ile Leu Pro Gly Ile Gly Ser Val Met Gly
        275                 280                 285

ATC GCA GAC GGC GCC GTT CAC CAC AAC ACT GAA GAA ATC GTT GCA CAG    912
Ile Ala Asp Gly Ala Val His His Asn Thr Glu Glu Ile Val Ala Gln
    290                 295                 300

TCT ATC GCT CTG AGC TCT CTG ATG GTT GCT CAG GCC ATC CCG CTG GTA    960
Ser Ile Ala Leu Ser Ser Leu Met Val Ala Gln Ala Ile Pro Leu Val
305                 310                 315                 320

GGT GAA CTG GTT GAT ATC GGT TTC GCT GCA TAC AAC TTC GTT GAA AGC   1008
Gly Glu Leu Val Asp Ile Gly Phe Ala Ala Tyr Asn Phe Val Glu Ser
                325                 330                 335

ATC ATC AAC CTG TTC CAG GTT GTT CAC AAC TCT TAC AAC CGC CCG GCT   1056
Ile Ile Asn Leu Phe Gln Val Val His Asn Ser Tyr Asn Arg Pro Ala
            340                 345                 350

TAC TCT CCG GGT GTC GAC GGT ATC GAT AAG CTT CAG GTA CAA CTG CAG   1104
Tyr Ser Pro Gly Val Asp Gly Ile Asp Lys Leu Gln Val Gln Leu Gln
        355                 360                 365

CAG TCT GGA CCT GAA CTG AAG AAG CCT GGA GAG ACA GTC AAG ATC TCC   1152
Gln Ser Gly Pro Glu Leu Lys Lys Pro Gly Glu Thr Val Lys Ile Ser
    370                 375                 380

TGC AAG GCC TCT GGG TAT CCT TTC ACA AAC TAT GGA ATG AAC TGG GTG   1200
Cys Lys Ala Ser Gly Tyr Pro Phe Thr Asn Tyr Gly Met Asn Trp Val
385                 390                 395                 400

AAG CAG GCT CCA GGA CAG GGT TTA AAG TGG ATG GGC TGG ATT AAC ACC   1248
Lys Gln Ala Pro Gly Gln Gly Leu Lys Trp Met Gly Trp Ile Asn Thr
                405                 410                 415

TCC ACT GGA GAG TCA ACA TTT GCT GAT GAC TTC AAG GGA CGG TTT GAC   1296
Ser Thr Gly Glu Ser Thr Phe Ala Asp Asp Phe Lys Gly Arg Phe Asp
            420                 425                 430

TTC TCT TTG GAA ACC TCT GCC AAC ACT GCC TAT TTG CAG ATC AAC AAC   1344
Phe Ser Leu Glu Thr Ser Ala Asn Thr Ala Tyr Leu Gln Ile Asn Asn
        435                 440                 445

CTC AAA AGT GAA GAC ATG GCT ACA TAT TTC TGT GCA AGA TGG GAG GTT   1392
Leu Lys Ser Glu Asp Met Ala Thr Tyr Phe Cys Ala Arg Trp Glu Val
    450                 455                 460

TAC CAC GGC TAC GTT CCT TAC TGG GGC CAA GGG ACC ACG GTC ACC GTT   1440
Tyr His Gly Tyr Val Pro Tyr Trp Gly Gln Gly Thr Thr Val Thr Val
465                 470                 475                 480

TCC TCT GGC GGT GGC GGT TCT GGT GGC GGT GGC TCC GGC GGT GGC GGT   1488
Ser Ser Gly Gly Gly Gly Ser Gly Gly Gly Gly Ser Gly Gly Gly Gly
                485                 490                 495

TCT GAC ATC CAG CTG ACC CAG TCT CAC AAA TTC CTG TCC ACT TCA GTA   1536
Ser Asp Ile Gln Leu Thr Gln Ser His Lys Phe Leu Ser Thr Ser Val
```

-continued

```
                500                 505                 510
GGA GAC AGG GTC AGC ATC ACC TGC AAG GCC AGT CAG GAT GTG TAT AAT      1584
Gly Asp Arg Val Ser Ile Thr Cys Lys Ala Ser Gln Asp Val Tyr Asn
        515                 520                 525

GCT GTT GCC TGG TAT CAA CAG AAA CCA GGA CAA TCT CCT AAA CTT CTG      1632
Ala Val Ala Trp Tyr Gln Gln Lys Pro Gly Gln Ser Pro Lys Leu Leu
530                 535                 540

ATT TAC TCG GCA TCC TCC CGG TAC ACT GGA GTC CCT TCT CGC TTC ACT      1680
Ile Tyr Ser Ala Ser Ser Arg Tyr Thr Gly Val Pro Ser Arg Phe Thr
545                 550                 555                 560

GGC AGT GGC TCT GGG CCG GAT TTC ACT TTC ACC ATC AGC AGT GTG CAG      1728
Gly Ser Gly Ser Gly Pro Asp Phe Thr Phe Thr Ile Ser Ser Val Gln
                565                 570                 575

GCT GAA GAC CTG GCA GTT TAT TTC TGT CAG CAA CAT TTT CGT ACT CCA      1776
Ala Glu Asp Leu Ala Val Tyr Phe Cys Gln Gln His Phe Arg Thr Pro
            580                 585                 590

TTC ACG TTC GGC TCG GGG ACA AAA TTG GAG ATC AAA GCT CTA GAG GAT      1824
Phe Thr Phe Gly Ser Gly Thr Lys Leu Glu Ile Lys Ala Leu Glu Asp
        595                 600                 605

CTC TCG AGT GAG AGA AGA TTT TCA GCC TGATACAGAT T                     1862
Leu Ser Ser Glu Arg Arg Phe Ser Ala
    610                 615
```

(2) INFORMATION FOR SEQ ID NO: 37:

(i) SEQUENCE CHARACTERISTICS:
        (A) LENGTH: 617 amino acids
        (B) TYPE: amino acid
        (D) TOPOLOGY: linear (ii) MOLECULE TYPE: protein (xi) SEQUENCE DESCRIPTION: SEQ ID NO: 37:

```
Met Asp Tyr Lys Asp Asp Asp Lys Lys Leu His His His His
1               5                   10                  15

His Lys Leu Leu Ser Ser Ile Glu Gln Ala Cys Asp Ile Cys Arg Leu
            20                  25                  30

Lys Lys Leu Lys Cys Ser Lys Glu Lys Pro Lys Cys Ala Lys Cys Leu
        35                  40                  45

Lys Asn Asn Trp Glu Cys Arg Tyr Ser Pro Lys Thr Lys Arg Ser Pro
    50                  55                  60

Leu Thr Arg Ala His Leu Thr Glu Val Glu Ser Arg Leu Glu Arg Leu
65                  70                  75                  80

Glu Gln Leu Phe Leu Leu Ile Phe Pro Arg Glu Asp Leu Asp Met Ile
                85                  90                  95

Leu Lys Met Asp Ser Leu Gln Asp Ile Lys Ala Leu Leu Thr Gly Leu
            100                 105                 110

Phe Val Gln Asp Asn Val Asn Lys Asp Ala Val Thr Asp Arg Leu Ala
        115                 120                 125

Ser Val Glu Thr Asp Met Pro Leu Thr Leu Arg Gln His Arg Ile Ser
    130                 135                 140

Ala Thr Ser Ser Ser Glu Glu Ser Ser Asn Lys Gly Gln Arg Gln Leu
145                 150                 155                 160

Thr Val Ser Ser Ser Leu Ala Val Gly Ser Ser Leu Ser Cys Ile Asn
                165                 170                 175

Leu Asp Trp Asp Val Ile Arg Asp Lys Thr Lys Thr Lys Ile Glu Ser
            180                 185                 190

Leu Lys Glu His Gly Pro Ile Lys Asn Lys Met Ser Glu Ser Pro Asn
```

-continued

```
            195                 200                 205
Lys Thr Val Ser Glu Glu Lys Ala Lys Gln Tyr Leu Glu Glu Phe His
            210                 215                 220
Gln Thr Ala Leu Glu His Pro Glu Leu Ser Glu Leu Lys Thr Val Thr
225                 230                 235                 240
Gly Thr Asn Pro Val Phe Ala Gly Ala Asn Tyr Ala Ala Trp Ala Val
                245                 250                 255
Asn Val Ala Gln Val Ile Asp Ser Glu Thr Ala Asp Asn Leu Glu Lys
                260                 265                 270
Thr Thr Ala Ala Leu Ser Ile Leu Pro Gly Ile Gly Ser Val Met Gly
            275                 280                 285
Ile Ala Asp Gly Ala Val His His Asn Thr Glu Glu Ile Val Ala Gln
            290                 295                 300
Ser Ile Ala Leu Ser Ser Leu Met Val Ala Gln Ala Ile Pro Leu Val
305                 310                 315                 320
Gly Glu Leu Val Asp Ile Gly Phe Ala Ala Tyr Asn Phe Val Glu Ser
                325                 330                 335
Ile Ile Asn Leu Phe Gln Val Val His Asn Ser Tyr Asn Arg Pro Ala
                340                 345                 350
Tyr Ser Pro Gly Val Asp Gly Ile Asp Lys Leu Gln Val Gln Leu Gln
            355                 360                 365
Gln Ser Gly Pro Glu Leu Lys Lys Pro Gly Glu Thr Val Lys Ile Ser
            370                 375                 380
Cys Lys Ala Ser Gly Tyr Pro Phe Thr Asn Tyr Gly Met Asn Trp Val
385                 390                 395                 400
Lys Gln Ala Pro Gly Gln Gly Leu Lys Trp Met Gly Trp Ile Asn Thr
                405                 410                 415
Ser Thr Gly Glu Ser Thr Phe Ala Asp Asp Phe Lys Gly Arg Phe Asp
            420                 425                 430
Phe Ser Leu Glu Thr Ser Ala Asn Thr Ala Tyr Leu Gln Ile Asn Asn
            435                 440                 445
Leu Lys Ser Glu Asp Met Ala Thr Tyr Phe Cys Ala Arg Trp Glu Val
            450                 455                 460
Tyr His Gly Tyr Val Pro Tyr Trp Gly Gln Gly Thr Thr Val Thr Val
465                 470                 475                 480
Ser Ser Gly Gly Gly Gly Ser Gly Gly Gly Gly Ser Gly Gly Gly Gly
                485                 490                 495
Ser Asp Ile Gln Leu Thr Gln Ser His Lys Phe Leu Ser Thr Ser Val
                500                 505                 510
Gly Asp Arg Val Ser Ile Thr Cys Lys Ala Ser Gln Asp Val Tyr Asn
            515                 520                 525
Ala Val Ala Trp Tyr Gln Gln Lys Pro Gly Gln Ser Pro Lys Leu Leu
            530                 535                 540
Ile Tyr Ser Ala Ser Ser Arg Tyr Thr Gly Val Pro Ser Arg Phe Thr
545                 550                 555                 560
Gly Ser Gly Ser Gly Pro Asp Phe Thr Phe Thr Ile Ser Ser Val Gln
                565                 570                 575
Ala Glu Asp Leu Ala Val Tyr Phe Cys Gln Gln His Phe Arg Thr Pro
                580                 585                 590
Phe Thr Phe Gly Ser Gly Thr Lys Leu Glu Ile Lys Ala Leu Glu Asp
            595                 600                 605
Leu Ser Ser Glu Arg Arg Phe Ser Ala
            610                 615
```

(2) INFORMATION FOR SEQ ID NO: 38:

(i) SEQUENCE CHARACTERISTICS:
        (A) LENGTH: 1605 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 64..1551

(xi) SEQUENCE DESCRIPTION: SEQ ID NO: 38:

```
ATGAAAAAGA CAGCTATCGC GATTGCAGTG GCACTGGCTG GTTTCGCTAC CGTTGCGCAA         60

GCT GAC TAC AAG GAC GAC GAT GAC AAG CTG CAC CAT CAT CAC CAT CAC         108
Ala Asp Tyr Lys Asp Asp Asp Asp Lys Leu His His His His His His
  1               5                  10                  15

AAG CTT CTG TCT TCT ATC GAA CAA GCA TGC GAT ATT TGC CGA CTT AAA         156
Lys Leu Leu Ser Ser Ile Glu Gln Ala Cys Asp Ile Cys Arg Leu Lys
             20                  25                  30

AAG CTC AAG TGC TCC AAA GAA AAA CCG AAG TGC GCC AAG TGT CTG AAG         204
Lys Leu Lys Cys Ser Lys Glu Lys Pro Lys Cys Ala Lys Cys Leu Lys
         35                  40                  45

AAC AAC TGG GAG TGT CGC TAC TCT CCC AAA ACC AAA AGG TCT CCG CTG         252
Asn Asn Trp Glu Cys Arg Tyr Ser Pro Lys Thr Lys Arg Ser Pro Leu
     50                  55                  60

ACT AGG GCA CAT CTG ACA GAA GTG GAA TCA AGG CTA GAA AGA CTG GAA         300
Thr Arg Ala His Leu Thr Glu Val Glu Ser Arg Leu Glu Arg Leu Glu
 65                  70                  75

CAG CTA TTT CTA CTG ATT TTT CCT CGA GAA GAC CTT GAC ATG ATT TTG         348
Gln Leu Phe Leu Leu Ile Phe Pro Arg Glu Asp Leu Asp Met Ile Leu
 80                  85                  90                  95

AAA ATG GAT TCT TTA CAG GAT ATA AAA GCA TTG TTA ACA GGA TTA TTT         396
Lys Met Asp Ser Leu Gln Asp Ile Lys Ala Leu Leu Thr Gly Leu Phe
                100                 105                 110

GTA CAA GAT AAT GTG AAT AAA GAT GCC GTC ACA GAT AGA TTG GCT TCA         444
Val Gln Asp Asn Val Asn Lys Asp Ala Val Thr Asp Arg Leu Ala Ser
            115                 120                 125

GTG GAG ACT GAT ATG CCT CTA ACA TTG AGA CAG CAT AGA ATA AGT GCG         492
Val Glu Thr Asp Met Pro Leu Thr Leu Arg Gln His Arg Ile Ser Ala
        130                 135                 140

ACA TCA TCA TCG GAA GAG AGT AGT AAC AAA GGT CAA AGA CAG TTG ACT         540
Thr Ser Ser Ser Glu Glu Ser Ser Asn Lys Gly Gln Arg Gln Leu Thr
    145                 150                 155

GTA TCG AGC TCG CTA GCA GTA GGT AGC TCA TTG TCA TGC ATC AAC CTG         588
Val Ser Ser Ser Leu Ala Val Gly Ser Ser Leu Ser Cys Ile Asn Leu
160                 165                 170                 175

GAT TGG GAT GTT ATC CGT GAT AAA ACT AAA ACT AAG ATC GAA TCT CTG         636
Asp Trp Asp Val Ile Arg Asp Lys Thr Lys Thr Lys Ile Glu Ser Leu
                180                 185                 190

AAA GAA CAC GGT CCG ATC AAA AAC AAA ATG AGC GAA AGC CCG AAC AAA         684
Lys Glu His Gly Pro Ile Lys Asn Lys Met Ser Glu Ser Pro Asn Lys
            195                 200                 205

ACT GTA TCT GAA GAA AAA GCT AAA CAG TAC CTG GAA GAA TTC CAC CAG         732
Thr Val Ser Glu Glu Lys Ala Lys Gln Tyr Leu Glu Glu Phe His Gln
        210                 215                 220

ACT GCA CTG GAA CAC CCG GAA CTG TCT GAA CTT AAG ACC GTT ACT GGT         780
Thr Ala Leu Glu His Pro Glu Leu Ser Glu Leu Lys Thr Val Thr Gly
    225                 230                 235
```

```
ACC AAC CCG GTA TTC GCT GGT GCT AAC TAC GCT GCT TGG GCA GTA AAC      828
Thr Asn Pro Val Phe Ala Gly Ala Asn Tyr Ala Ala Trp Ala Val Asn
240             245                 250                 255

GTT GCT CAG GTT ATC GAT AGC GAA ACT GCT GAT AAC CTG GAA AAA ACT      876
Val Ala Gln Val Ile Asp Ser Glu Thr Ala Asp Asn Leu Glu Lys Thr
                260                 265                 270

ACC GCG GCT CTG TCT ATC CTG CCG GGT ATC GGT AGC GTA ATG GGC ATC      924
Thr Ala Ala Leu Ser Ile Leu Pro Gly Ile Gly Ser Val Met Gly Ile
            275                 280                 285

GCA GAC GGC GCC GTT CAC CAC AAC ACT GAA GAA ATC GTT GCA CAG TCT      972
Ala Asp Gly Ala Val His His Asn Thr Glu Glu Ile Val Ala Gln Ser
        290                 295                 300

ATC GCT CTG AGC TCT CTG ATG GTT GCT CAG GCC ATC CCG CTG GTA GGT     1020
Ile Ala Leu Ser Ser Leu Met Val Ala Gln Ala Ile Pro Leu Val Gly
    305                 310                 315

GAA CTG GTT GAT ATC GGT TTC GCT GCA TAC AAC TTC GTT GAA AGC ATC     1068
Glu Leu Val Asp Ile Gly Phe Ala Ala Tyr Asn Phe Val Glu Ser Ile
320                 325                 330                 335

ATC AAC CTG TTC CAG GTT GTT CAC AAC TCT TAC AAC CGC CCG GCT TAC     1116
Ile Asn Leu Phe Gln Val Val His Asn Ser Tyr Asn Arg Pro Ala Tyr
                340                 345                 350

TCT CCG GGT GTC GAC GGT ATC GAT AAG CTT GAG CTA GCA CCT ACT TCA     1164
Ser Pro Gly Val Asp Gly Ile Asp Lys Leu Glu Leu Ala Pro Thr Ser
            355                 360                 365

AGT TCT ACA AAG AAA ACA CAG CTA CAA CTG GAG CAT TTA CTG CTG GAT     1212
Ser Ser Thr Lys Lys Thr Gln Leu Gln Leu Glu His Leu Leu Leu Asp
        370                 375                 380

TTA CAG ATG ATT TTG AAT GGA ATT AAT AAT TAC AAG AAT CCC AAA CTC     1260
Leu Gln Met Ile Leu Asn Gly Ile Asn Asn Tyr Lys Asn Pro Lys Leu
    385                 390                 395

ACC AGG ATG CTC ACA TTT AAG TTT TAC ATG CCC AAG AAG GCC ACA GAA     1308
Thr Arg Met Leu Thr Phe Lys Phe Tyr Met Pro Lys Lys Ala Thr Glu
400                 405                 410                 415

CTG AAA CAT CTT CAG TGT CTA GAA GAA GAA CTC AAA CCT CTG GAG GAA     1356
Leu Lys His Leu Gln Cys Leu Glu Glu Glu Leu Lys Pro Leu Glu Glu
                420                 425                 430

GTG CTA AAT TTA GCT CAA AGC AAA AAC TTT CAC TTA AGA CCC AGG GAC     1404
Val Leu Asn Leu Ala Gln Ser Lys Asn Phe His Leu Arg Pro Arg Asp
            435                 440                 445

TTA ATC AGC AAT ATC AAC GTA ATA GTT CTG GAA CTA AAG GGA TCT GAA     1452
Leu Ile Ser Asn Ile Asn Val Ile Val Leu Glu Leu Lys Gly Ser Glu
        450                 455                 460

ACA ACA TTC ATG TGT GAA TAT GCT GAT GAG ACA GCA ACC ATT GTA GAA     1500
Thr Thr Phe Met Cys Glu Tyr Ala Asp Glu Thr Ala Thr Ile Val Glu
    465                 470                 475

TTT CTG AAC AGA TGG ATT ACC TTT TGT CAA AGC ATC ATC TCA ACA CTA     1548
Phe Leu Asn Arg Trp Ile Thr Phe Cys Gln Ser Ile Ile Ser Thr Leu
480                 485                 490                 495

ACT TAAGAATTCT GGAGATCTCT CGAGTGAGAG AAGATTTTCA GCCTGATACA GATT     1605
Thr (2) INFORMATION FOR SEQ ID NO: 39:

(i) SEQUENCE CHARACTERISTICS:
        (A) LENGTH: 496 amino acids
        (B) TYPE: amino acid
        (D) TOPOLOGY: linear (ii) MOLECULE TYPE: protein (xi) SEQUENCE DESCRIPTION: SEQ ID NO: 39:
```

-continued

```
Asp Tyr Lys Asp Asp Asp Lys Leu His His His His His Lys
 1               5                      10                  15

Leu Leu Ser Ser Ile Glu Gln Ala Cys Asp Ile Cys Arg Leu Lys Lys
            20                  25                  30

Leu Lys Cys Ser Lys Glu Lys Pro Lys Cys Ala Lys Cys Leu Lys Asn
        35                  40                  45

Asn Trp Glu Cys Arg Tyr Ser Pro Lys Thr Lys Arg Ser Pro Leu Thr
    50                  55                  60

Arg Ala His Leu Thr Glu Val Glu Ser Arg Leu Glu Arg Leu Glu Gln
 65                  70                  75                  80

Leu Phe Leu Leu Ile Phe Pro Arg Glu Asp Leu Asp Met Ile Leu Lys
                85                  90                  95

Met Asp Ser Leu Gln Asp Ile Lys Ala Leu Leu Thr Gly Leu Phe Val
            100                 105                 110

Gln Asp Asn Val Asn Lys Asp Ala Val Thr Asp Arg Leu Ala Ser Val
            115                 120                 125

Glu Thr Asp Met Pro Leu Thr Leu Arg Gln His Arg Ile Ser Ala Thr
            130                 135                 140

Ser Ser Ser Glu Glu Ser Ser Asn Lys Gly Gln Arg Gln Leu Thr Val
145                 150                 155                 160

Ser Ser Ser Leu Ala Val Gly Ser Ser Leu Ser Cys Ile Asn Leu Asp
            165                 170                 175

Trp Asp Val Ile Arg Asp Lys Thr Lys Thr Lys Ile Glu Ser Leu Lys
            180                 185                 190

Glu His Gly Pro Ile Lys Asn Lys Met Ser Glu Ser Pro Asn Lys Thr
            195                 200                 205

Val Ser Glu Glu Lys Ala Lys Gln Tyr Leu Glu Glu Phe His Gln Thr
210                 215                 220

Ala Leu Glu His Pro Glu Leu Ser Glu Leu Lys Thr Val Thr Gly Thr
225                 230                 235                 240

Asn Pro Val Phe Ala Gly Ala Asn Tyr Ala Ala Trp Ala Val Asn Val
            245                 250                 255

Ala Gln Val Ile Asp Ser Glu Thr Ala Asp Asn Leu Glu Lys Thr Thr
            260                 265                 270

Ala Ala Leu Ser Ile Leu Pro Gly Ile Gly Ser Val Met Gly Ile Ala
            275                 280                 285

Asp Gly Ala Val His His Asn Thr Glu Glu Ile Val Ala Gln Ser Ile
            290                 295                 300

Ala Leu Ser Ser Leu Met Val Ala Gln Ala Ile Pro Leu Val Gly Glu
305                 310                 315                 320

Leu Val Asp Ile Gly Phe Ala Ala Tyr Asn Phe Val Glu Ser Ile Ile
            325                 330                 335

Asn Leu Phe Gln Val Val His Asn Ser Tyr Asn Arg Pro Ala Tyr Ser
            340                 345                 350

Pro Gly Val Asp Gly Ile Asp Lys Leu Glu Leu Ala Pro Thr Ser Ser
            355                 360                 365

Ser Thr Lys Lys Thr Gln Leu Gln Leu Glu His Leu Leu Leu Asp Leu
    370                 375                 380

Gln Met Ile Leu Asn Gly Ile Asn Asn Tyr Lys Asn Pro Lys Leu Thr
385                 390                 395                 400

Arg Met Leu Thr Phe Lys Phe Tyr Met Pro Lys Lys Ala Thr Glu Leu
                405                 410                 415
```

```
Lys His Leu Gln Cys Leu Glu Glu Leu Lys Pro Leu Glu Glu Val
            420                 425                 430

Leu Asn Leu Ala Gln Ser Lys Asn Phe His Leu Arg Pro Arg Asp Leu
            435                 440                 445

Ile Ser Asn Ile Asn Val Ile Val Leu Glu Leu Lys Gly Ser Glu Thr
450                 455                 460

Thr Phe Met Cys Glu Tyr Ala Asp Glu Thr Ala Thr Ile Val Glu Phe
465                 470                 475                 480

Leu Asn Arg Trp Ile Thr Phe Cys Gln Ser Ile Ile Ser Thr Leu Thr
            485                 490                 495
```

(2) INFORMATION FOR SEQ ID NO: 40:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO: 40:

```
Glu Lys Leu Glu Ser Ser Asp Tyr Lys Asp Glu Leu
1               5                   10
```

(2) INFORMATION FOR SEQ ID NO: 41:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO: 41:

```
His His His His
1
```

(2) INFORMATION FOR SEQ ID NO: 42:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO: 42:

```
Ser Ser Asp Tyr Lys Asp Glu Leu
1               5
```

(2) INFORMATION FOR SEQ ID NO: 43:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO: 43:

```
Gly Gly Gly Gly Ser
1               5
```

(2) INFORMATION FOR SEQ ID NO: 44:

(i) SEQUENCE CHARACTERISTICS:

(A) LENGTH: 17 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 44:

CGGAGGACAG TCCTCCG                                                    17

(2) INFORMATION FOR SEQ ID NO: 45:

(i) SEQUENCE CHARACTERISTICS:
            (A) LENGTH: 4 amino acids
            (B) TYPE: amino acid
            (D) TOPOLOGY: linear (ii) MOLECULE TYPE: peptide (xi) SEQUENCE DESCRIPTION: SEQ ID NO: 45:

Lys Asp Glu Leu
1

(2) INFORMATION FOR SEQ ID NO: 46:

(i) SEQUENCE CHARACTERISTICS:
            (A) LENGTH: 5 amino acids
            (B) TYPE: amino acid
            (D) TOPOLOGY: linear (ii) MOLECULE TYPE: peptide (xi) SEQUENCE DESCRIPTION: SEQ ID NO: 46:

Arg Glu Asp Leu Lys
1               5

(2) INFORMATION FOR SEQ ID NO: 47:

(i) SEQUENCE CHARACTERISTICS:
            (A) LENGTH: 4 amino acids
            (B) TYPE: amino acid
            (D) TOPOLOGY: linear (ii) MOLECULE TYPE: peptide (xi) SEQUENCE DESCRIPTION: SEQ ID NO: 47:

His Asp Glu Leu
1

(2) INFORMATION FOR SEQ ID NO: 48:

(i) SEQUENCE CHARACTERISTICS:
            (A) LENGTH: 21 amino acids
            (B) TYPE: amino acid
            (D) TOPOLOGY: linear (ii) MOLECULE TYPE: peptide (xi) SEQUENCE DESCRIPTION: SEQ ID NO: 48:

Met Lys Lys Thr Ala Ile Ala Ile Ala Val Ala Leu Ala Gly Phe Ala
1               5                   10                  15

Thr Val Ala Gln Ala
            20

(2) INFORMATION FOR SEQ ID NO: 49:

(i) SEQUENCE CHARACTERISTICS:
            (A) LENGTH: 15 amino acids (B) TYPE: amino acid
            (D) TOPOLOGY: linear (ii) MOLECULE TYPE: peptide (xi) SEQUENCE DESCRIPTION: SEQ ID NO: 49:

Gly Gly Gly Gly Ser Gly Gly Gly Gly Ser Gly Gly Gly Gly Ser
1               5                   10                  15

(2) INFORMATION FOR SEQ ID NO: 50:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 50:

CGCTAGCTGG TGGTG                                                          15

(2) INFORMATION FOR SEQ ID NO: 51:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 51:

TCGACACCAC CAGCTAGCGA GCT                                                 23

(2) INFORMATION FOR SEQ ID NO: 52:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 52:

CGTGTCAGGC TAGCAGTAGG TAGC                                                24

(2) INFORMATION FOR SEQ ID NO: 53:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 53:

CATGCGTGTC GACACCCGGA GAGTAAGC                                            28

(2) INFORMATION FOR SEQ ID NO: 54:

(i) SEQUENCE CHARACTERISTICS:
            (A) LENGTH: 53 base pairs
            (B) TYPE: nucleic acid
            (C) STRANDEDNESS: single
            (D) TOPOLOGY: linear -continued

```
    (ii) MOLECULE TYPE: DNA (xi) SEQUENCE DESCRIPTION: SEQ ID NO: 54:

TATGGACTAC AAGGACGACG ATGACAAGAA GCTGCACCAT CATCACCATC ACA          53

(2) INFORMATION FOR SEQ ID NO: 55:

(i) SEQUENCE CHARACTERISTICS:
          (A) LENGTH: 55 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO: 55:

AGCTTGTGAT GGTGATGATG GTGCAGCTTC TTGTCATCGT CGTCCTTGTA GTCCA        55

(2) INFORMATION FOR SEQ ID NO:56:

(i) SEQUENCE CHARACTERISTICS:
          (A) LENGTH: 34 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:56:

TGAGGAGACG GTGACCGTGG TCCCTTGGCC CCAG                               34

(2) INFORMATION FOR SEQ ID NO:57:

(i) SEQUENCE CHARACTERISTICS:
          (A) LENGTH: 22 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:57:

AGGTSMARCT GCAGSAGTCW GG                                            22

(2) INFORMATION FOR SEQ ID NO:58:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:58:

GACATTCAGC TGACCCAGTC TCCA                                          24
```